US007888028B2

(12) United States Patent
Felden

(10) Patent No.: US 7,888,028 B2
(45) Date of Patent: Feb. 15, 2011

(54) EUBACTERIAL TMRNA SEQUENCES AND USES THEREOF

(75) Inventor: Brice Felden, Le Lou du Lac (FR)

(73) Assignee: University of Utah Research Foundation, Salt Lake City, UT (US)

( * ) Notice: Subject to any disclaimer, the term of this patent is extended or adjusted under 35 U.S.C. 154(b) by 271 days.

(21) Appl. No.: 12/163,317

(22) Filed: Jun. 27, 2008

(65) Prior Publication Data

US 2009/0117568 A1 May 7, 2009

Related U.S. Application Data

(62) Division of application No. 11/329,230, filed on Jan. 11, 2006, now Pat. No. 7,611,843, which is a division of application No. 09/958,206, filed as application No. PCT/US00/08988 on Apr. 6, 2000, now Pat. No. 7,115, 366.

(60) Provisional application No. 60/128,058, filed on Apr. 7, 1999.

(51) Int. Cl.

| | |
|---|---|
| ***C12Q 1/68*** | (2006.01) |
| ***A01N 43/04*** | (2006.01) |
| ***A61K 31/70*** | (2006.01) |
| ***C07H 21/02*** | (2006.01) |
| ***C07H 21/04*** | (2006.01) |
| ***C12P 19/34*** | (2006.01) |

(52) U.S. Cl. ......................... 435/6; 435/91.1; 435/91.2; 514/44 R; 536/23.1; 536/23.7

(58) Field of Classification Search ....................... None
See application file for complete search history.

(56) References Cited

U.S. PATENT DOCUMENTS 6,551,795 B1 * 4/2003 Rubenfield et al. ............. 435/6

OTHER PUBLICATIONS

Felden et al., "Eubacterial tmRNAs: everywhere except the alpha-Proteobacteria?" Biochimica et Biophysica Acta 1446:145-148, 1999.

N. Nameki et al., "Three of four pseudoknots in tmRNA are interchangeable and are substitutable with single-stranded RNAs," FEBS Lett 470(3):345-349, Mar. 31, 2000.

N. Nameki et al., "Functional and structural analysis of a pseudoknot upstream of the tag-encoded sequence in *E. coli* tmRNA," J. Mol. Biol 286(3):733-744, Feb. 26, 1999.

W. Schönhuber et al., "Utilization of tmRNA squences for bacterial identification," MBC Microbiology 2001, 1:20 (online, 8 pages).

K.P. Williams et al., "Phylogenetic analysis of tmRNA secondary structure," RNA 2:1306-1310, 1996.

Zwieb et al., "Survey and Summary, Comparative sequence analysis of tmRNA," Nucleic Acids Research 27(10):2063-2071, 1999.

Huang, C. et al., "Charged tmRNA but not tmRNA-mediated proteolysis is essential for Neisseria gonorrhoeae viability," The EMBO Journal, vol. 19, No. 5, pp. 1098-1107, 2000, copyright European Molecular Biology Organization.

Ley, B.E. et al., "Eubacterial approach to the diagnosis of bacterial infection," Archives of Disease in Childhood 1997; 77:148-149.

* cited by examiner

*Primary Examiner*—Janet Epps-Smith
(74) *Attorney, Agent, or Firm*—Rothwell, Figg, Ernst & Manbeck p.c.

(57) ABSTRACT

The present invention is directed to eubacterial tmDNA sequences and the corresponding tmRNA sequences. The present invention is further directed to alignments of eubacterial tmDNA sequences and the use of the sequences and sequence alignments for the development of antibacterial drugs. The present invention is also directed to the use of the sequences for the development of diagnostic assays.

6 Claims, 24 Drawing Sheets

```
                       H1                      H5             H2
              5'      ━━━━━                 ━━━━━━━━━       ━━━━━
Tab.saccha   ********-**********CGGGGGUAGUAGAGGUAAAAGUAGCGAGC
C.acetobut   ********-******************************* *******
C.stercora   ********-**********CGGGGUUAU-UGAAGCAAGAGUAGCGGGU
C.perfrige   ********-**********CGGGGGUAAGAUGGGUUUGAUAAGCGAGU
C.lentocel   ********-**********CGGGGGUCACAUCUACUGGGGCAGCCAUC
Hlb.mobili   ********-**********CGGGGAACGUGUUUGCUUGGGAUGCGAGC
Hsp.gestii   ********-**********CGGGGAACGUGUUUGCUUAGGACGCGAGC
Bb.brevis    ********-**********CGGGGAUGG-UAGAGCAUGAGAAGCGAGC
B.subtilis   GGGGACGUU-ACGGAUUCGACAGGGAUGGAUCGAGCUUGAGCUGCGAGC
B.badius     ********-**********CAGGGAUAGUUCGAGCUUGGGCUGCGAGC
B.megateri   ggggacguu-acggauucgacAGGG-UAGUUCGAGCUUAGGUUGCGAGU
B.thermole   ********-**********CGGGGGUAGGUCGAGCUUAAGCGGCGAGC
Eco.fecium   ********-**********CAGGCACAGUUUGAGCUUGAAUUGCGUUU
Eco.faecal   GGGGGCGUU-ACGGAUUCGACAGGCAUAG-UUGAGCUUGAAUUGCGUUU
Stc.pyogen   GGGGUUGUU-ACGGAUUCGACAGGCAUUA-UGAGGCAUGUUUUGCGUCC
Stc.pneumo   GGGGUCGUU-ACGGAUUCGACAGGCAUUA-UGAGGCAUAUUUUGCGACU
Stc.gordon   GGGGUCGUU-ACGGAUUCGACAGGCAUUA-UGAGGCAUAUUUUGCGACU
Stc.mutans   GGGGUCGUU-ACGGAUUCGACAGGCAUUA-UGAGACCUAUUUUGCGACU
Stp.epider   ********-**********CAGGGUCC-CCGAGCUUAUUAAGCGUGU
Stp.aureuT   GGGGACGUUCAUGGAUUCGACAGGGGUCCCCCGAGCUCAUUAAGCGUGU
L.acidophi   ********-**********CAGGCGUAG-ACCCGCAUUGACUGCGGUU
             ▭━ ▭━ ▭━━━ ▭━━━ ▭━━━  ←PK1
Tab.saccha   CGAGGU--UCCAUCUG-CUCG-UAAA-ACGGUGGAC---UUAAAU
C.acetobut   ****************-*************___******
C.stercora   AGAGGAUUCUCGUUGGCCUCU-UUAA-AAAACGAGA--GCUAAAA
C.perfrige   CGAGGGAAGCAUGGUGCCUCGAUAAUAAAGUAUGCA---UUAAAG
C.lentocel   CGUAGAACGCCGGAGUCUACG-UUAA-AAGCUGGCA---CUUAAA
Hlb.mobili   CGGGUUG--CCGCCAGGACCG-UAAA--AAGGGCGG---AAGGCU
Hsp.gestii   CGGGUUG--CCGCCAGGACCG-UAAA--AAGGGCGG---AAGGCU
Bb.brevis    CGGGGGG--UUGCGGACCUCG-UCAC--CAACGCAA---ACGCCA
B.subtilis   CGAGA-----GGCG-AUCUCG-UAAA---CACGCAC---UUAAAU
B.badius     CGGAG-----GGCCGUCUUCG-U-AC-CAACGCAAACGCCUAAAU
B.megateri   CGAGG-----AGAUGGCCUCG-UUAA--AACAUCAA-CGCCAAUA
B.thermole   CGAGG----GGGACGUCCUCG-UAAA--AACGUCAC---CUAAAG
Eco.fecium   CGUAG----GUUACGUCUACG-UUAAAACGUUACAG---UUAAAU
Eco.faecal   CGUAG----GUUACGGCUACG-UUAAAACGUUACAG---UUAAAU
Stc.pyogen   CAUC--------GGCAGAUG-UAAA---UUGCCAG---UUAAAU
Stc.pneumo   CGU---------GUGGCGACG-UAAA---CGCUCAG---UUAAAU
Stc.gordon   CAUC--------UAGCGGAUG-UAAA---ACGCCAG---UUAAAU
Stc.mutans   CAUC--------UAGCGGAUG-UAAA---ACGCCAG---UUAAAU
Stp.epider   CGGAG-----GGUUGGCUCCG-UCAUCAACACAUUUCGGUUAAAU
Stp.aureus   CGGAG-----GGUUGUCUUCG-UCAUCAACACACACAGUUUAUA-
L.acidophi   CGUAG----GUUACGUCUACG-UAAAAACGUUACAG---UUAAAU
```

FIG. 3A

Figure 3B:
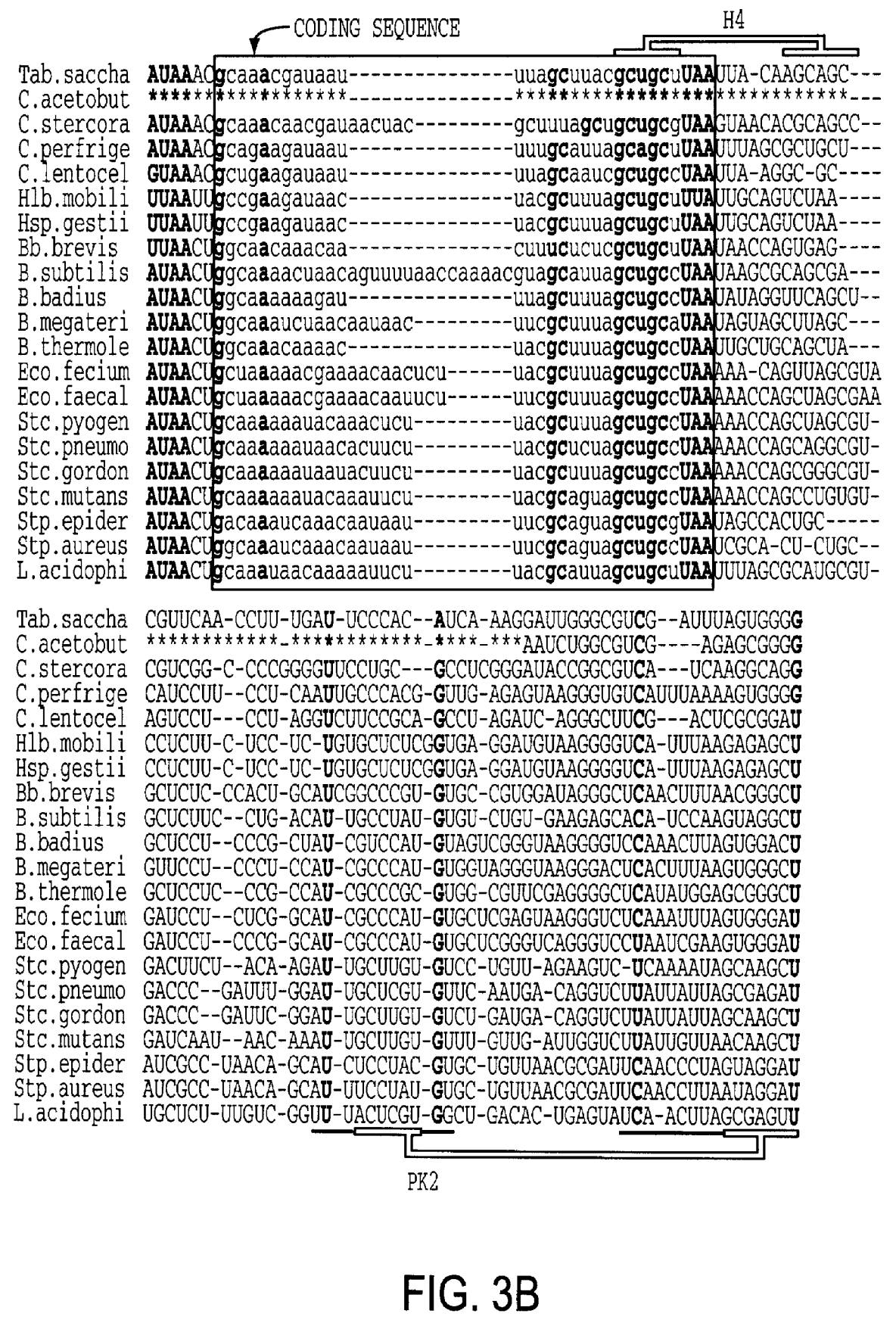

```
                         CODING SEQUENCE                                           H4
Tab.saccha  AUAAACgcaaacgauaau---------------uuagcuuacgcugcuUAAUUA-CAAGCAGC---
C.acetobut  ******************---------------*****************************---
C.stercora  AUAAACgcaaacaacgauaacuac---------gcuuuagcugcugcgUAAGUAACACGCAGCC--
C.perfrige  AUAAACgcagaagauaau---------------uuugcauuagcagcuUAAUUUAGCGCUGCU---
C.lentocel  GUAAACgcugaagauaau---------------uuagcaaucgcugccUAAUUA-AGGC-GC----
Hlb.mobili  UUAAUUgccgaagauaac---------------uacgcuuuagcugcuUUAUUGCAGUCUAA----
Hsp.gestii  UUAAUUgccgaagauaac---------------uacgcuuuagcugcuUAAUUGCAGUCUAA----
Bb.brevis   UUAACUggcaacaaacaa---------------cuuucucucgcugcuUAAUAACCAGUGAG----
B.subtilis  AUAACUggcaaaacuaacaguuuuaaccaaaacguagcauuagcugccUAAUAAGCGCAGCGA---
B.badius    AUAACUggcaaaaaagau---------------uuagcuuuagcugccUAAUAUAGGUUCAGCU--
B.megateri  AUAACUggcaaaucuaacaauaac---------uucgcuuuagcugcaUAAUAGUAGCUUAGC---
B.thermole  AUAACUggcaaacaaaac---------------uacgcuuuagcugccUAAUUGCUGCAGCUA---
Eco.fecium  AUAACUgcuaaaaacgaaaacaacucu------uacgcuuuagcugccUAAAAA-CAGUUAGCGUA
Eco.faecal  AUAACUgcuaaaaacgaaaacaauucu------uucgcuuuagcugccUAAAAACCAGCUAGCGAA
Stc.pyogen  AUAACUgcaaaaaauacaaacucu---------uacgcuuuagcugccUAAAAACCAGCUAGCGU-
Stc.pneumo  AUAACUgcaaaaaauaacacuucu---------uacgcucuagcugccUAAAAACCAGCAGGCGU-
Stc.gordon  AUAACUgcaaaaaauaauacuucu---------uacgcuuuagcugccUAAAAACCAGCGGGCGU-
Stc.mutans  AUAACUgcaaaaaauacaaauucu---------uacgcaguagcugccUAAAAACCAGCCUGUGU-
Stp.epider  AUAACUgacaaaucaaacaauaau---------uucgcaguagcugcgUAAUAGCCACUGC-----
Stp.aureus  AUAACUggcaaaucaaacaauaau---------uucgcaguagcugccUAAUCGCA-CU-CUGC--
L.acidophi  AUAACUgcaaauaacaaaaauucu---------uacgcauuagcugcuUAAUUUAGCGCAUGCGU-

Tab.saccha  CGUUCAA-CCUU-UGAU-UCCCAC--AUCA-AAGGAUUGGGCGUCG--AUUUAGUGGGG
C.acetobut  ************-***********-****-***AAUCUGGCGUCG----AGAGCGGGG
C.stercora  CGUCGG-C-CCCGGGGUUCCUGC---GCCUCGGGAUACCGGCGUCA---UCAAGGCAGG
C.perfrige  CAUCCUU--CCU-CAAUUGCCCACG-GUUG-AGAGUAAGGGUGUCAUUUAAAAGUGGGG
C.lentocel  AGUCCU---CCU-AGGUCUUCCGCA-GCCU-AGAUC-AGGGCUUCG---ACUCGCGGAU
Hlb.mobili  CCUCUU-C-UCC-UC-UGUGCUCUCGGUGA-GGAUGUAAGGGGUCA-UUUAAGAGAGCU
Hsp.gestii  CCUCUU-C-UCC-UC-UGUGCUCUCGGUGA-GGAUGUAAGGGGUCA-UUUAAGAGAGCU
Bb.brevis   GCUCUC-CCACU-GCAUCGGCCCGU-GUGC-CGUGGAUAGGGCUCAACUUUAACGGGCU
B.subtilis  GCUCUUC--CUG-ACAU-UGCCUAU-GUGU-CUGU-GAAGAGCACA-UCCAAGUAGGCU
B.badius    GCUCCU--CCCG-CUAU-CGUCCAU-GUAGUCGGGUAAGGGGUCCAAACUUAGUGGACU
B.megateri  GUUCCU--CCCU-CCAU-CGCCCAU-GUGGUAGGGUAAGGGACUCACUUUAAGUGGGCU
B.thermole  GCUCCUC--CCG-CCAU-CGCCCGC-GUGG-CGUUCGAGGGGCUCAUAUGGAGCGGGCU
Eco.fecium  GAUCCU--CUCG-GCAU-CGCCCAU-GUGCUCGAGUAAGGGUCUCAAAUUUAGUGGGAU
Eco.faecal  GAUCCU--CCCG-GCAU-CGCCCAU-GUGCUCGGGUCAGGGUCCUAAUCGAAGUGGGAU
Stc.pyogen  GACUUCU--ACA-AGAU-UGCUUGU-GUCC-UGUU-AGAAGUC-UCAAAAUAGCAAGCU
Stc.pneumo  GACCC--GAUUU-GGAU-UGCUCGU-GUUC-AAUGA-CAGGUCUUAUUAUUAGCGAGAU
Stc.gordon  GACCC--GAUUC-GGAU-UGCUUGU-GUCU-GAUGA-CAGGUCUUAUUAUUAGCAAGCU
Stc.mutans  GAUCAAU--AAC-AAAU-UGCUUGU-GUUU-GUUG-AUUGGUCUUAUUGUUAACAAGCU
Stp.epider  AUCGCC-UAACA-GCAU-CUCCUAC-GUGC-UGUUAACGCGAUUCAACCCUAGUAGGAU
Stp.aureus  AUCGCC-UAACA-GCAU-UUCCUAU-GUGC-UGUUAACGCGAUUCAACCUUAAUAGGAU
L.acidophi  UGCUCU-UUGUC-GGUU-UACUCGU-GGCU-GACAC-UGAGUAUCA-ACUUAGCGAGUU

                                   PK2
```

```
                                                              PK3
Tab.saccha  -AACUGAUUU-AUCAAAGCUUUGAGAU--AAAUCGGAUU----UUAUGAAGC-U
C.acetobut  AAACGAGCCU-UACAAAGCUUUGAGUA--AGGAACGGAA---UUUAUGAAGC-U
C.stercora  GAACCAGCCG-GAUCAGGCUUUCAGGUC--CGG-UGGGAU---UUAAUGAAGC-U
C.perfrige  AACCGAGCCU-AGCAAAGCUUUGAGCU--AGGAACGGAA---UUUAUGAAGCUU
C.lentocel  CCUUCAC-CU-GGCAAAGCUUUGAGCC--AACGUGAACA----CUAUGAAGC-U
Hlb.mobili  ---GGCUUCG-ACCAAUUCUCGGAGGU--CCAAGCGAGA---UUUAUCGAGA-U
Hsp.gestii  ---GGCUCGA-ACCAAUUCUCGGAGGU--UCGGGUAAGA---CUUAUCGAGA-U
Bb.brevis   -ACGCCGGAG-GCUUCCGCCUG-GAGC--CAAAGGAAGAAGACCAAUCAGGC-U
B.subtilis  -ACGCUUGCG-UUC-CCGUCUG-AGAA--CGUAAGAAGA-GAUGAA-CAGAC-U
B.badius    -ACGCCGGAG-UUCUCCGCCUG-GGGA--CAAAGGAAGA-GAUCAAUCAGGC-U
B.megateri  -ACGCCGGAG-UUCGCCGUCUG-AGGA--CGAAGGAAGA-GAAUAAUCAGAC-U
B.thermole  -ACGCCCAAA-UCCGCCGCCUG-AGGA--UGAGGGAAGA-GACGAAUCAGGC-U
Eco.fecium  -ACGUGACAA-CUUUCCGUCUG-UAAG--UUGUUAAAGA-GAU-CAUCAGAC-U
Eco.faecal  -ACGCUAAAU-UUUUCCGUCUG-UAAA--AUUUAGAGGA-GCU-UACCAGAC-U
Stc.pyogen  -ACGGUUACG-AAAU-UGUCUA-GUUU--CGUGACAAGA-GAUUGA-UAGAC-U
Stc.pneumo  -ACGAUUAAG-CC-U-UGUCUA-GCGG--UUUGAUAAGA-GAUUGA-UAGAC-U
Stc.gordon  -ACGGUAGAA-UC-U-UGUCUA-GUGA--UUUUACAAGA-GAUUGA-UAGAC-U
Stc.mutans  -ACGUUAGAA-CU-G-AGUCAG-GCUG--UUCUAAAAGA-GUUCUA-CUGAC-U
Stp.epider  -AUGCUAAAC-ACUGCCGCUUG-AAGUCUGUUUAGAUGAAAUAUAAUCAAGC-U
Stp.aureus  -AUGCUAAAC-ACUGCCGUUUG-AAGUCUGUUUAGAAGAAACUUAAUCAAAC-U
L.acidophi  -ACGUUUAAC-UACCUCACCUG-AAUA--GUUGAAAAGA-GUCUUAGCAGGU-U
                                                                        PK4
Tab.saccha  ACCAAAGCAGUU--AUCC-UG-UCA-CUGGGAG-AACUGCAGAGGGAAU--GUCAA-AACAG-UGA-C
C.acetobut  ACUGAAGUGAAA--AGCU-UG-UUU-GUAGGCG-UUUCAUGGAGGGAAU--GUUAA-AAUAC-AAA-C
C.stercora  ACCGACUUAUAA--AGCC-UG-UCU-CUGGGCG-UUAUAAGAAGGGAAU--GUCAA-AACAG-AGA-C
C.perfrige  ACCAA-AGAGGA--AGUU-UG-UCU-GUGGACG-UUCUCU-GAGGGAAU--UUUAA-AACACAAGA-C
C.lentocel  ACUAAAAUCUAG--AGCC-UG-UCU-UUGGGCG-CUAGAUGGAGGGAAU--GUCAA-AACAA-AGA-A
Hlb.mobili  AGCCUGACCAAC--GCUC-UG-UCU-GCCGUGC-GGAAGGAAGGCGAAA-UCUAAA-ACGAC-AGA-C
Hsp.gestii  AGCCUGACCAAC--GCUC-UG-UCU-GCCGUGC-GGAAGGAUGGCGAAA-UCUAAA-ACGAC-AGA-A
Bb.brevis   AGGUGCCAGGUC--AGCG-CG-UCA-CUCCGCG-AAUCUGUCACCGAAA-CUCUAA-ACGAG-UGA-C
B.subtilis  AGCUC-UCGGAA--GGCC-CG-CCC-GCAGGCA-AGAAGAUGAGUGAAACCAUAA-UAUGC-AGG-C
B.badius    AGCUG-CCCGGA--CGCC-CG-UCG-AUAGGCA-AAAGGAACAGUGAAC-CCCAA-UAUAU-CGA-C
B.megateri  AGCGA-CUGGGA--CGCC-UG-UUG-GUAGGCA-GAACAGCUCGCGAAU-GAUCAA-UAUGC-CAA-C
B.thermole  AGCCG-CCGGGA--GGCC-UG-UCG-GUAGGCG-GAACGGACGGCGAAG--CGAAA-UAUAC-CGA-C
Eco.fecium  AGCGAUACAGAA--UGCC-UG-UCA-CUCGGCA-AGCUGUAAAGCGAAA-CCACAA-AUGAGUUGA-C
Eco.faecal  AGCAAUACAGAA--UGCC-UG-UCA-CUCGGCA-CGCUGUAAAGCGAAC-CUUUAA-AUGAG-UGU-C
Stc.pyogen  CGCAAACUAAUG--GCU--UGAGUU-AUG-UGU-CUUUAGUUUGUUAAA---UGAA-GACAU-AAC-C
Stc.pneumo  CGCAGUUUCUAG--ACU--UGAGUU-AUG-UGU-CGAGGGGCUGUUAAA---AUAA-UACAU-AAC-C
Stc.gordon  CGCUUGAUUUGG--GCU--UGAGUU-AUG-UGU-CAAAAUCAAGUUAAA---ACAA-UACAU-AGC-C
Stc.mutans  CGCAUCGUUAGA--GUU--UGAGUU-AUG-UAU-UGUAACGGUGUUAAA---UAAA-CACAU-AAC-C
Stp.epider  AGUAUCAUGUU---GGU--UG-UUU-AUU-GCU-UAGCAUGAUGCGAAA---AUUA-UCAAU-AAA-C
Stp.aureus  AGCAUCAUGUU---GGU--UG-UUU-AUC-ACU-UUUCAUGAUGCGAAA---CCUA-UCGAU-AAA-C
L.acidophi  AGCUAGUCCAUACUAGCCCUG-UUA-UAUGGCGUUUUGGACUAGUGAAG--UUCAAGUAAUA-UAA-C

Tab.saccha  UGCGCUCGGAGAAGCUUUUACUG-UGACACCUUCGGACCGGGUUCAACUCCC*************  (3')
C.acetobut  UGCACUCGGAGAUGCUUAAAUGA-AACCAUUUUCGGACAGGGGUUCGAUUCCCCUCGCCUCCA***
C.stercora  UGCACCCGGAGAAGCUCUUGUGG-AUAUGGUUCCGGACACGAGUUCGAUUCCC*************
C.perfrige  UACACUCGUAGAAAGUCUUACUG-GUCUGCUUUCGGACACGGGUUCAACUCCC*************
C.lentocel  UAUGAUGGUAGAGACCACGCUAU-AUGGGCUUUCGGACAGGGGUUCGAUUCCC*************
Hlb.mobili  UACGCUCGUAGUGUCCUUUGUGG-GCAUUUCUUCGGACGCGGGUUCAACUCCC*************
Hsp.gestii  UACGCUCGUAGUGUCCUUUGUGG-GCAUUUCUUCGGACGCGGGUUCAACUCCC*************
Bb.brevis   UGCGCUCGGAGAUGCUCAUGUAU-CGCUGUUUUCGGACGGGGGUUCGAUUCCC*************
B.subtilis  UACGCUCGUAGACGCUUAAGUAAUCGAUGUUUCUGGACGUGGGUUCGACUCCCACCGUCUCCA***
B.badius    UACGCUCGUAGACGUUCAAGUGG-CGUUAUCUUUGGACGUGGGUUCAACUCCC*************
B.megateri  UACACUCGUAGACGCUUAAGUGG-CCAUAUUUCUGGACGUGG**************************
B.thermole  UACGCUCGUAGAUGCUUAAGUGG-CGAUGCCUCUGGACGUGGGUUCGAUUCCC*************
Eco.fecium  UAUGAACGUAGAUUUUUAAGUGG-CGAUGUGUUUGGACGCGGGUUCAACUCCC*************
Eco.faecal  UAUGAACGUAGAGAUUUAAGUGG-CAAUAUGUUUGGACGCGGGUUCGACUCCCGCCGUCUCCA***
Stc.pyogen  UAUGGACGUAGACAAAUAUGUUG-GCAGGUGUUUGGACGUGGGUUCGACUCCCACCAGCUCCA***
Stc.pneumo  UAUGGUUGUAGACAAAUAUGUUG-GCAGGUGUUUGGACGUGGGUUCGACUCCCACCGGCUCCA***
Stc.gordon  UAUGGUUGUAGACAAAUAUGUUG-GCAGAUGUUUGGACGUGGGUUCGACUCCCACCGGCUCCA***
Stc.mutans  UAUAGUUGUAGACAAAUGGGUUA-GCAGAUGUUUGGACGUGGGUUCGACUCCCACCGGCUCCA***
Stp.epider  UACACACGUAGAAAGAUUUGUAU-CAGGACCUCUGGACGCGGGUUCAACUCCC*************
Stp.aureus  UACACACGUAGAAAGAUGUGUAU-CAGGACCUUUGGACGCGGGUUCAAAUCCCGCCGUCUCCA***
L.acidophi  UAUGAUCGUAGAGGUCAGUGACG-AGAUGCGUUUGGACAGGGGUUCAACUCCC*************
                H2                H5                    H6          H1
```

FIG. 3C

+RNA-LIKE DOMAIN H1-H6

```
Aqf.aeolic  CG-GGCUACUCGGU--CGCACGGG-GCUGAGUAGCUGACACCUAACCCGUGCU
Tt.maritim  A--CCGAUUCAG--UUCGCCUUCCGGCCUGAAUCGGGAAAACUCAGGAAGGCU
Tt.neapoli  A--CCGAUCUGGGCUCCGCCUUCCGGCCCGGAUCGGGAAGGUUCAGGAAGGCU
T.thermoph  A--GCCCGGGGC--CACGCCCUCU--AACCCCGGGCGAAGCUUGAAGGGGGCU
D.radiodur  A--GCCC-AGGC--GAUUCUCCAU--AGCCGACGGCGAAACU-UUAUGGAGCU
D.proteoly  A--GCUU-AGGU--GAGGUUCCAU--AGCCAAAAGUGAAACC-AAAUGGAAAU
Tmc.roseum  GCCCCUGGCCCA--AGCGCCGGUG---CGGGCCAGGUCAAGCGUGAUCCGGCU   PK3
Ctb.proteo  GC-UCUUAAGCAG--UGGCACCAG--CUGUUUAAGGGUGAAAAGAGUGGUGCU
Her.aurant  CGCUCCCCUAGUU--AUGUCUGUG--GGCUAGGGG--CUAAGAUUAACAGGCU
Tdb.commun  UU-GGGAGGCUUAA-UCGGUGGGG-UUAAGCCUCCCGAGAUUACAUCCCACCU
Ver.spinos  G--GCCAAAAGAGC-GGGCGACCG-GC-CCCAAGGCGAGAUCUACAGGCCGCU
Dcg.thermo  GCCCCUUCCG-----ACUCCCCUA-----AGGAAGGGAAAGA-UGUAGGGGAU

Aqf.aeolic  A--CCCUC-GGGGAGCUUGCCCGUGGGCGACCC-GAGGG--GAAAUCC-UGAACACGGGC
Tt.maritim  G-UGGGAGAGGACACCCUGCCCGUGGGAGGUCC-CUCCC--GAGAGCG-AAAACACGGGC
Tt.neapoli  G-UGGGAAGCGACACCCUGCCCGUGGGGGGUC-CUUCCC--GAGACAC-GAAACACGGGC
T.thermoph  C-GCUCCUGGCC--GCCCGUCCGCGGGCCAAGCCAGGAG--GACACGC-GAAACGCGGAC
D.radiodur  A-CGGCCUGCGAGAACCUGCCCACUGGUGAGCGCCGGCCC-GACAAUC-AAACAGUGGGA
D.proteoly  A-AGGCGGACGGCAGCCUGUUUGCUGGCAGCCCAGGCCC--GACAAUU-UAAGAGCAGAC
Tmc.roseum  C-GGCUGACCGGGAUCCUGUCGGUGGGAGCCUGG-CAGC--GACAGUA--GAACACCGAC   PK4
Ctb.proteo  G--GGCAGUGCGGUU-GGGCU-UCCUGGGCUGCACUGUC--GAGACUU-CACAGGAGGGC
Her.aurant  G-GUCGUGGC-CCGCUUUGUCUAUCGGGUGGUGCACCGAU-AAGAUUU-AAUCAAUAGAC
Tdb.commun  G--GUAGGGUUGCUUGGUGCCUGUGACAAGCA-CCCUAC--GAGAUUU--UCCCACAGGC
Ver.spinos  G--GAUGGACGGCAUCCUGGCAGUAGGAGGCUGGACAUC--GAGAUCA--AAUNAUUGCC
Dcg.thermo  AGGUGCUUACAGAAUCCUGCGGGAGGGAGUCUGUAAGUGCCGAAAAGUUAAAACUCCCGC

Aqf.aeolic  UAAGCC-UGUAGAGCCUCGGAUGUGGCCGCCGUCCUCGGACGCGGGUUCGAUUCCCGCCGCCUCCACCA
Tt.maritim  UGCGCU-CGGAGAAGCCCAGGGG---CCUCCAUCUUCGGACGGGGGUUCGAAUCCCCCCGCCUCCACCA
Tt.neapoli  UGCGCU-CGGAGAAGCCCAGGGG---CCUCCAUCUUCGGACGGGGGUUCGAUUCCCGCCGCCUCCA***
T.thermoph  UACGCG-CGUAGAGGCcacgccc---cggcgaccuucggacgggggguucgauuccccccaccuccacca
D.radiodur  UACACA-CGUAGACGCA-CGCUG---GACGGACCUUUGGACGGCGGUUCGACUCCGCCCACCUCCACCA
D.proteoly  UACGCA-CGUAGAUGCA-CGCUG---GAUGGACCUUUGGACGGCGGUUCGAUUCCCGCCGCCU-CACCA
Tmc.roseum  UAAGCC-UGUAGCAUAUCCUCGG---CUGAACGCUCUGGACGGGGGUUCAACUCCCGCCAGCUCCACCA
Ctb.proteo  UAAGCC-UGUAGACGCGAAAGGU---GGCGGCUCGUCGGACGCGGGUUCGAUUCCCGCCGCCUCCACCA
Her.aurant  UACGCU-UGUAGAUGCUUGCGGU----UUAACUUUUUGGACGCGGGUUCGAUUCCCGCCGCCUCCACCA
Tdb.commun  UAAGCC-UGUAGCGGUUUAAUCU---GAACUAUCUCCGGACGCGGGUUCGAUUCCCGCCGCCUCCACCA
Ver.spinos  UGAGCA-UGGAGACGCUUUCAUA-----AAGGNGUUCGGACAGG**********************
Dcg.thermo  UAAGCU-UGUAGAGGCUUUUGAU---UCUUGCUCUCUGGACGCGGGUUCGAUUCCCGCCGCCUCCACCA   3'
               H2           H5                        H6           H1

                                           +RNA-LIKE DOMAIN H1-H6
```

FIG. 4B

```
                 H1                    H5              H2              PK1
         ⑤ 5'┌──────┐          ┌──────────────┐    ┌──────┐        ┌──────┐
Trp.pallid  GGGGAUGACU-AGGUUUCGACUAGGGAUGUG-GGGUGUUGCGCUGCAGGUGGAGUGUCGAUCUCCCGAU--UCGGCGCCUUU
Bor.burgdo  GGGGAUGUUU-UGGAUUUGACUGAAAAUGUUAAUAUUGUAAGUUGCAGGCAGAG--GGAAUCUCUUAAAACUUCUA----AA
Bor.qarini  GGGGCUGAUUCUGGAUUCGACUGAAAAUGCGAAUAUUGUAAGUUGCAGGCAGAG--GGAAUCUCUUAAAACUUCUA----AA
Bor.afzeli  GGGGCUGAUUCUGGAUUCGACUGAAAAUGCUAAUAUUGUAAGUUGCAAGCAGAG--GGAAUCUCUUAAAACUUCUA----AA
Bor.crocid  GGGGCUGAUUCUGGAUUCGACUAAGAACUUUAGUAGCAUAAAUGGCAAGCAGAG--UGAAUCUCUUAAAACUUCUU----UA
Bor.hermsi  GGGGCUGAUUCUGGAUUCGACUAAAAACUUUAGUAGCAUAAAUUGCAAGCAGAG--GGAAUCUCUUAAAACUUCUU----UA
                       CODING SEQUENCE ↓                                            ┌──H4
Trp.pallid  AUAACUgccaauucugacaguuuc---------gacuacgcgcucgccgcgUAA-----UCG
Bor.burgdo  AUAAAUgcaaaaaauaauaacuuuacaagcucaaaucuuguaauggcugcuUAAGUUAGCAG
Bor.qarini  AUAAAUgcaaaaaauaauaacuuuacaagcucaaaccuuguaauggcugcuUAACUUAGCAG
Bor.afzeli  AUAAAUgcaaaaaauaauaacuuuacaaguucaaaccuuguaauggcugcuUAAGUUAGCAG
Bor.crocid  AUAAAUgcaaaaaauaauaacuuuacaaguucagaucuuguaauggcugcuUAAUUUAGCAG
Bor.hermsi  AUAAAUgcaagaaauaauaacuuuacaaguucaaaucuuguaauggcugcuUAAAUUAGCAG

Trp.pallid  CGGGCCU-GUGUUUGCGCUGCUCUG-AGCGAACAUAUCGGCCCGAC-GCCAAACGGAGCU ⎫
Bor.burgdo  -AGGGUUUUGUUGAAUUUGGCUUUGAGGUUCA-CUUAUACUCUUUU-CGACAUCAAAGCU ⎪
Bor.qarini  -GGAGUUUCGUUGAAUUUGGCUUUGAGGUUCA-CUUAUACUCUUUU-CGAUAUCGAAGCU ⎬ PK2
Bor.afzeli  -AGAGUUUUGUUGAAUUUGGCUUUGAGAUUCA-CUUAUACUCUUUU-AGACAUCGAAGCU ⎪
Bor.crocid  -AGAGUUUUGUUGGAUUUGCUUUGAGGUUCAACUUAUACUCUUUA-AGACAUCAAAGUA ⎪
Bor.hermsi  -AGAGUUCUGCUGGAUUUUGCUUUGAGGUUCAGCUUAUACUCUUUUAAGACAUCAAAGCU ⎭

Trp.pallid  UGCUCUUACGUUG-UGCACGGCGGACGUAGGGGGACUUUUGUCUGUGCU ⎫
Bor.burgdo  UGCUUAAAAAUGUUUUCAAGUU-GAUUUUUAGGGACUUUUAUACUUGAG ⎪
Bor.qarini  UGCUUAAAAAUGUUUUCAAGUU-AAUUUUUAGGGACUUUUGUACUUGAG ⎬ PK3
Bor.afzeli  UGCUUAAAAAUGUUUUCAAGUU-GAUUUUUAGGGACUUUUAUACUUGAG ⎪
Bor.crocid  UGCCUAAAAAUGU-UUCAAGUU-GAUUUUUAGGGACCUUUUAAACUUGAG ⎪
Bor.hermsi  UGCUUAAAAAUAU-UUCAAGUU-GAUUUUUAGGGACUUUUAAAUUUGAG ⎭

Trp.pallid  AAGACUCUGGCGCG-UGCGGUGCAGGCCUAGCAGAGUCCGACAAACGCAGUACGCACCGC ⎫
Bor.burgdo  AGCAAUUUGGUGGUUUUGCUAGUAUUUCCAAACCAUAUUGCU---U-AAUAAAAUACUAGA ⎪
Bor.qarini  AGCAAUUUGGCGGUUUUGCUAGUAUUUCCAAACCAUAUUGCU---UAAGUAAAAUGCUAGA ⎬ PK4
Bor.afzeli  AGCAAUUUGGCGGUUUUGCUAGUAUUUCCAAACCAUAUUGCU---U-AGUAAAAUACUAGA ⎪
Bor.crocid  AGUAAUUUGGUGGUUUUGCUUGUUUUU-CCAAGCCUUAUUGCU---UUUUCUAAAAAUAGC ⎪
Bor.hermsi  AGUAAUUUGGCGGUUUUGCUAGUUUUUCCAAACCUUAUUACU---UAAAGAAAACACUAGC ⎭

Trp.pallid  UAAACCUGUAGGCGCGCAGCACUCG-CUCUUUAGGACGGGGUUCGAUUCCCCCCAUCUCCACca
Bor.burgdo  UAAGCUUGUAGAAGCUUAUAGUAUU-AUUUUUAGGACGCGGGUUCAAUUCCCGCCAUCUCCACca
Bor.qarini  UAAGCUUGUAGAAGCUUAUAAUAUU-GUUUUUAGGACGCGGGUUCAauucccgccaucuccacca
Bor.afzeli  UAAGCUUGUAGAAGCUUAUAGUAUU-GUUUUUAGGACGCGGGUUCAauucccgccaucuccacca
Bor.crocid  UAAGCUUGUAGAUAUUUAUGAUAUU-AUUUUUGGACGCGGGUUCAauucccgccaucuccacca
Bor.hermsi  UAAGCUUGUAGAUAUUUAUGAUAUU-AUUUUUAGGACGCGGGUUCAauucccgccaucuccacca ③ 3'
                  H2              H5              H6       H1
```

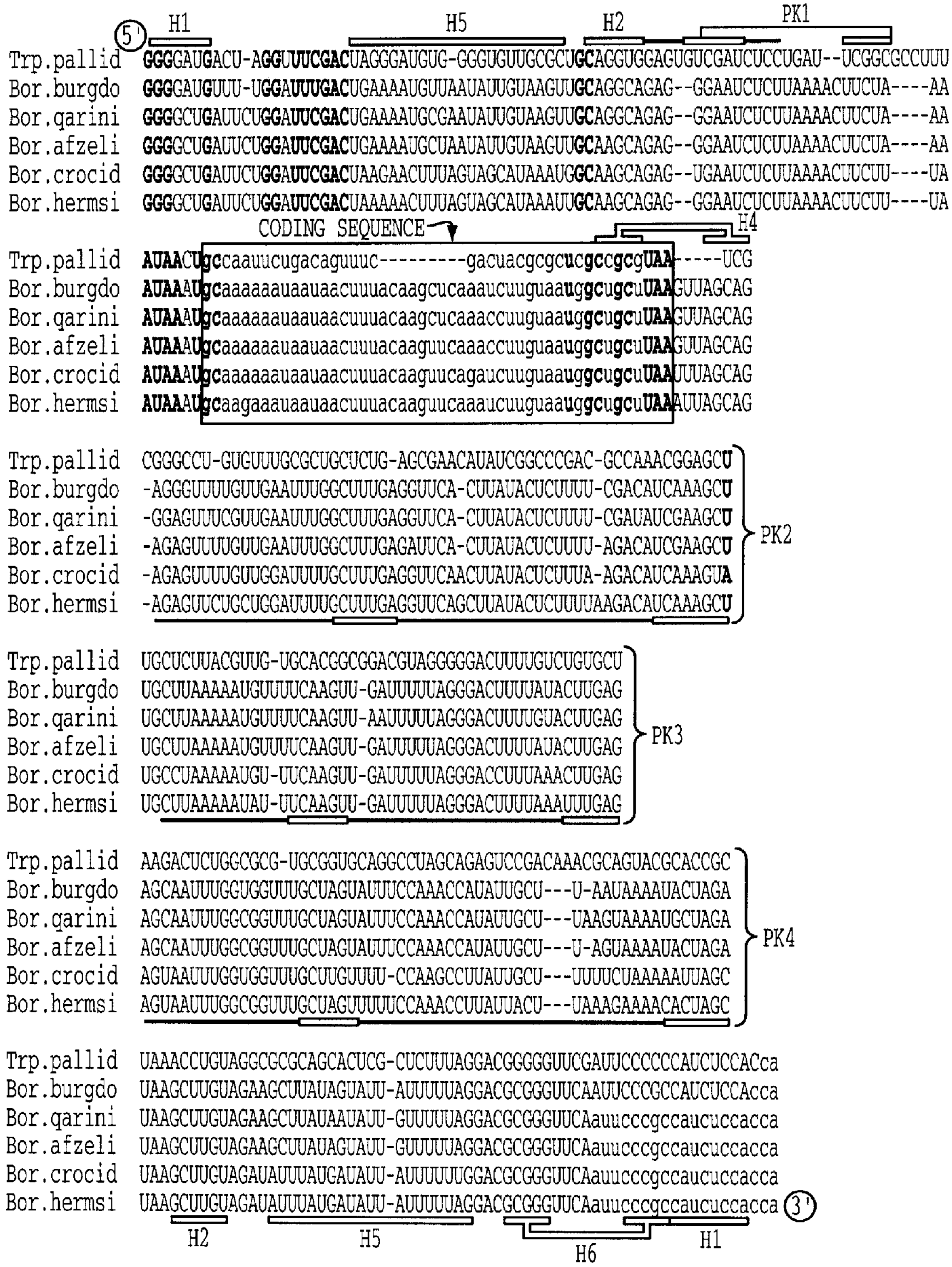

FIG. 8B

```
Alc.faecal  GCAGUGUUAU-UUACAAAGAAU--C-GAAUCGGUCUGCGCCACGAAGUCCGGUUCUAAAA-CUUAGUGGAU
Alc.eutrop  GCGAGGUCAU-UUACGUCAGAU--A-AGCUCCGGAAGGGUCACGAAGCCGGGGACGAAAA-CCUAGUGACU
Ral.picket  GCGAGGUCAU-UUACGUCAGAU--A-AGCUUUAGGUGAGUCACGGGCCUAGAGACGAAAA-CUUAGUGAAU
Nis.gonorr  GCAACGUCAUCUUACAUUGACU--G-GUUUCCAGCCGGGUUACUUGGCAGGAAAUAAGACUUAAGGUAACU
Nis.meninS  GCAACGUCAUCUUACAUUGACU--G-GUUUCCUGCCGGGUUAUUUGGCAGGAAAUGAGAUUUAAGGUAACU
Chb.violac  GUAGUGUCACUCUACAUCUGCU--A-GUGCUGUUCCGGGUUACUUGGUUCAGUGCGAAAUAAUAGGUAACU   PK3
Nms.cryoto  GCAGAGUCAU-UAG-CAAGGAU--C-GCGUUCUGUAGGGUCACUUUACAGAACGUUAAACAAUAGGUGACU
Mtb.glycog  GCAGCGUCAU-UAAGAGAGGAU--C-GUGCGAUAUUGGGUUACUUAAUAUCGUAUUAAAUCCAAGGUAACU
Ps.testost  GCAAGGGAAU-UUUCAUUAGCU--G-GCUGGAUACCGGGCUUCUUGGUAUUUGGCGAGAUUUUAGGAAGCU
Vx.paradox  GCAAGGAUAA-CUACAUGGGCU--G-GCUCCGAUCCGGGUACCUUGGGUCGGGGCGAGAAAAUAGGGUACU
Hph.paller  GCAAGGUAAU-UUACAUCGGCU--G-GUUCUGCGUCGGGCACCUUGGCGCAGGAUGAGAUUCAAGGAUGCU
Brd.pertus  GCAGCGACAU-UCACAAGGAAU--CGGCCACCGCUGGGGUCACA-CGGCGUUGGUUUAAA-UUACGUGAAU
                   PK2

Alc.faecal  CGCCAAGG-AAAGGCCUGUCA-AUUGGCAUAGUCCAAGGUUAAAACUUAAAAUUAAU-UGAC
Alc.eutrop  CGCCGUCG-UAGAGCGUGUUC-GUCCGCGAUG-CGCCGGUUAAAU---CAAA-UGACAGAAC
Ral.picket  CGCCGUCG-UAGAGCGUGUUC-GUCCGCGAUG-CGGCGGUUAAAU---CAAA-UGACAGAAC
Nis.gonorr  GGUUUCCA-AAAGGCCUGUUG-GUCGGCAUGA-UGGAAAUAAGAUUUUCAAAUAGACACAAC
Nis.meninS  GGUUUCCA-AAAGGCCUGUUG-GUCGGCAUGA-UGGAAAUAAGAUUUUCAAAUAGACACAAC
Chb.violac  CGCCAAAGUCCA-GCCUGUCC-GUCGGCGUGG-CAGAGGUUAAAUC--CAAA-UGACACGAC
Nms.cryoto  CGCCUGCC-AUCAGCCCGCCA-GCUGGCGGUU-GUCAGGUUAAAU---UAAA-GAGCAUGGC   PK4
Mtb.glycog  CGCCUGCU-GUUUGCUUGCUC-GUUGGUGAGC-AUCAGGUUAAAU---CAAA-CAACACAGC
Ps.testost  GGCUACCCAAGCAGCGUGUGC-CUGCGGGGUUUGGGUGGCGAGAUU--UAAA-ACAGAGCAC
Vx.paradox  GGCGUCCGGUUUAGCGUGUGA-CUGCGCGACUCCGGAAGCGACACU--CAAA-ACAGAUCAC
Hph.paller  GGCUUCCCGUUUAGCGUGCCA-CUGCGCGACUCGGGCGGCGAGACC--CAAA-UCAGACGGC
Brd.pertus  CGCCCUGG-UCCGGCCCGUCG-AUCGGCUAAGUCCAGGGUUAAAUC--CAAAUAGAU-CGAC

Alc.faecal  UACACAUGUAGAACUGUCUGUGGACGGCUUGCGGACGGGGGUUCGAUUCCC*************
Alc.eutrop  UAAGUAUGUAGAACUCUCUGUGGAGGGCUUACGGACGCGGGUUCGAUUCCCGCCGGCUCCACCA
Ral.picket  UAAGUAUGUAGAACUCUCUGUGGAGGGCUUGCGGACGCGGGUUCGAUUCCC*************
Nis.gonorr  UAAGUAUGUAGAACGCUUUGUAGAGGACUUUCGGACGGGGGUUCGAUUCCCCCCGCCUCCACCA
Nis.meninS  UAAGUAUGUAGAACGCUUUGUAGAGGACUUUCGGACGGGGGUUCGAUUCCCCCCGCCUCCACCA
Chb.violac  UAAGUAUGUAGAACUCACUGUAGAGGACUUUCGGACGCGGGUUCAACUCCC*************
Nms.cryoto  UAAGUAUGUAGAACUGUCUGUAGAGGACUUGCGGACGCGGGUUCAACUCCC*************
Mtb.glycog  UAAGUAUGUAGAACUGUCUGUGGAGGGCUUGCGGACGGGGGUUCGAUUCCC*************
Ps.testost  UAAACAUGUAGAUCUGUCCGGCGAAGGCUUACGGACGCGGGUUCAAUUCCCGCCGGCUCCA***
Vx.paradox  UAAACAUGUAGAACUGCGCGAUGAAGGCUUGCGGACGGGGGUUCAACUCCC*************
Hph.paller  UACACAUGUAGAACUGCUCGAAAAAGGCUUGCGGACGGGGGUUCAACUCCC*************
Brd.pertus  UAAGCAUGUAGAACUGGUUGCGGAGGGCUUGCGGACGGGGGUUCAAUUCCCCCCGGCUCCACCA  3'
                H2          H5                 H6          H1
```

FIG. 9B

```
              H1                    H5              H2
        ⑤'   ═══                ══════════════   ═════
Leg.pneumo  ******************CGUGGGUUGCAAAACCGGAAGUGCAUGC
Chr.vinosu  ******************CGUGGGUCGCGAAACCUAAGGUGCAUGC
Dcb.nodosu  ****************************CUCGAGGUGCAUGU
Ps.aerugin  GGGGCCGAUU-AGGAUUCGACGCCGGUAACAAAACUUGAGGGGCAUGC
Ps.fluores  ******************CGCCGGUUGCGAACCUUUAGGUGCAUGC
Mar.hydroc  ******************CGCCGGUGACGAACCCUUGGGUGCAUGC
Shw.putref  GGGGGCGAUUCUGGAUUCGACAGGAUUCACGAAACCCUGGGAGCAUGC
Psm.halopl  ******************CGGAAUUCAAGAAGCCCGAGGUGCAUGU
Ae.salmoni  ******************CAAGAUUCACGAAACCCAAGGUGCAUGC
S.typhimur  GGGGCUGAUUCUGGAUUCGACGGGAUUUGCGAAACCCAAGGUGCAUGC
E.coli      GGGGCUGAUUCUGGAUUCGACGGGAUUUGCGAAACCCAAGGUGCAUGC
Yer.pestis  GGGGCUGAUUCUGGAUUCGACGGGAUUCGCGAAACCCAAGGUGCAUGC
V.cholerae  GGGGCUGAUUCAGGAUUCGACGGGAAUUUUGCAGUCUGAGGUGCAUGC
H.influenz  GGGGCUGAUUCUGGAUUCGACGGGAUUAGCGAAGCCCAAGGUGCACGU
H.actinomy  GGGGCUGAUUCUGGAUUCGACGGGAUUAGCGAAGCCCGAAGUGCACGU
                              PK1
                        ═══════════════
Leg.pneumo  CGAG-AAGGAGAUC-UCUCGUAAAUA-AGA-CUCAAUUA-AAU
Chr.vinosu  CGAG-GUGCGGUUGACCUCGUAAAAC--CCUCCGCAAA--CUU
Dcb.nodosu  CGAG-AAUGAGAGAAUCUCGUUAAAU--ACUUUCAAAA--CUU
Ps.aerugin  CGAGCUGGUAGCAGAACUCGUAAAUUCGCUGCUGCAAA--CUU
Ps.fluores  CGAGUUGGUAACAGAACUCGUAAAUCCACUGUUGCAACUUUCU
Mar.hydroc  CGAGAUGGCAGCGAAUCUCGUAAAUCCAAAGCUGCAAC--GUA
Shw.putref  CGAG-GGGCGGUUGGCCUCGUAAA----AAGCCGCAAA--GUU
Psm.halopl  CGAG-GUGCGGUUUGCCUCGUAAAA---AAGCCGCAAUU-UAA
Ae.salmoni  CGAG-GUGCGGUAGGCCUCGUUAAC---AAACCGCAAA--AAA
S.typhimur  CGAG-GGGCGGUUGGCCUCGUAAA----AAGCCGCAAA--AAA
E.coli      CGAG-GGGCGGUUGGCCUCGUAAA----AAGCCGCAAA---AA
Yer.pestis  CGAG-GUGCGGUG-GCCUCGUAAA----AAACCGCAAA-AAAA
V.cholerae  CGAG-GUGCGGUAGGCCUCGUUAAC---AAACCGCAAA--AAA
H.influenz  CGAG-GUGCGGUAGGCCUCGUAAAU---AAACCGCAAA--AAA
H.actinomy  CGAG-GUGCGGUAGGCCUCGUAAAU---AAACCGCAAA--AAA
                                              CODING SEQUENCE
                                                    ↓
Leg.pneumo  A-UAAAU|gcaaacgaugaaaacuuugcugguggggaagcuaucgcugcc|UAA-----UAAGCACUUU
Chr.vinosu  A-UAGUU|gccaacgacgacaacuac-----------gcucucgcugcu|UAA-----UCCCAGCGGG
Dcb.nodosu  A-UAGUU|gcaaacgacgacaacuac-----------gcuuuagcggcu|UAA-----UUCCCGCUUU
Ps.aerugin  A-UAGUU|gccaacgacgacaacuac-----------gcucuagcugcu|UAA-----UGCGGCUAG
Ps.fluores  A-UAGUU|gccaaugacgaaaccuac---ggggaauacgcucucgcugcg|UAA-------GCAGCCUU
Mar.hydroc  A-UAGUC|gcaaacgacgaaaacuac-----------gcacuggcggcg|UAA---GCCGUU-CCAGU
Shw.putref  A-UAGUU|gcaaacgacgauaacuac-----------gcucuagccgcu|UAA-----UGCCGCUAG
Psm.halopl  AGUAAU|Cgcaaacgacgauaacuac-----------ucucuagcagcu|UAG-----GCUGGCUAG
Ae.salmoni  A-UAGUC|gcaaacgacgaaaacuac-----------gcacuagcagcu|UAAUAACCUGCAUAGAGC
S.typhimur  A-UAGUC|gcaaacgacgaaaccuac-----------gcuuuagcagcu|UAAUAACCUGCUUAGAGC
E.coli      A-UAGUC|gcaaacgacgaaaacuac-----------gcuuuagcagcu|UAAUAACCUGCUUAGAGC
Yer.pestis  A-UAGUU|gcaaacgacgaaaacuac-----------gcacuagcagcu|UAAUAACCUGCUUAGAGC
V.cholerae  A-UAGUC|gcaaacgacgaaaacuac-----------gcacuagcagcu|UAACCCUGCUCAGAGC
H.influenz  A-UACUC|gcaaacgacgaacaauac-----------gcuuuagcagcu|UAAUAACCUGCAUUUAGC
H.actinomy  A-UAGUC|gcaaacgacgaacaauac-----------gcuuuagcagcu|UAAUAACCUGCCUUUAGC
                                                                    H4
```

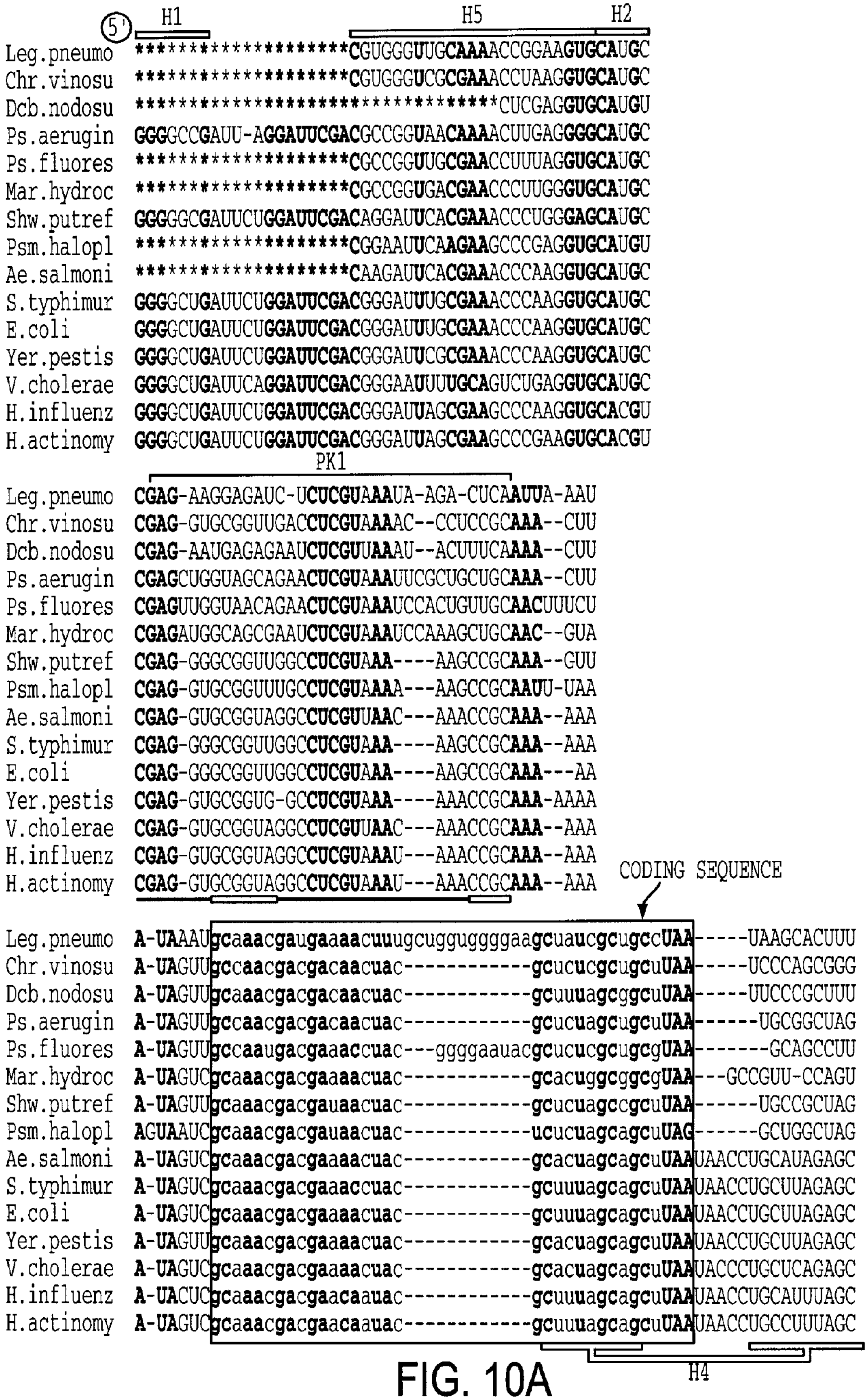

FIG. 10A

```
Leg.pneumo  AGUUAAACCAUCACUGUGUACUGGCCAAUAAACCCAGUAUC
Chr.vinosu
Dcb.nodosu
Ps.aerugin
Ps.fluores  AGCCCUUCCCUCCUGGUACCUUCGGGUCCAG
Mar.hydroc
Shw.putref
Psm.halopl
Ae.salmoni
S.typhimur
E.coli
Yer.pestis
V.cholerae
H.influenz
H.actinomy

Leg.pneumo  CCGUUCG-ACCGAGCCC--GCUUAUC-GGUAUCGAA-------UCAACGGUCAU-AAGAGAU-AAGCU
Chr.vinosu  CCUCUGA-CCGUCACUU--GCCUGUGGGCGGCGGAUU------CCAGGGGUAAC-CUCACAC-AGGAU
Dcb.nodosu  CGCUUAC-CUAGAUUU---GUCUGUGGGUUUACC---------GUAAGCGACAU--UAACAC-AGAAU
Ps.aerugin  CAGUCGC-UAGGGGAU---GCCUGUAAACCCGAAA--------CGACUGUCAG-AUAGAAC-AGGAU
Ps.fluores  CAAUCAU-CAGGGGAU---GUCUGUAAACCCAAAG--------UGAUUGUCAU-AUAGAAC-AGAAU
Mar.hydroc  CGUCCUG-GCUGAGGC---GCCUAUAACUCAGUAGCAACAUCCCAGGACGUCAU-CGCUUAU-AGGCU
Shw.putref  CCAUCUA-CCACACGCUUUGCACAUGGGCAGUGGAUU------UGAUGGUCAU-CUCACAUCGUGCU
Psm.halopl  CGCUCCU-UCCAUGUAU--UCUUGUG-GACUGGAUUUU-----GGAGUGUCACCCUAACAC-CUGAU
Ae.salmoni  CCUUCUA-CCCUAGCUU--GCCUGUGUCCUAGGGAAUC-----GGAAGGUCAU-CCUUCAC-AGGAU
S.typhimur  CCUCUCU-CCCUAGCCUCCGCUCUUAGGACGGGGAUCA-----AGAGAGGUCAAACCCAAAA-GAGAU
E.coli      CCUCUCU-CCCUAGCCUCCGCUCUUAGGACGGGGAUCA-----AGAGAGGUCAAACCCAAAA-GAGAU
Yer.pestis  CCUCUCU-CCCUAGCCUCCGCUCUUAGGACGGGGAUCA-----AGAGAGGUCAAACCUAAAA-GAGCU
V.cholerae  CCUUCCU-CCCUAGCUUCCGCUUGUAAGACGGGGAAAUC----AGGAAGGUCAAACCAAAUC-AAGCU
H.influenz  CUUCGCG-CUCCAGCUUCCGCUCGUAAGACGGGGAUAA-----CGCGGAGUCAAACCAAAAC-GAGAU
H.actinomy  CUUCGCU-CCCCAGCUUCCGCUCGUAAGACGGGGAUAA-----AGCGGAGUCAAACCAAAAC-GAGAU
                                                              PK2
```

```
Leg.pneumo  -AGCG-UCCU-AAUCU--AUCCC-GGGUU-AUGG-CGCGAAA-CU-CA--GGGAAU
Chr.vinosu  -CGUG-GUGA-CGGGA--GUCCG-GACCU-GAUC-CACUAAAACC-UA-ACGGAAU
Dcb.nodosu  -CGCU-GGUU-AACG--CGUCCGC-UGUU-AAUC-GGUUAAA-UU-AA-GCGGAAU
Ps.aerugin  -CGCC-GCCA-AGUU--CGCUGUA-GACG-UAAC-GGCUAAAACU-CA-UACAGCU
Ps.fluores  -CGCC-GUGC-AGUA--CGUUGUG-GACG-AAGC-GGCUAAAACU-UA-CACAACU
Mar.hydroc  GCUCC-GUUC-ACCAG-AGCUCA-CUGGU-GUUC-GGCUAAG-AU-UA-AAGAGCU
Shw.putref  -AGCGAGGGA-ACCC--UGUCUGG-GGGU-GAAC-CGCGAAACAG-UA-CCGGACU
Psm.halopl  -CGCGACGGA-AACCC-UGGCCG-GGGUU-GAAG-CGUUAAAACU-AA-GCGGCCU
Ae.salmoni  -CGUG-UGGA-AGUCC-UGCUCG-GGGCG-GAAG-CAUUAAAACC-AA-UCGAGCU
S.typhimur  -CGCG-CGGA-UGCCC-UGCCUG-GGGUU-GAAG-CGUUAAAACG-AA-UCAGGCU
E.coli      -CGCG-UGGA-AGCCC-UGCCUG-GGGUU-GAAG-CGUUAAAACUUAA-UCAGGCU
Yer.pestis  -CGUG-UGGA-AACCU-UGCCUG-GGGUG-GAAG-CAUUAAAACU-AA-UCAGGAU
V.cholerae  -GGCG-UGGA-UUCCCCCACCUGA-GGGAUGAAG-CGCGAGAUCU-AAUUCAGGUU
H.influenz  -CGUG-UGGA-AGCCACCGUUUGA-GGAUCGAAG-CACUAAAUUG-AA-UCAAACU
H.actinomy  -CGUG-UGGA-AGCCACCGUUUGA-GGAUCGAAG-CAUUAAAUUA-AA-UCAAAGU

Leg.pneumo  CGCUGUGUAU-CAUCCUGCCC-GUCGGAGGAGCCACAGUUAAAUUCAAAAGACAAGGC--
Chr.vinosu  CGCCGACUGAUCGCCCUGCCC-UUCGGGCGGCAGAAGGCUAAAAACAAUAGAGUGGGC--
Dcb.nodosu  CGCUUGUAAA-AUGCCUGAGC-GUUGGCUGUUUAUGAGUUAAACCUAAUUAACUGCUC--
Ps.aerugin  CGCUCCAAGC--ACCCUGCCA-CUCGGGCGGCGCGGAGUUAA-CUCAGUAGAGCUGGC--
Ps.fluores  CGCCCAAAGC--ACCCUGCCC-GUCGGGUCGCUGAGGGUUAA-CUUAAUAGACACGGC--
Mar.hydroc  CGCCUCUUGC--ACCCUGACC-UUCGGGUCGCUUGAGGUUAA-AUCAAUAGAA-GGACAC
Shw.putref  CACCGUGUGG-GAUCCUGUCU-UUCGGAGUUCAAACGGUUAA-ACAAUA-GAA-AGAC--
Psm.halopl  CGCCUUUAUC-UACCGUGUUU-GUCCGGGAUUUAAAGGUUAA-UUAAAU-GACAAUAC--   PK4
Ae.salmoni  AGUCAAUUCG-UGGCGUGUCU-CUCCGCAGCGGGUUGGCGAA-UGUAAA-GAG-UGAC--
S.typhimur  AGUCUGGUAG-UGGCGUGUCC-GUCCGCAGGUGCCAGGCGAA-UGUAAA-GAC-UGAC--
E.coli      AGUUUGUUAG-UGGCGUGUCC-GUCCGCAGCUGGCAAGCGAA-UGUAAA-GAC-UGAC--
Yer.pestis  AGUUUGUCAG-UAGCGUGUCC-AUCCGCAGCUGGCCGGCGAA-UGUAAU-GAUUGGAC--
V.cholerae  AGCCAUUCGU-UAGCGUGUCG-GUUCGCAGGCG-GUGGUGAA-AUUAAA-GAU-CGAC--
H.influenz  AGCUUAAGUU-UAGCGUGUCU-GUCCGCA-UGCUUAAGUGAA-AUUAAA-GACGAGAC--
H.actinomy  AGCUUAAUUG-UCGCGUGUCC-GUCAGCA-GGAUUAAGUGAA-UUUAAA-GACCGGAC--

Leg.pneumo  UAUGCAUGUAGAGCUAAAGGCAGAGGACUUGCGGACGCGG************************
Chr.vinosu  UAAGCAUGUAGGACCGAGGGCAGAGGGCUUGCGGACGCGG************************
Dcb.nodosu  UAAACAUGUAGUACCAAAAGUUAAGGAUUCGCGGACGGGGUUCAAAUCCCCCCGCCUCCACCA
Ps.aerugin  UAAGCAUGUAGAACCGAUAGCGGAGAGCUGGCGGACGGGGGUUCAAAUCCCCCCGGCUCCACCA
Ps.fluores  UACGCAUGUAGUACCGACAGCAGAGUACUGGCGGACGGGG************************
Mar.hydroc  UAAGCAUGUAGACCUCAAGGCCUAGUGCUGGCGGACGCGG************************
Shw.putref  UAAGCAUGUAGCGCCUUGGAUGUAGGUUUUCUGGACGCGGGUUCAAGUCCCGCCGCCUCCACCA
Psm.halopl  UAAACAUGUAGUACCGACGGUCGAGGCUUUUCGGACGGGG************************
Ae.salmoni  UAAGCAUGUAGUACCGAGGAUGUAGUAAUUUUGGACGGGG************************
S.typhimur  UAAGCAUGUAGUACCGAGGAUGUAGGAAUUUCGGACGCGGGUUCAACUCCCGCCAGCUCCACCA
E.coli      UAAGCAUGUAGUACCGAGGAUGUAGGAAUUUCGGACGCGGGUUCAACUCCCGCCAGCUCCACCA
Yer.pestis  UAAGCAUGUAGUGCCGACGGUGUAGUAAUUUCGGACGGGGGUUCAAAUCCCCCCAGCUCCACCA
V.cholerae  UAAGCAUGUAGUACCAAAGAUGAAUGGUUUUCGGACGGGGGUUCAACUCCCCCCAGCUCCACCA
H.influenz  UAAACGUGUAGUACUGAAGGUAGAGUAAUUUCGGACGGGGGUUCAACUCCCCCCAGCUCCACCA
H.actinomy  UAAACGUGUAGUGCUAACGGCAGAGGAAUUUCGGACGGGGGUUCAACUCCCCCCAGCUCCACCA (3')

            H2          H5          H6          H1
```

EUBACTERIAL TMRNA SEQUENCES AND USES THEREOF

CROSS-REFERENCE TO RELATED APPLICATIONS

The present application is division of U.S. patent application Ser. No. 11/329,230 filed on 11 Jan. 2006, which in turn in a division of U.S. patent application Ser. No. 09/958,206 filed on 20 Feb. 2002, now U.S. Pat. No. 7,115,366, which in turn is a national stage filing under 35 U.S.C. §371 of International patent application No. PCT/US00/08988 filed on 6 Apr. 2000, which in turn is related to and claims priority under 35 U.S.C. §119(e) to U.S. provisional patent application Ser. No. 60/128,058 filed on 7 Apr. 1999. Each of these applications is incorporated herein by reference.

This application was made with Government support under Grant No. GM 48152, funded by the National Institutes of Health, Bethesda, Md. The Government has certain rights in this invention.

BACKGROUND OF THE INVENTION

The present invention is directed to eubacterial tmDNA sequences and the corresponding tmRNA sequences. The present invention is further directed to alignments of eubacterial tmDNA sequences and use of the sequences and sequence alignments for the development of antibacterial drugs. The present invention is also directed to the use of the sequences for the development of diagnostic assays.

The publications and other materials used herein to illuminate the background of the invention or provide additional details respecting the practice are incorporated by reference, and for convenience are respectively grouped in the appended List of References.

Eubacterial tmRNAs (10Sa RNAs) are unique since they function, at least in *E. coli*, both as tRNA and as mRNA (for a review, see Muto et al., 1998). These ≈360±10% nucleotide RNAs are charged with alanine at their 3'-ends (Komine et al., 1994; Ushida et al., 1994) and also have a short reading frame coding for 9 to 27 amino acids depending on the bacterial species. *E. coli* tmRNA mediates recycling of ribosomes stalled at the end of terminatorless mRNAs, via a trans-translation process (Tu et al., 1995; Keiler et al., 1996; Himeno et al., 1997). In *E. coli*, this amino acid tag is co-translationally added to polypeptides synthesized from mRNAs lacking a termination codon, and the added 11 amino acid C-terminal tag makes the protein a target for specific proteolysis (Keiler et al., 1996).

Structural analyses based on phylogenetic (Felden, et al., 1996; Williams and Bartel, 1996) and probing (Felden et al., 1997; Hickerson et al., 1998) data have led to a compact secondary structure model encompassing 6 helices and 4 pseudoknots. tmRNAs have some structural similarities with canonical tRNAs, especially with tRNA acceptor branches. *E. coli* tmRNA contains two modified nucleosides, 5-methyluridine and pseudouridine, located in the tRNA-like domain of the molecule, in a seven-nucleotide loop mimicking the conserved sequence of T loops in canonical tRNAs (Felden et al., 1998).

Fifty-three tmRNA sequences are now known from both experimental data and Blast searches on sequenced genomes (summarized in Williams, 1999; Wower and Zwieb, 1999). These sequences cover only 10 phyla, less than one third of the known bacterial taxa. It is desired to determine additional tmRNA sequences and to use the tmRNA sequences for drug development.

SUMMARY OF THE INVENTION

The present invention relates to eubacterial tmDNA sequences and the corresponding tmRNA sequences. The present invention further relates to alignments of eubacterial tmDNA sequences and use of the sequences and sequence alignments for the development of antibacterial drugs.

In one aspect of the present invention, an extensive phylogenetic analysis was performed. Fifty-eight new tmDNA sequences including members from nine additional phyla were determined. Remarkably, tmDNA sequences could be amplified from all species tested apart from those in the alpha-Proteobacteria. This aspect of the invention allowed a more systematical study of the structure and overall distribution of tmRNA within eubacteria In a second aspect of the invention, alignments are made with the newly isolated tmDNA sequences and previously disclosed tmRNA sequences.

In a third aspect of the invention, the alignments of the tmRNA sequences allow the identification of targets for development of antibacterial drugs.

In a fourth aspect of the invention, the novel tmDNA or tmRNA sequences of the present invention are used to develop diagnostic assays, such as amplification-based assays, for the bacterial species disclosed herein.

BRIEF DESCRIPTION OF THE FIGURES

FIGS. 3A, 3B and 3C show the sequence alignment, structural domains and structural features for the tmRNA of several species of Firmicutes. The tmRNA sequences are set forth in SEQ ID NOs:67-87.

FIGS. 4A and 4B show the sequence alignment, structural domains and structural features for the tmRNA of several species of Thermophiles. The tmRNA sequences are set forth in SEQ ID NOs:88-99.

FIGS. 7A-1, 7A-2, 7B, 7C and 7D show the sequence alignment, structural domains and structural features for the tmRNA of several species of Mesophiles (7A-1, 7A-2, 7C, 7D) and environmental sludge (7B). The tmRNA sequences of the Mesophiles are set forth in SEQ ID NOs:118-123 and 125-128, and the tmRNA sequence of the environmental sludge is set forth in SEQ ID NO:124. The tmRNA sequences of several species of Clamydia are set forth in SEQ ID NOs: 129-131.

FIGS. 8A and 8B show the sequence alignment, structural domains and structural features for the tmRNA of several species of Actinobacteries (8A) and Spirochaetes (8B). The tmRNA sequences of the Actinobacteries are set forth in SEQ ID NOs:132-136, and the tmRNA sequences of the Spirochaetes are set forth in SEQ ID NOs:137-142.

FIGS. 9A and 9B show the sequence alignment, structural domains and structural features for the tmRNA of several species of Pourpres beta. The tmRNA sequences are set forth in SEQ ID NOs:143-154.

FIGS. 10A, 10B and 10C show the sequence alignment, structural domains and structural features for the tmRNA of several species of Pourpres gamma. The tmRNA sequences are set forth in SEQ ID NOs:155-169.

DETAILED DESCRIPTION OF THE INVENTION

Figure 1A:
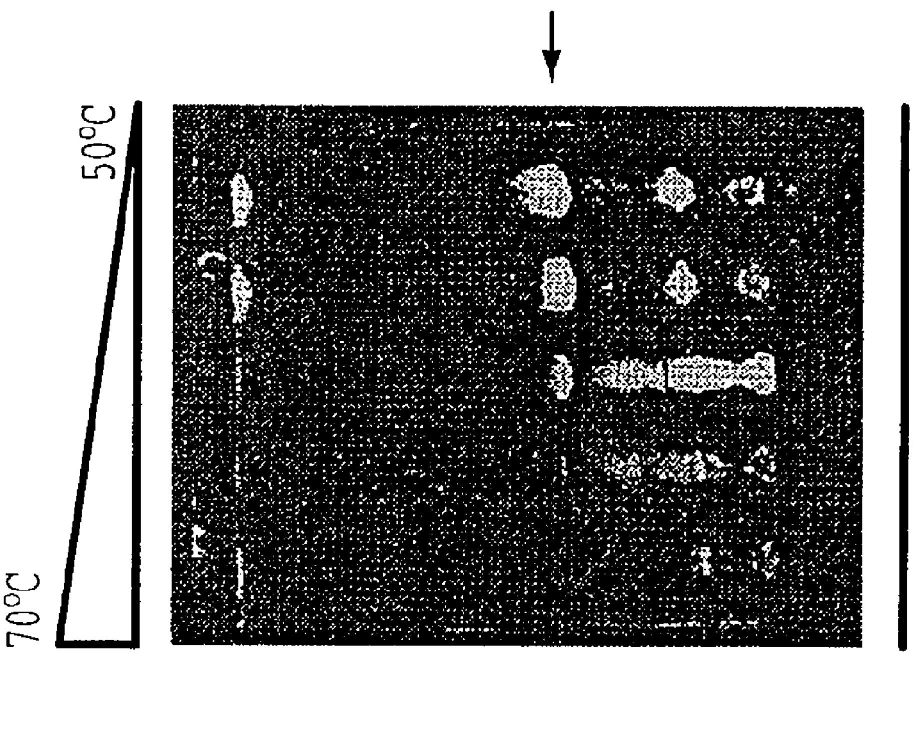
FIGS. 1A-1B show the effect of the annealing temperature (FIG. 1A) and magnesium concentration (FIG. 1B) on amplifying eubacterial tmRNA genes from genomic DNAs using PCR. A: Varying the annealing temperature from 50° to 70° C. during the PCR amplification of *Thermus aquaticus* (1). B; Varying the magnesium concentration to amplify tmDNA genes from *Thermus aquaticus* (1), negative effect of increasing the magnesium concentration), *Acholeplasma laidlawii* (2), positive effect of increasing the magnesium concentration, the upper band is the tmDNA gene) and from *Mycoplasma salivarium* (3), no discernible effect of magnesium ions in that concentration range). The arrows point toward the 4 novel tmDNA genes that have been sequenced.

The present invention is directed to eubacterial tmDNA sequences and the corresponding tmRNA sequences. The present invention is further directed to alignments of eubacterial tmDNA sequences and use of the sequences and sequence alignments for the development of antibacterial drugs.

The novel eubacterial tmDNA sequences determined in accordance with the present invention are set forth in Tables 1-58, below. The alignment of tmRNA sequences is shown in FIGS. 3A-11B, which also show the structural domains and structural features of the tmRNA. The present invention also includes the tmRNA sequences set forth in these figures to the extent they differ from the sequences set forth in Tables 1-58.

The sequences, especially as identified by the sequence alignment, represent targets for the development of drugs which may be broadly applicable to many kinds of bacteria, or may be broadly applicable only to a particular genera of phylum of bacteria, or may be specifically applicable to a single species of bacteria. Thus, the present invention is further directed to the development of drugs for the therapeutic treatment of bacteria, generically or specifically. Suitable drugs are developed on the basis of the tmRNA sequences as described herein.

For all the novel tmRNA sequences, as well as with the ones that are already known, there are systematically several structural domains that are always found. These domains can be used as targets for the development of drugs which may be genera specific or which may be eubacteria specific. These domains are either RNA helices which can be sometimes interrupted by bulges or pseudoknots. The RNA helices which are always present are H1, H2, H5 and H6. Helices H1 and H6 are found in all canonical transfer RNAs. Thus, H1 and H6 are not good targets for drug development because drugs that would target them will also interfere with the biology of the individual that has a given disease. Consequently, very good candidates for development of drugs for targeting as many bacteria as possible are helices H2 and H5. Moreover, helices H2 and H5 are critical for the folding of all these tmRNA since both of them connect the two ends of the molecule together. Disruption of either H2 or H5 with a specific drug would lead to inactive tmRNA molecules in vivo. Similarly, pseudoknots PK1, PK2 and PK3 are always found in the bacterial tmRNAs. Since these pseudoknots are not found in all canonical transfer RNAs, they can also be targeted with specific drugs. Disruption of either PK1 or PK2 or PK3 with a specific drug would lead to inactive tmRNA molecules in vivo.

In addition to developing drugs which broadly target many bacteria, drugs are developed which are more genera specific. For trying to target specifically a given bacteria or a complete phylum, the coding sequence (shown in all the alignments) is a very good candidate. Indeed, this region of the RNA is very accessible for DNA antisense binding (such as shown for *Escherichia coli*; Matveeva et al., 1997), and thus, is also available for interaction with other drugs. Moreover, the coding sequence is a critical functional domain of the molecule in its quality-control mechanism in cells.

Interestingly, some structural domains are present only in a given bacterial phyla and could be targeted for discovering a drug that will be specific of a phylum, but not of the others. For example:

(1) in the cyanobacteria, the fourth pseudoknot PK4 is made of two smaller pseudoknots called PK4a and PK4b;

(2) in the mycoplasma, helix H2 is made of only 4 base-pairs instead of 5 in the other species;

(3) for two sequences of chlorobium as well as *Bacteroides* thetaiotaomicron and ppm gingiv., there is an additional domain just downstream of the coding sequence that is unique to them;

(4) there is always a stem-loop in the coding sequence of the actinobacteria (Felden et al., 1999); and (5) all the beta proteobacteria possess a sequence insertion in pseudoknot PK2 (shown in the alignment).

The novel sequences described herein, when aligned, show that specific structural domains within tmRNA are strictly conserved, as for example pseudoknot PK1 is located upstream (at the 5'-side) of the coding sequence. As previously disclosed, this pseudoknot is a target for future antibacterial drugs. Moreover, recent data have shown that this PK1 pseudoknot, among all the four pseudoknots within tmRNA gene sequences (sometimes there's only 2 or 3 detectable pseudoknots, depending upon the sequences), is the only one that its correct folding is essential for the biological activity of tmRNA (Nameki et al., 1999; Nameki et al., 2000).

It has recently been discovered that even the alpha-proteobacteria possess tmRNA genes. These genes are permuted and are made in two parts, connected via a processed linker. These tmRNA gene sequences from alpha-proteobacteria were not found in the course of the present invention because usual PCR methods could not amplify them.

Recent reports have shown that whereas the gene encoding tmRNA is non-essential in *E. coli* (does not kill the bacteria when disrupted), it is indeed essential in *Neisseria gonor-*

*rheae* (Huang et al., 2000). Also, tmRNA is directly involved in *Salmonella typhymurium* pathogenticity (Julio et al., 2000).

In summary, tmRNA genes are present in all eubacterial genomes, with no exceptions, but are not present in any genomes from archebacteries or eukaryotes, with the exception of some chloroplasts. The very specific location of tmRNA genes within one of the three main kingdoms of life make them ideal targets for the design of novel antibiotics that will, in principle, interfere very weakly with human biochemistry, compared to usual antibiotics. For a recent review about designing novel antibiotics, see Breithaupt (1999).

The present invention is also directed to diagnostic assays and kits for the detection of bacterial infection, particularly infections caused by bacterial agents disclosed herein. In one embodiment, the coding sequence of each bacterial species is used to design specific primers for use in amplification-based diagnostic assays for infectious diseases. Specific primers are designed in accordance with well known techniques, and such design is readily done by a skilled artisan. Amplification-based diagnostic assays are performed in accordance with conventional techniques well known to skilled artisans. Examples of amplification-based assays include, but are not limited to, polymerase chain reaction (PCR) amplification, strand displacement amplification (SDA), ligase chain reaction (LCR) amplification, nucleic acid sequence based amplification (3SR or NASBA) and amplification methods based on the use of Q-beta replicase.

Drugs which target the sequences described herein are active agents can be formulated in pharmaceutical compositions, which are prepared according to conventional pharmaceutical compounding techniques (*Remington's,* 1990). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may dissolved in a pharmaceutical carrier and administered as either a solution of a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in an therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences* (18).

Alternatively, targeting therapies may be used to deliver the active agent more specifically to certain types of cell, by the use of targeting systems such as antibodies or cell-specific ligands. Targeting may be desirable for a variety of reasons, e.g. if the agent is unacceptably toxic, or would otherwise require too high a dosage, or otherwise be unable to enter the target cells.

Antisense active agents can also be delivered by techniques described in U.S. Pat. Nos. 5,811,088; 5,861,290 and 5,767,102.

EXAMPLES

The present invention is further detailed in the following Examples, which are offered by way of illustration and are not intended to limit the invention in any manner. Standard techniques well known in the art or the techniques specifically described below are utilized.

Example 1

Materials and Methods

1. Extaction of Genomic DNA

Bacterial genomic DNAs were prepared from ≈10 mg freeze-dried cells provided from ATCC (American Type Culture Collection, Virginia, USA). Cell pellets were resuspended in 750 μL of lysis buffer (50 mM Tris (pH 8.0), 50 mM EDTA and 20% sucrose). 150 μL of a 10 mg/mL solution of lysozyme was mixed and let stand at room temperature for 15 min. 150 μL of 1% SDS was added and let stand at room temperature for 15 minutes. Four to five phenol/chloroform extractions were performed, until the sample was clear and there was no interphase. Two to five μL of a 10 mg/mL solution of RNase DNase-free was added and incubated at room temperature for 30 minutes. After a phenol/chloroform extraction of the enzyme, the genomic DNA was precipitated with 1/10 volume of 3M NaOAc (pH 5.5) and 1 volume isopropanol, and stored at −20° C. for 2 hours. After centrifugation, the genomic DNAs were washed with 70% ethanol, vacuum-dried and diluted in sterile water to a final concentration of 10 ng/μL.

2. Primer Sets for PCR Reactions

The following primer sets were used during the PCR: primer set A (based on *E. coli* tmRNA termini):

```
5'-GGG GCT GAT TCT GGA TTC GAC-3'    (SEQ ID NO: 1)
and

5'-TGG AGC TGG CGG GAG TTG AAC-3';   (SEQ ID NO: 2)
```

primer set B (based on *T. neapolitana* tmRNA termini):

```
5'-GGG GGC GGA AAG GAT TCG ACG-3'    (SEQ ID NO: 3)
and

5'-TGG AGG CGG CGG GAA TCG AAC-3';   (SEQ ID NO: 4)
```

primer set C (based on *M. pneumoniae* tmRNA termini):

```
5'-GGG GAT GTC ATG GTT TTG ACA-3'    (SEQ ID NO: 5)
and

5'-TGG AGA TGG CGG GAA TCG AAC-3';   (SEQ ID NO: 6)
and
```

primer set D (based on *C. tepidum* tmRNA termini):

```
5'-GGG GAT GAC AGG CTA TCG ACA-3'    (SEQ ID NO: 7)
and

5'-TGG AGA TGG CGG GAC TTG AAC-3'.   (SEQ ID NO: 8)
```

3. PCR Reaction

Sequences of tmRNA genes were obtained by polymerase chain reaction (PCR) in 25 μL using 40 ng of genomic DNA per reaction. The following general scheme was utilized for all of the sequences:

(a) 94° C. to 96° C. for 4 min. (first denaturation of genomic DNAs, done only once); then (b) 35 to 40 PCR cycles with 2.5 to 5 Units of Taq DNA polymerase in a 25 μL reaction volume, according to the following scheme (40 ng of genomic DNAs/PCR reaction):

1. denature at 94° to −96° C. for 25 to 30 sec;
2. anneal at 44° to 55° C. for 20 to 30 sec; and
3. extension at 72° C. for 10 sec.

The magnesium conc. was optimized for each phyla from 3.5 to 13.5 mM.

4. Elution of Amplified DNAs

The various PCR-amplified tmDNA bands were gel purified (5% PAGE), stained (ethidium bromide staining), cut using a sterile razor blade, and shaken over-night (passive elution, using a vibrator) in a 350 μl solution containing 10 mM Tris-HCl buffer (pH 8.1). The following day, the PCR amplified tmDNAs were ethanol precipitated, washed in 70% ETOH, vacuum dried and the DNA pellets were dissolved in 18 μl of RNase-DNase free sterile water.

5. DNA Sequencing

Six μL of amplified DNAs were added to 3.2 picomoles of the primer that was used in the PCR. To verify the novel tmDNA sequences, each of the two primers were used independently to sequence each of the two PCR-amplified DNA strands. Some tmDNAs were already engineered at their 5'-ends with a T7 promoter, to be able to transcribe directly the tmDNAs into tmRNAs by in vitro transcription.

Dye terminator sequencing was achieved at the DNA sequencing facility of the Human Genetics Institute. In addition to novel tmRNA sequences that are not available publicly, several tmDNA sequences that were already known have been verified and several sequencing mistakes have been found and corrected (especially for *Alcaligenes eutrophus* tmRNA).

Example 2

Amplification Reactions for Eubacterial tmDNA

Eubacterial tmDNA was amplified by PCR in accordance with Example 1, using the following conditions.

Acidobacterium:

Primer Set B; Annealing temp. during PCR: 53° C. for 20 sec; $Mg^{2+}$ conc.: 4.5 mM.

Coprothermobacter:

Primer Set B; Annealing temp. during PCR: 55° C. for 30 sec; $Mg^{2+}$ conc.: 5.5 mM.

Cytophagales:

Primer Set A; Annealing temp. during PCR: 46° C. for 30 sec; $Mg^{2+}$ conc.: 4.5 mM.

Dictyoglomus:

Primer set B; Annealing temp. during PCR: 55° C. for 30 sec; $Mg^{2+}$ conc.: 4.5 mM.

Environmental Samples:

Sludge DNA

Primer set C; Annealing temp. during PCR: 51° C. for 20 sec; $Mg^{2+}$ conc.: 13.5 mM.

Rumenal Fluid DNA

Primer set D; Annealing temp. during PCR: 50° C. for 30 sec; $Mg^{2+}$ conc.: 9.5 mM.

Fibrobacter:

Primer set A; Annealing temp. during PCR: 51° C.; $Mg^{2+}$ conc.: 3.5 mM.

Firmicutes:

Fusobacteria:

Primer set A; Annealing temp. during PCR: 52° C.; $Mg^{2+}$ conc.: 5.5 mM.

High G-C:

Primer set A; Annealing temp. during PCR: 50-55° C.; $Mg^{2+}$ conc.: 4.5 mM.

Low G-C:

Primer sets A or B; Annealing temp. during PCR: 52° C.; $Mg^{2+}$ conc.: 5.5 to 7.5 mM.

Mycoplasmes:

Primer set A; Annealing temp. during PCR: 52° C.; $Mg^{2+}$ conc.: 3.5 to 5.5 mM.

Green Non-Sulfur:

Primer sets A or B; Annealing temp. during PCR: 46 to 52° C.; $Mg^{2+}$ conc.: 4.5 mM.

Green Sulfur:

Primer set A; Annealing temp. during PCR: 46° C.; $Mg^{2+}$ conc.: 4.5 mM.

Planctomycetales:

Primer set A; Annealing temp. during PCR: 48 to 52° C.; $Mg^{2+}$ conc.: 7.5 mM.

Proteobacteria:

Beta:

Primer sets A and/or B; Annealing temp. during PCR: 50° C. for 25 sec; $Mg^{2+}$ conc.: 3.5 mM.

Delta:

Primer set B; Annealing temp. during PCR: 55° C.; $Mg^{2+}$ conc.: 3.5 to 4.5 mM.

Epsilon:

Primer set A; Annealing temp. during PCR: 46° C. for 30 sec; $Mg^{2+}$ conc.: 3.5 mM.

Gamma:

Primer set A; Annealing temp. during PCR: 44 C for 30 sec; $Mg^{2+}$ conc.: 5.5 mM.

Spirochetes:

Primer set A; Annealing temp. during PCR: 52° C.; $Mg^{2+}$ conc.: 4.5 mM.

Thermodesulfobacterium:

Primer set B; Annealing temp. during PCR: 55° C.; $Mg^{2+}$ conc.: 5.5 mM.

Thermotogales:

Primer set B; Annealing temp. during PCR: 46° C.; $Mg^{2+}$ conc.: 7.5 mM.

Deinococcales:

Primer set B; Annealing temp. during PCR: 52° C.; $Mg^{2+}$ conc.: 3.5 mM.

Verrucomicrobia:

Primer set A; Annealing temp. during PCR: 53° C. for 25 sec; $Mg^{2+}$ conc.: 3.5 mM.

Example 3

Amplification of Eubacterial tmDNA

Figure 1B:
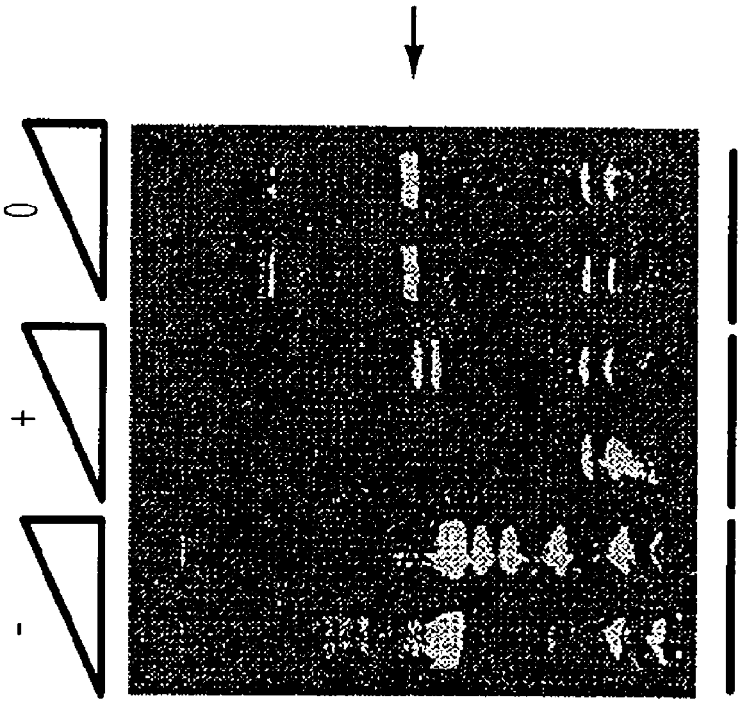

Specific PCR amplification of tmRNA genes was achieved for both thermophilic and mesophilic eubacterial tmRNA genes. For the novel tmDNA genes found in thermophiles, both the magnesium concentration and the annealing temperature (FIG. 1A) were optimized. As shown in FIG. 1A, a specific amplification of *Thermus aquaticus* tmDNA was observed with an annealing temperature around 50° C., whereas at higher temperatures there is a gradual decrease in the amount of amplified tmDNA. For mesophiles, the magnesium concentration during PCR was critical (FIG. 1B), but the annealing temperature could vary from 44° C. to 60° C. without significant effects on the amplification. FIG. 1B shows various effects of increasing the magnesium concentration on the PCR amplification of three novel eubacterial tmDNA genes. Increasing magnesium concentration from 3.5 mM to 5.5 mM has either a negative (FIG. 1B, panel 1), a positive (FIG. 1B, panel 2) or no effect on specifically amplifying eubacterial tmDNA genes.

Figure 2:
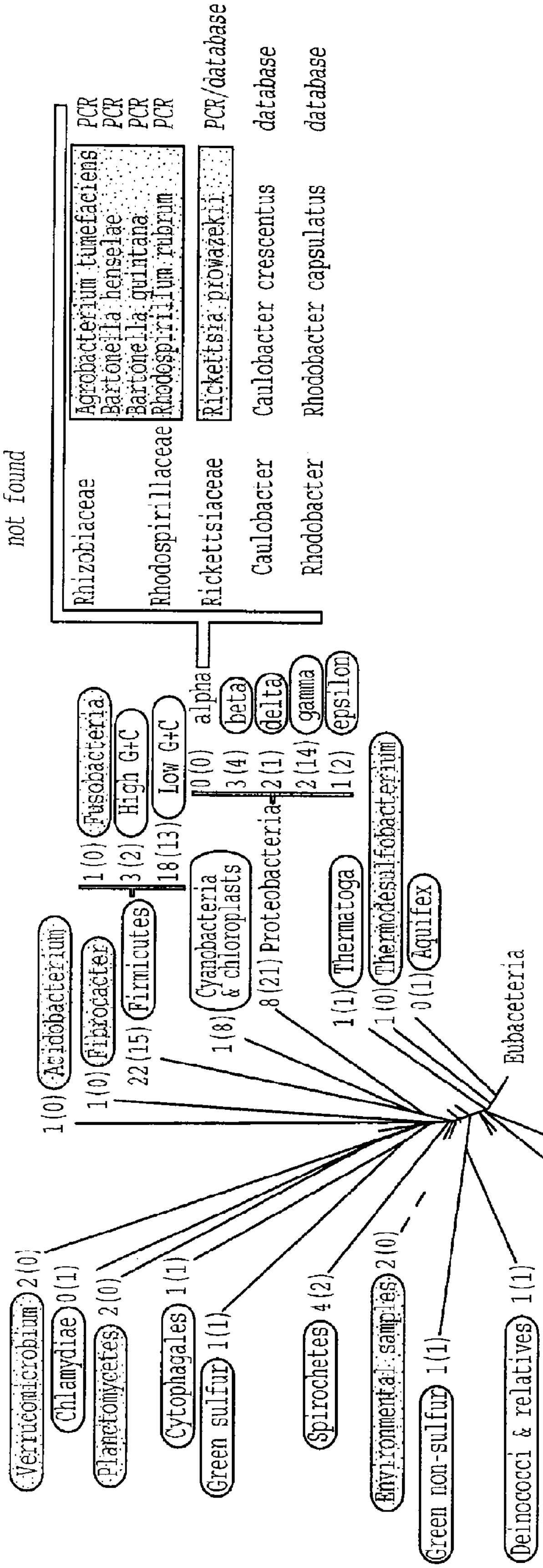
FIG. 2 shows the distribution of tmDNA sequences within eubacterial genomes. The circled phyla or subgroups contain tmDNA sequences and those shaded are new members of this category. The numbers shown close to each phylum are the 51 tmDNA sequences that have are disclosed herein and the numbers in parenthesis are the 53 tmDNA sequences that were previously known (summarized in Williams, 1999; Wower and Zwieb, 1999). The environmental samples are indicated with a dashed line as their connection to the tree is unknown. The 5 alpha-Proteobacteria in which tmDNA sequences were not detected by PCR analysis are labeled "PCR" and the 3 analyzed by Blast search of the complete, or nearly complete, sequenced genomes are labeled "database".
Figure 4A:
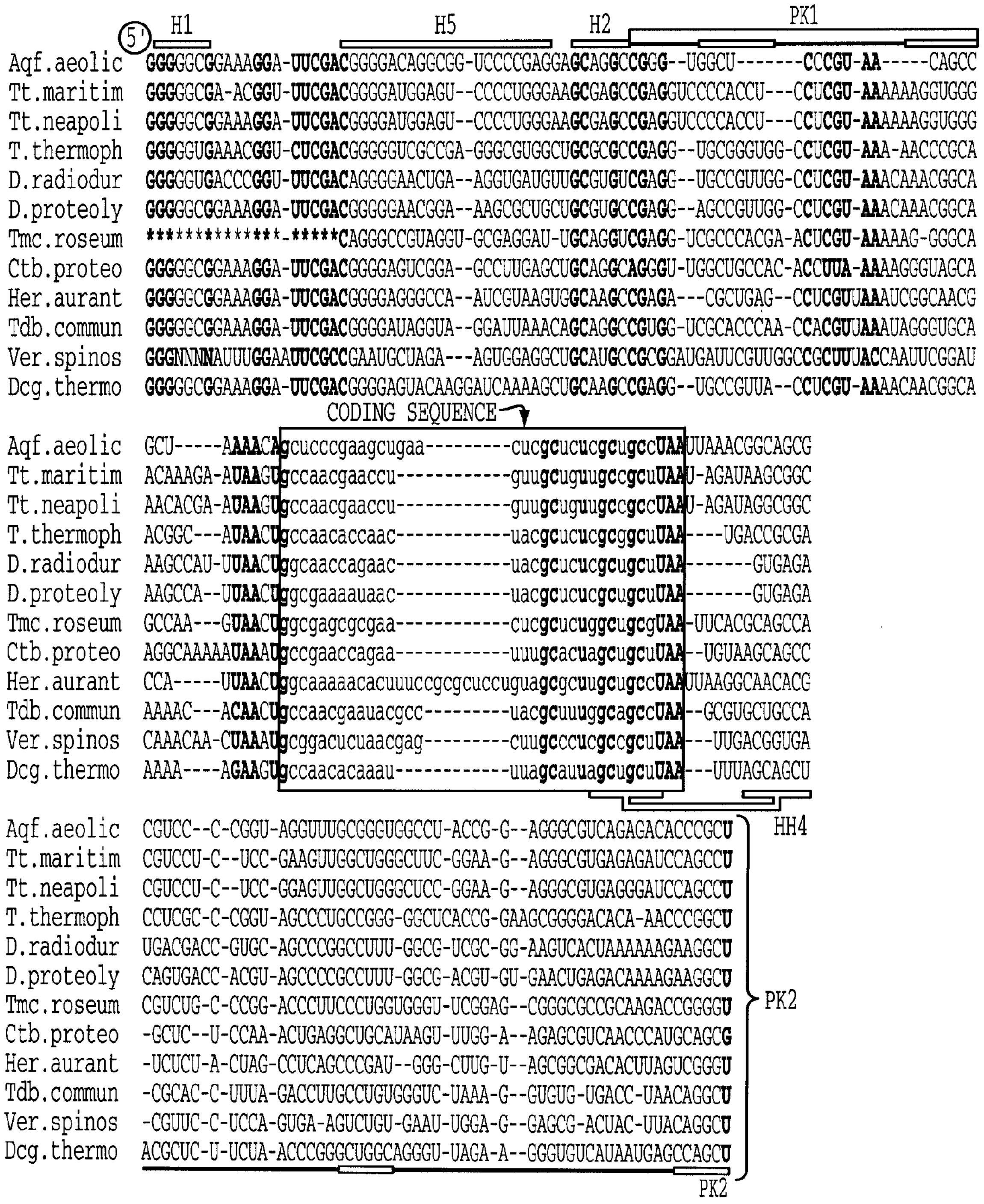
Figure 5A:
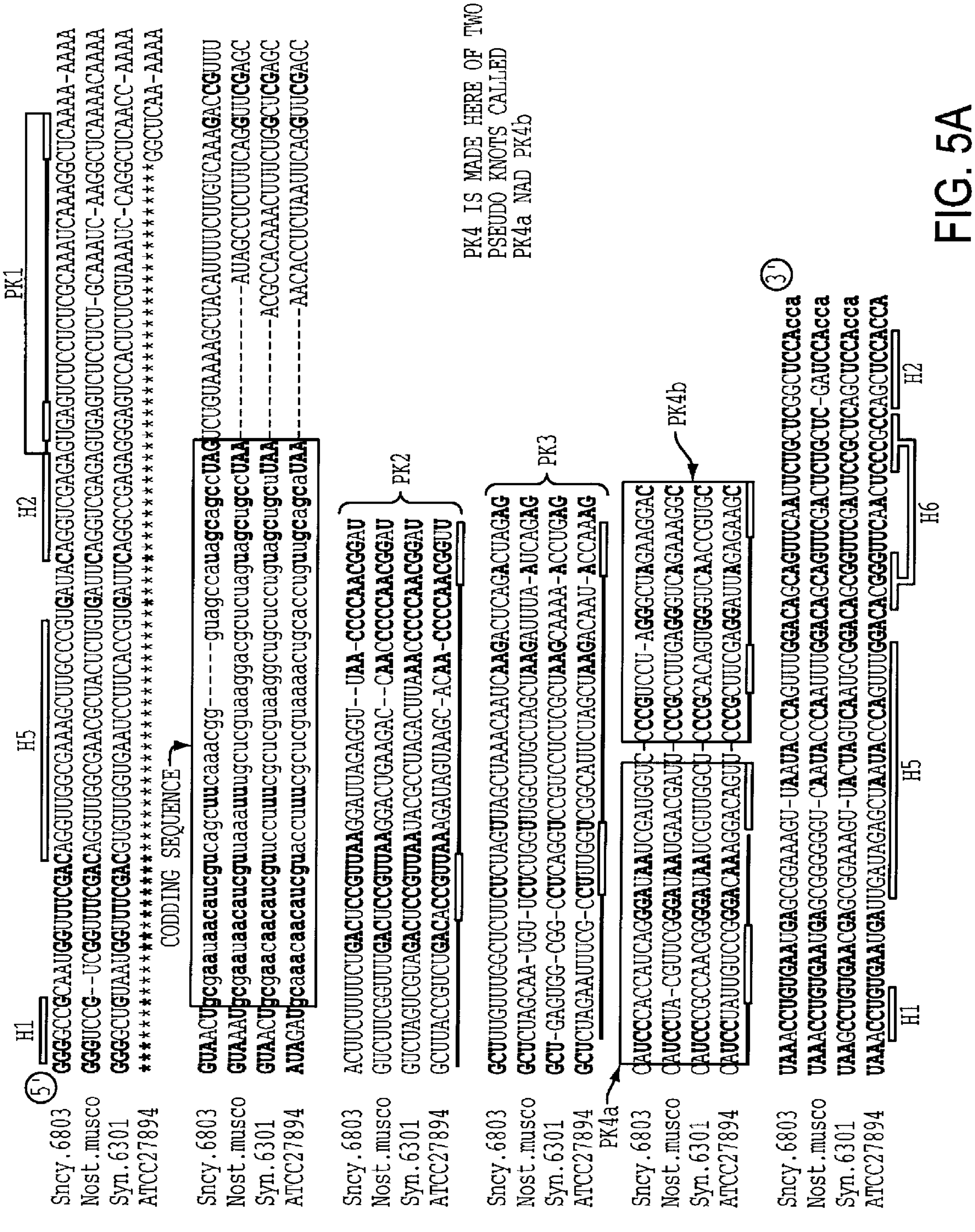
FIGS. 5A and 5B show the sequence alignment, structural domains and structural features for the tmRNA of several species of Cyanobacteries (5A) and chloroplasts (5B). The tmRNA sequences of the Cyanobacteries are set forth in SEQ ID NOs:100-103, and the tmRNA sequences of the chloroplasts are set forth in SEQ ID NOs:104-108.
Figure 5B:
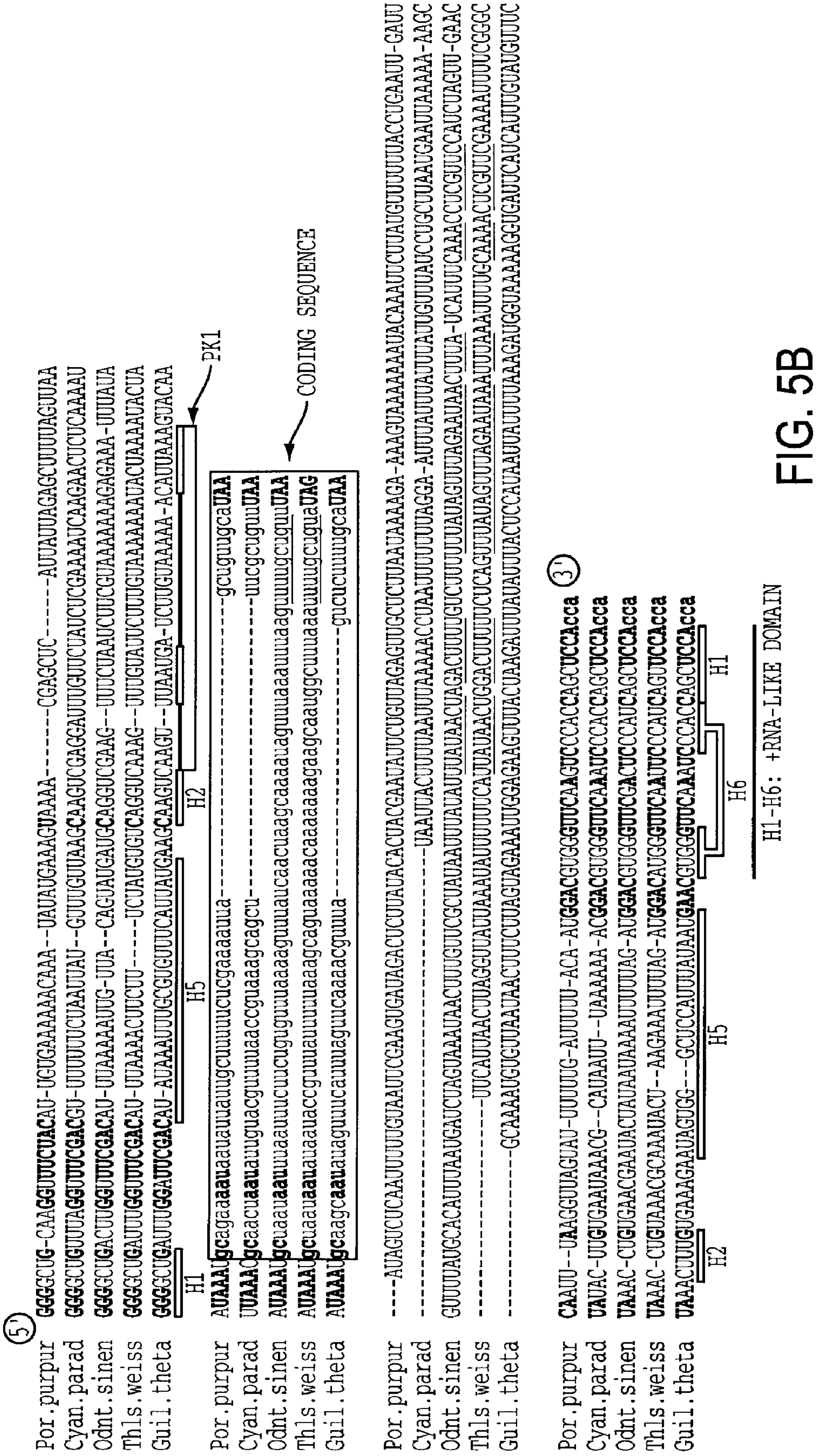
Figure 6A:
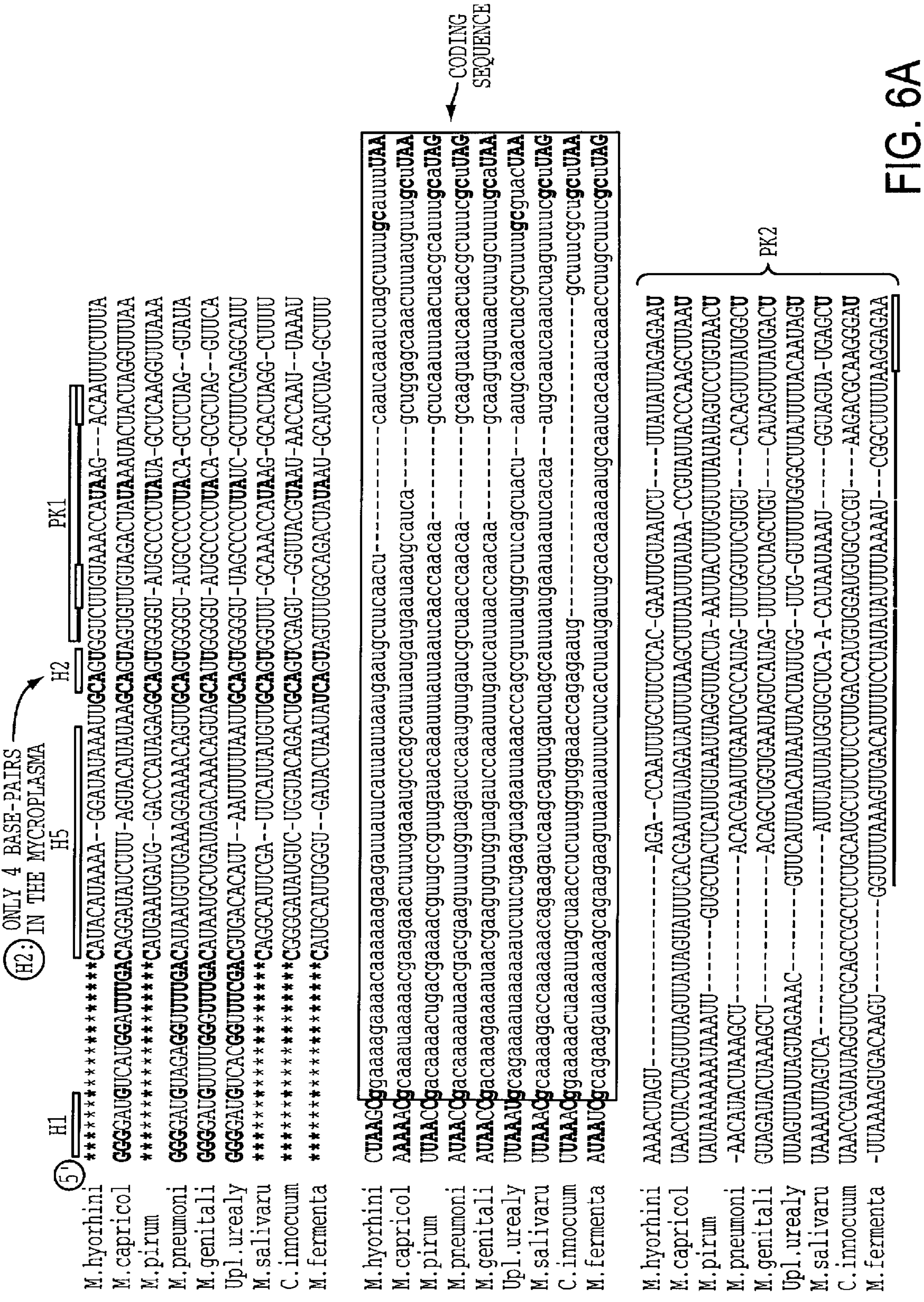
FIGS. 6A and 6B show the sequence alignment, structural domains and structural features for the tmRNA of several species of Mycoplasmes. The tmRNA sequences are set forth in SEQ ID NOs:109-117.
Figure 6B:
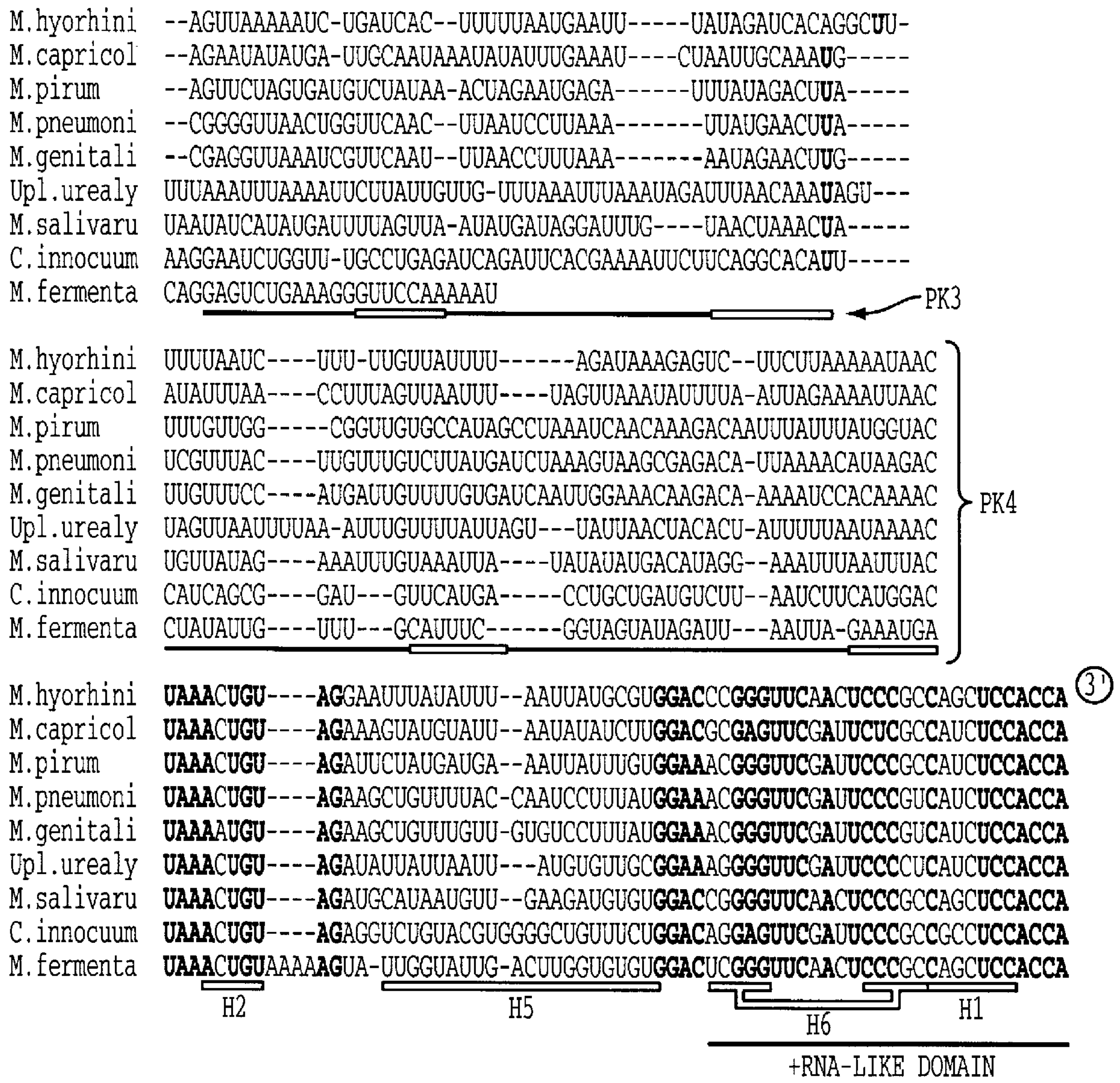
Figures 1, 7A:
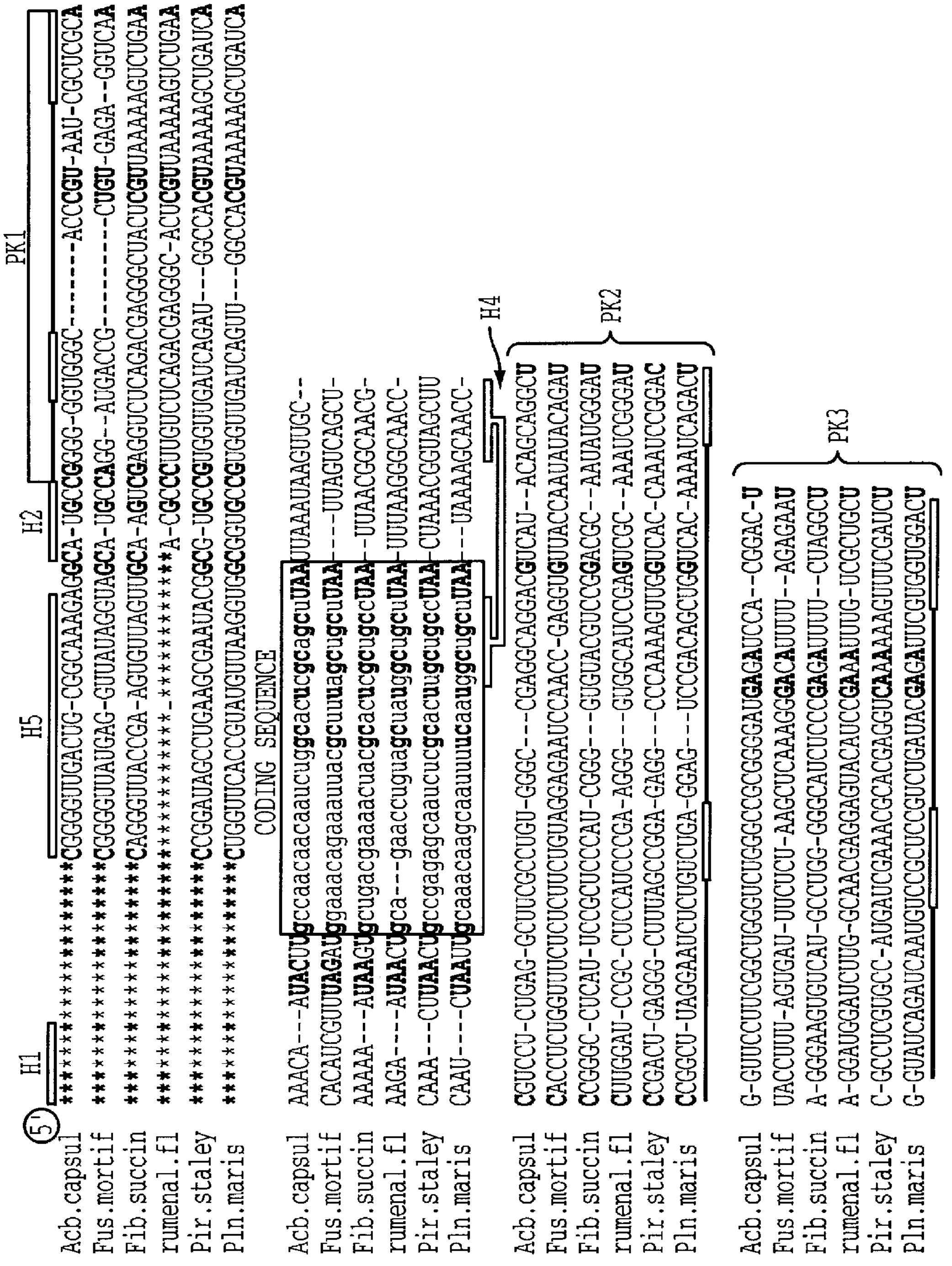
Figures 2, 7A:
Figure 7B:
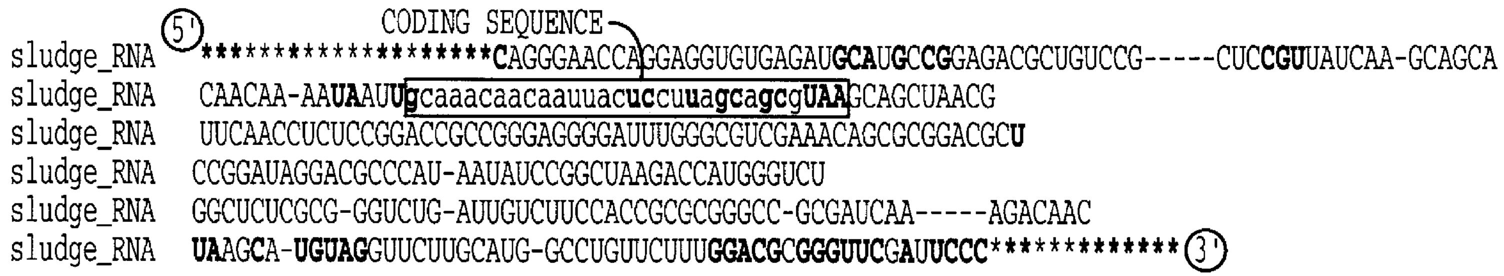
Figure 7C:
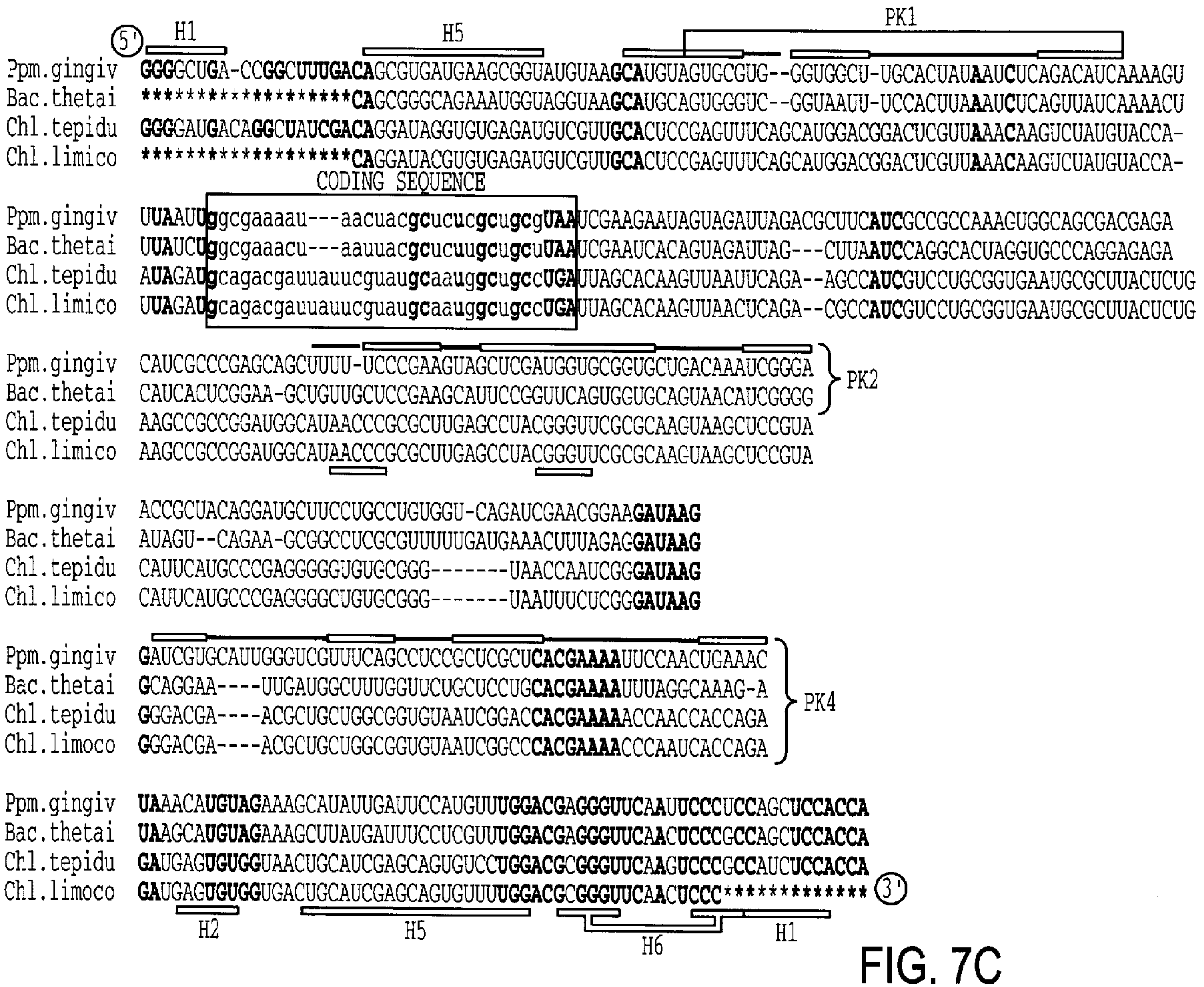
Figure 7D:
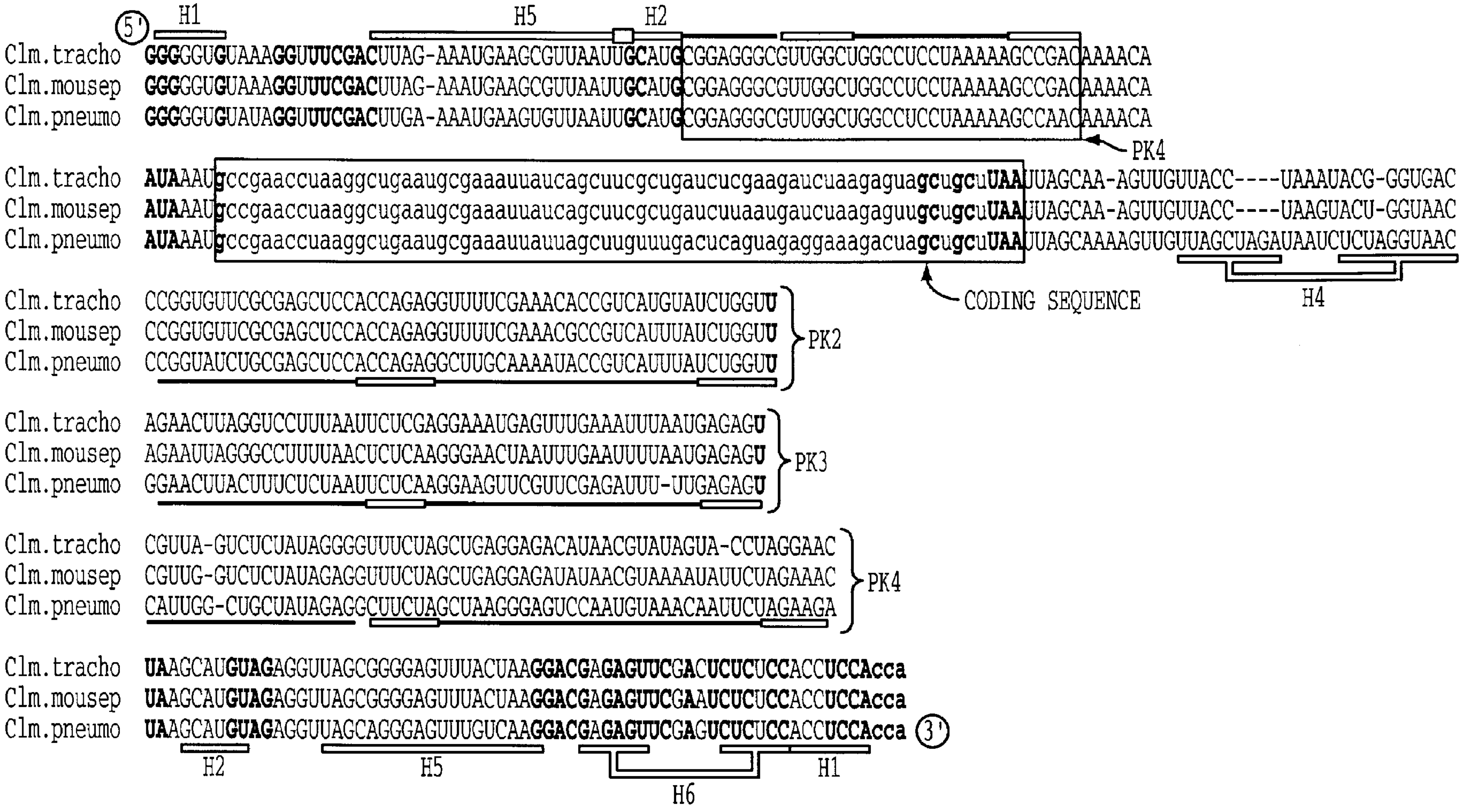
Figure 8A:
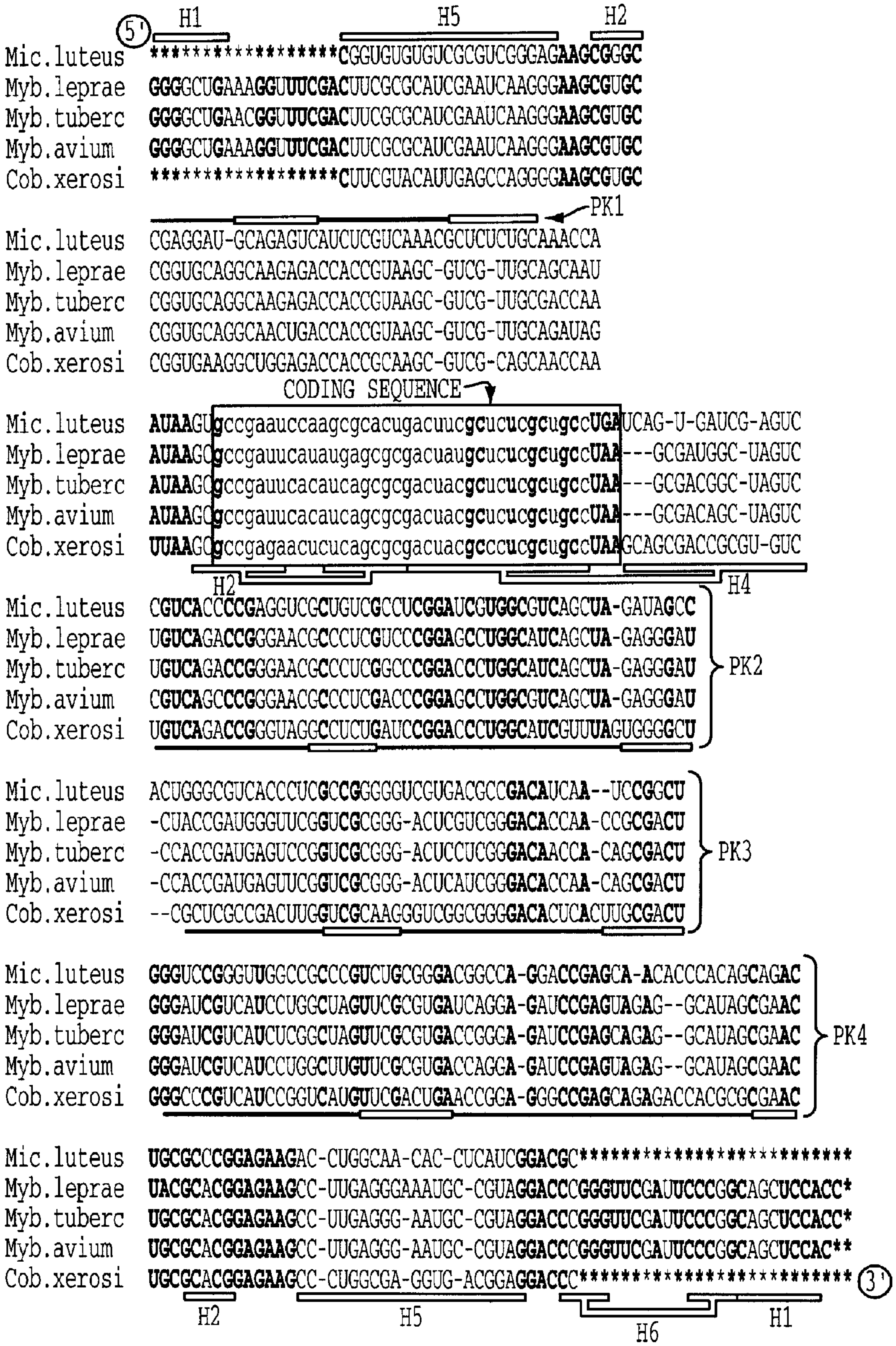
Figure 9A:
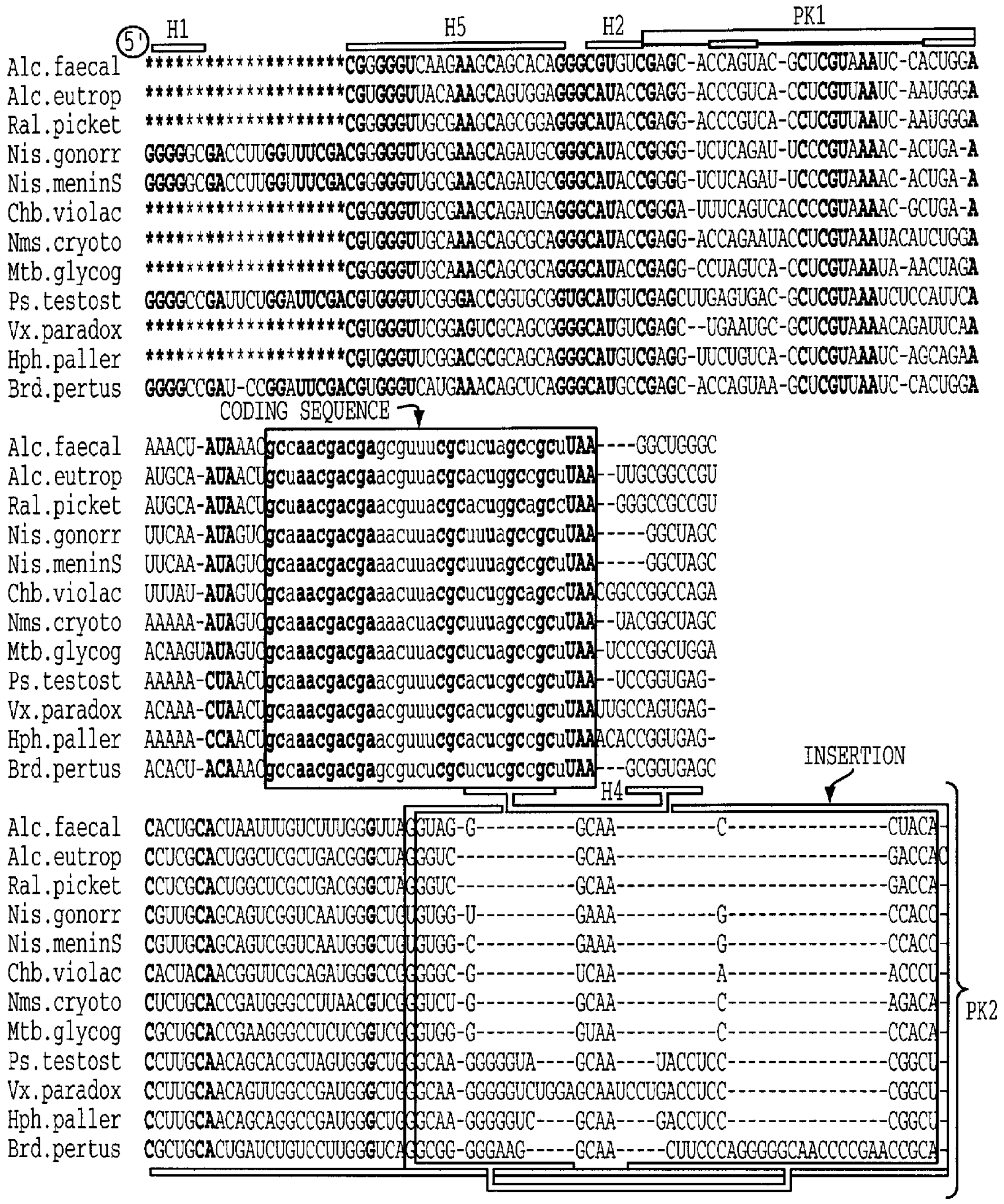
Figure 11A:
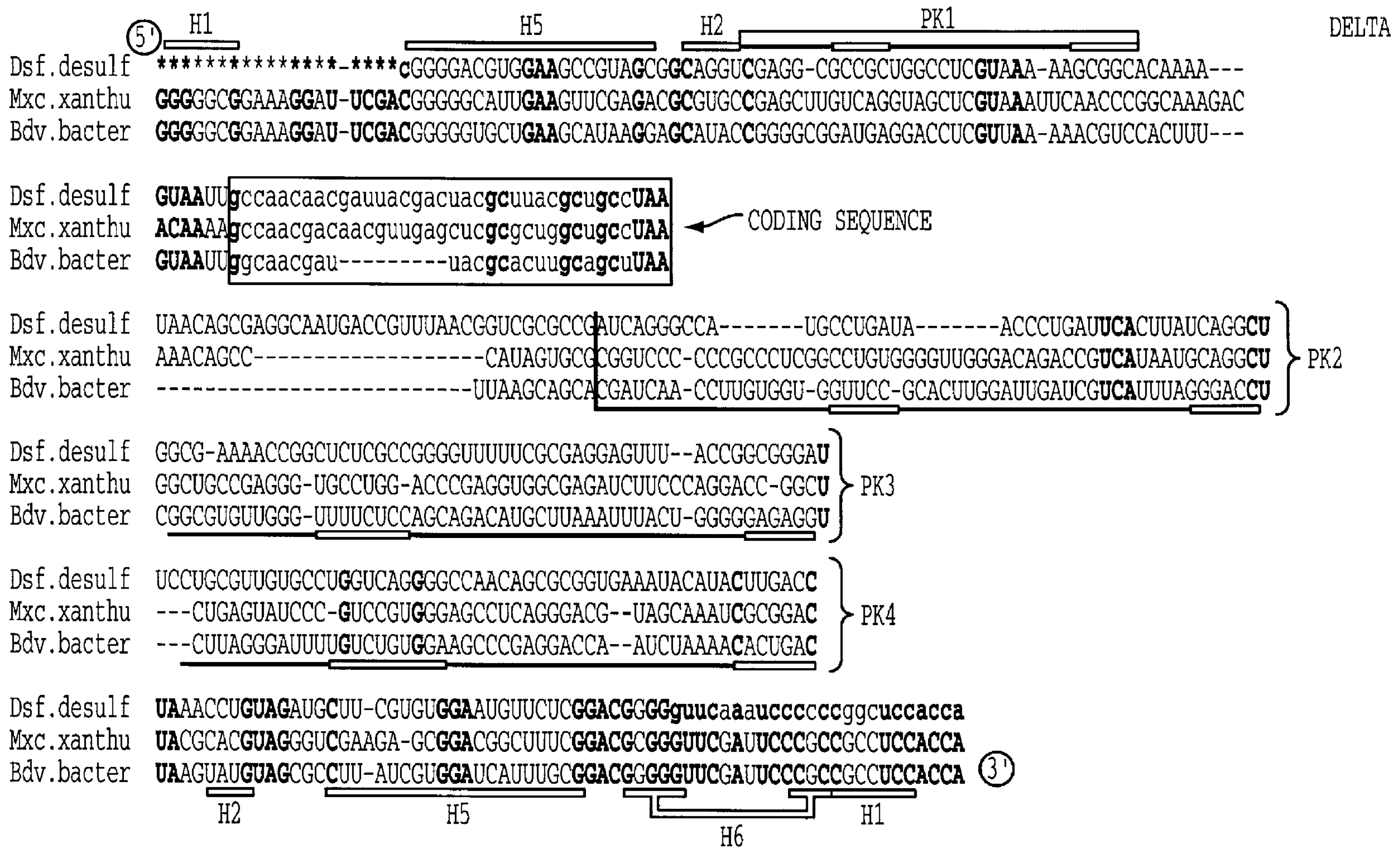
FIGS. 11A and 11B show the sequence alignment, structural domains and structural features for the tmRNA of several species of Pourpres delta (11A) and Pourpres epsilon (11B). The tmRNA sequences of the Pourpres delta are set forth in SEQ ID NOs:170-172, and the tmRNA sequences of the Pourpres epsilon are set forth in SEQ ID NOs:173-175.
Figure 11B:
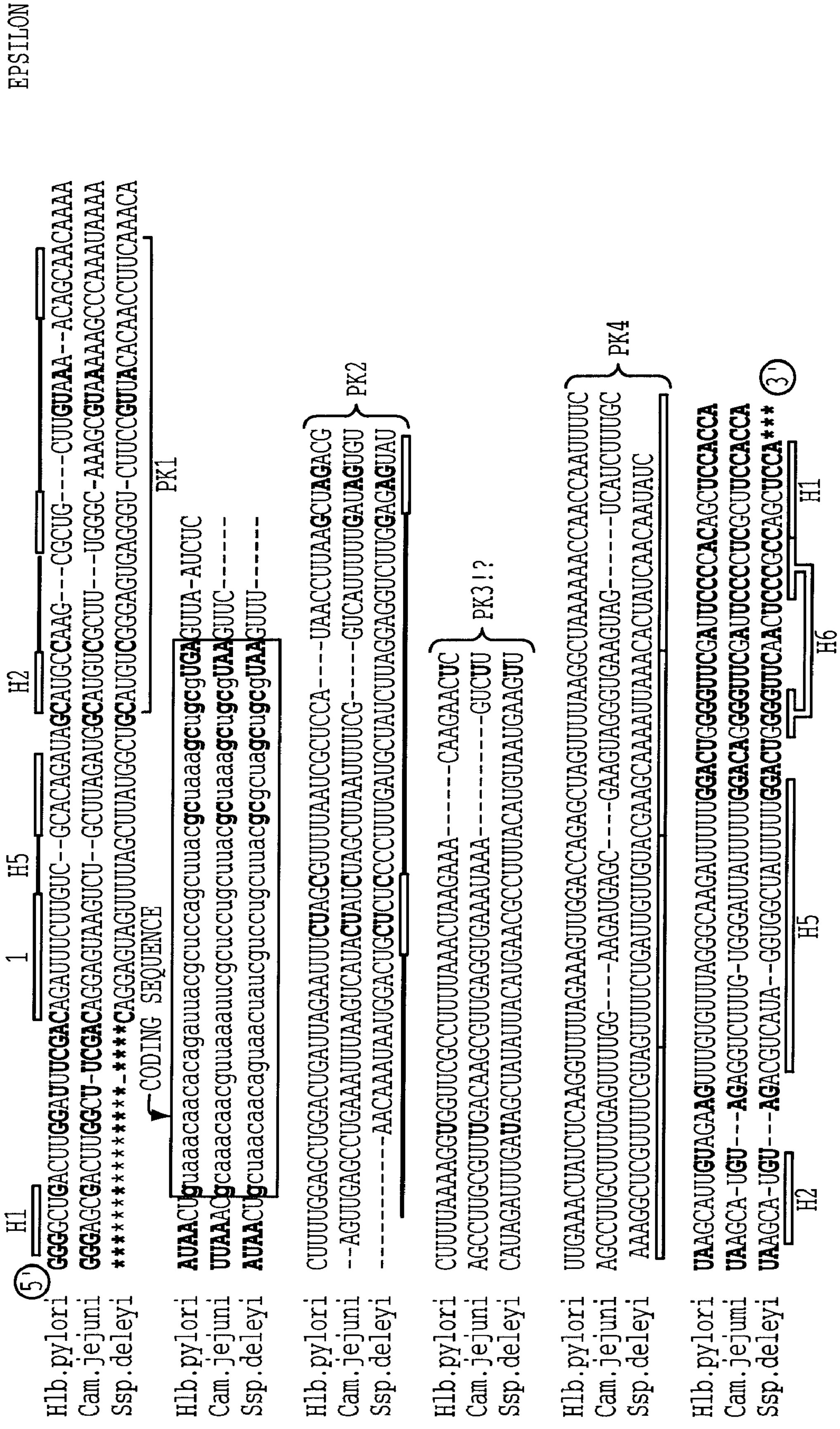

According to these procedures, tmRNA genes from many eubacteria including known human pathogens were amplified. The PCR was facilitated by sequence conservation at both 5' and 3' ends and was performed as described (Williams and Bartel, 1996), with modifications. This study was initiated to collect further sequences from eubacterial tmDNA genes, as well as to test experimentally whether tmDNA genes could be found in all bacterial phyla or subgroups. 51 new tmDNA sequences were determined (FIG. 2), including sequences from members of 8 additional phyla and 1 subgroup (shaded boxes in FIG. 2). The 58 new tmDNA sequences are set forth in Tables 1-58. This brings coverage to a total of 104 sequences in 19 bacterial phyla. Interestingly, tmDNA sequences could be amplified from all species tested apart from those in the alpha-Proteobacteria. Five genomic DNAs from alpha-Proteobacteria (*Agrobacterium tumefaciens, Bartonella henselae, Bartonella quintana, Rhodospirillum rubrum* and *Rickettsia prowazekii*) were extensively checked using various oligonucleotides, annealing temperatures and magnesium concentrations. No specific amplified tmDNA sequences were detected in this subgroup. Moreover, no putative tmDNA sequences could be identified (results herein and Williams, 1999) by Blast searches on the 1 fully sequenced (*Rickettsia prowazekii*) and 2 nearly completed (*Caulobacter crescentus* and *Rhodobacter capsulatus*) alpha-proteobacterial genomes (FIG. 2).

It cannot be ruled out that tmDNA sequences may have largely diverged in the alpha-proteobacterial sub-group compared to other bacterial phyla, and that both PCR methods and Blast searches are missing the relevant sequences. While tmRNA is dispensable in *E. coli* (Ando et al., 1996), it is striking that it has been found in all bacteria tested other than the alpha-Proteobacteria. The alpha-Proteobacteria have undergone reductive evolution. This has been more intensive in one of the two sub-classes than in the other (Gray and Spencer, 1996), but tmRNA sequences have not been found even in the sub-class with the larger genome. Based on sequence comparison, the alpha-Proteobacteria and mitochondria are evolutionary relatives (Yang et al., 1985; Andersson et al., 1998). The drastic downsizing in what has become mitochondrial genomes means that it is not reasonable to draw inferences on the relationship between alpha-Proteobacteria and mitochondria based on their mutual apparent absence of tmRNA. It is nevertheless, of interest, that at least some chloroplasts and cyanelle genomes have tmDNA sequences, and the cyanobacteria, with which they are evolutionary related, also have tmRNA.

TABLE 1

| tmDNA Sequence for *Acidobacterium capsulatum* (*Acidobacterium*) |
|---|
| (SEQ ID NO: 9) |
| GGGGGCGGAAAGGATTCGACGGGGTTGACTGCGGCAAAGAGGCATGCCGG<br>GGGGTGGGCACCCGTAATCGCTCGCAAAACAATACTTGCCAACAACAATC<br>TGGCACTCGCAGCTTAATTAAATAAGTTGCCGTCCTCTGAGGCTTCGCCT<br>GTGGGCCGAGGCAGGACGTCATACAGCAGGCTGGTTCCTTCGGCTGGGTC<br>TGGGCCGCGGGGATGAGATCCACGGACTAGCATTCTGCGTATCTTGTCGC<br>TTCTAAGCGCAGAGTGCGAAACCTAAAGGAATGCGACTGAGCATGGAGTC<br>TCTTTTCTGACACCAATTTCGGACGCGGGTTCGATTCCCGCCGCCTCCAC<br>CA |

TABLE 2

| tmDNA Sequence for *Coprothermobacter proteolyticus* (60 degrees) |
|---|
| (SEQ ID NO: 10) |
| GGGGGCGGAAAGGATTCGACGGGGAGTCGGAGCCTTGAGCTGCAGGCAGG<br>GTTGGCTGCCACACCTTAAAAAGGGTAGCAAGGCAAAAATAAATGCCGAA<br>CCAGAATTTGCACTAGCTGCTTAATGTAAGCAGCCGCTCTCCAAACTGAG<br>GCTGCATAAGTTTGGAAGAGCGTCAACCCATGCAGCGGCTCTTAAGCAGT<br>GGCACCAGCTGTTTAAGGGTGAAAAGAGTGGTGCTGGGCAGTGCGGTTGG<br>GCTTCCTGGGCTGCACTGTCGAGACTTCACAGGAGGGCTAAGCCTGTAGA<br>CGCGAAAGGTGGCGGCTCGTCGGACGCGGGTTCGATTCCCGCCGCCTCCA<br>CCA |

TABLE 3

| tmDNA Sequence for *Bacteroides thetaiotaomicron* (*bacteroides/flavobacterium*) |
|---|
| (SEQ ID NO: 11) |
| GGGGCTGATTCTGGATTCGACAGCGGGCAGAAATGGTAGGTAAGCATGCA<br>GTGGGTCGGTAATTTCCACTTAAATCTCAGTTATCAAAACTTTATCTGGC<br>GAAACTAATTACGCTCTTGCTGCTTAATCGAATCACAGTAGATTAGCTTA<br>ATCCAGGCACTAGGTGCCAGGACGAGACATCACTCGGAAGCTGTTGCTCC<br>GAAGCATTCCGGTTCAGTGGTGCAGTAACATCGGGGATAGTCAGAAGCGG<br>CCTCGCGTTTTTGATGAAACTTTAGAGGATAAGGCAGGAATTGATGGCTT<br>TGGTTCTGCTCCTGCACGAAAATTTAGGCAAAGATAAGCATGTAGAAAGC<br>TTATGATTTCCTCGTTTGGACGAGGGTTCAACTCCCGCCAGCTCCACCA |

TABLE 4

| tmDNA Sequence for *Dictyoglomus thermophilum* (70 degrees) |
|---|
| (SEQ ID NO: 12) |
| GGGGCTGATTCTGGATTCGACAGGGAGTACAAGGATCAAAAGCTGCAAGC<br>CGAGGTGCCGTTACCTCGTAAAACAACGGCAAAAAAGAAGTGCCAACACA |

TABLE 4-continued

| tmDNA Sequence for *Dictyoglomus thermophilum* (70 degrees) |
|---|
| AATTTAGCATTAGCTGCTTAATTTAGCAGCTACGCTCTTCTAACCCGGGC<br>TGGCAGGGTTAGAAGGGTGTCATAATGAGCCAGCTGCCCCTTCCGACTCC<br>CCTAAGGAAGGGAAAGATGTAGGGGATAGGTGCTTACAGAATCCTGCGGG<br>AGGGAGTCTGTAAGTGCCGAAAAGTTAAAACTCCCGCTAAGCTTGTAGAG<br>GCTTTTGATTCTTGCTCTCTGGACGCGGGTTCAACTCCCGCCAGCTCCAC<br>CA |

TABLE 5

| tmDNA Sequence for Environmental Sample from Rumenal Fluid |
|---|
| (SEQ ID NO: 13)<br>ACGCCCTTGTCTCAGACGAGGGCACTCGTTAAAAAGTCTGAAAAGAATAA<br>CTGCAGAACCTGTAGCTATGGCTGCTTAATTTAAGGGCAACCCTTGGATC<br>CGCCTCCATCCCGAAGGGGTGGCATCCGAGTCGCAAATCGGGATAGGATG<br>GATCTTGGCAACGAGGAGTACATCCGAAATTTGTCGCTGCTGGCTGAAGC<br>ATCGCCGTTCCTCTTTGGGCGTGGCAAGGCAAGATTAAATTCAGAGGATA<br>AGCGTGTAGTAGCGAGTGAGTAGGTGTTTTTGGACGCGGGTTCAAGTCCC<br>GCCATCTCCACCA |

TABLE 6

| tmDNA Sequence for Environmental Sample from Sludge |
|---|
| (SEQ ID NO: 14)<br>GGGGATGTCATGGTTTTGACAGGGAACCAGGAGGTGTGAGATGCATGCCG<br>GAGACGCTGTCCGCTCCGTTATCAAGCAGCAAACAAAACTAATTGCAAAC<br>AACAATTACTCCTTAGCAGCGTAAGCAGCTAACGTTCAACCTCTCCGGAC<br>CGCCGGGAGGGGATTTGGGCGTCGAAACAGCGCGGACGCTCCGGATAGGA<br>CGCCCATAATATCCGGCTAAGACCATGGGTCTGGCTCTCGCGGGTCTGAT<br>TGTCTTCCACCGCGCGGGCCGCGATCAAAGACAACTAAGCATGTAGGTTC<br>TTGCATGGCCTGTTCTTTGGACGCGGGTTCGATTCCCGCCATCTCCACCA |

TABLE 7

| tmDNA Sequence for *Fibrobacter succinogenes* (*Fibrobacter*) |
|---|
| (SEQ ID NO: 15)<br>GGGGCTGATTCTGGATTCGACAGGGTTACCGAAGTGTTAGTTGCAAGTCG<br>AGGTCTCAGACGAGGGCTACTCGTTAAAAAGTCTGAAAAAAAATAAGTGC<br>TGACGAAAACTACGCACTCGCTGCCTAATTAACGGCAACGCCGGGCCTCA<br>TTCCGCTCCCATCGGGGTGTACGTCCGGACGCAATATGGGATAGGGAAGT<br>GTCATGCCTGGGGGCATCTCCCGAGATTTTCTAGGCTGGTCAAACTCCGC<br>GCCGACCTTCTTGGGCGTGGATAAGACGAGATCTTAAATTCGAAGGGAAC<br>ACTTGTAGGAACGTACATGGACGTGATTTTGGACAGGGGTTCAACTCCCG<br>CCAGCTCCA |

TABLE 8

| tmDNA Sequence for *Fusobacterium mortiferum* |
|---|
| (SEQ ID NO: 16)<br>GGGGCTGATTCTGGATTCGACGGGGTTATGAGGTTATAGGTAGCATGCCA<br>GGATGACCGCTGTGAGAGGTCAACACATCGTTTAGATGGAAACAGAAATT<br>ACGCTTTAGCTGCTTAATTAGTCAGCTCACCTCTGGTTTCTCTCTTCTGT<br>AGGAGAATCCAACCGAGGTGTTACCAATATACAGATTACCTTTAGTGATT<br>TCTCTAAGCTCAAAGGGACATTTTAGAGAATAGCTTCAGTTAGCCCTGTC<br>TGCGGGAGTGATTGTTGCGAAATAAAATAGTAGACTAAGCATTGTAGAAG<br>CCTATGGCGCTGGTAGTTTCGGACACGGGTTCAACTCCCGCCAGCTCCAA |

TABLE 9

| tmDNA Sequence for *Corynebacterium xerosis* (gram +, high G-C content) |
|---|
| (SEQ ID NO: 17)<br>GGGGCTGATTCTGGATTCGACTTCGTACATTGAGCCAGGGGAAGCGTGCC<br>GGTGAAGGCTGGAGACCACCGCAAGCGTCGCAGCAACCAATTAAGCGCCG<br>AGAACTCTCAGCGCGACTACGCCCTCGCTGCCTAAGCAGCGACCGCGTGT<br>CTGTCAGACCGGGTAGGCCTCTGATCCGGACCCTGGCATCGTTTAGTGGG<br>GCTCGCTCGCCGACTTGGTCGCAAGGGTCGGCGGGGACACTCACTTGCGA<br>CTGGGCCCGTCATCCGGTCATGTTCGACTGAACCGGAGGGCCGAGCAGAG<br>ACCACGCGCGAACTGCGCACGGAGAAGCCCTGGCGAGGTGACGGAGGACC<br>CGGGTTCAACTCCCGCCAGCTCCACCA |

TABLE 10

| tmDNA Sequence for *Micrococcus luteus* (parfait) |
|---|
| (SEQ ID NO: 18)<br>GGGGCTATTCTGGATTCGACGGTGTGTGTCGCGTCGGGAGAAGCGGGCCG<br>AGGATGCAGAGTCATCTCGTCAAACGCTCTCTGCAAACCAATAAGTGCCG<br>AATCCAAGCGCACTGACTTCGCTCTCGCTGCCTGATCAGTGATCGAGTCC<br>GTCACCCCGAGGTCGCTGTCGCCTCGGATCGTGGCGTCAGCTAGATAGCC<br>ACTGGGCGTCACCCTCGCCGGGGGTCGTGACGCCGACATCAATCCGGCTG<br>GGTCCGGGTTGGCCGCCCGTCTGCGGGACGGCCAGGACCGAGCAACACCC<br>ACAGCAGACTGCGCCCGGAGAAGACCTGGCAACACCTCATCGGACGCGGG<br>TTCAACTCCCGCANTCCCACCA |

TABLE 11

| tmDNA Sequence for *Mycobacterium smegmatis* |
|---|
| (SEQ ID NO: 19)<br>TCATCTCGGCTTGTTCGCGTGACCGGGAGATCCGAGTAGAGACATAGCGA<br>ACTGCGCACGGAGAGGGGCTGATTCCTGGATTCGACTTCGAGCATCGAAT<br>CCAGGGAAGCGTGCCGGTGCAGGCAAGAGACCACCGTAAGCGTCGTTGCA<br>ACCAATTAAGCGCCGATTCCAATCAGCGCGACTACGCCCTCGCTGCCTAA<br>GCGACGGCTGGTCTGTCAGACCGGGAGTGCCCTCGGCCCGGATCCTGGCA<br>TCAGCTAGAGGGACCCACCCACGGGTTCGGTCGCGGGACCTGTGGGGACA<br>TCAAACAGCGACTGGGATCGAGCCTCGAGGACATGCCGTAGGACCCGGGT<br>TCAACTCCCGCCAGCTCCACCA |

TABLE 12

| tmDNA Sequence for *Bacillus badius* |
|---|
| (SEQ ID NO: 20)<br>GGGGGTGATTCTGGATTCGACAGGGATAGTTCGAGCTTGGGCTGCGAGCC<br>GGAGGGCCGTCTTCGTACCAACGCAAACGCCTAAATATAACTGGCAAAAA<br>AGATTTAGCTTTAGCTGCCTAATATAGGTTCAGCTGCTCCTCCCGCTATC<br>GTCCATGTAGTCGGGTAAGGGGTCCAAACTTAGTGGACTACGCCGGAGTT<br>CTCCGCCTGGGGACAAAGGAAGAGATCAATCAGGCTAGCTGCCCGGACGC<br>CCGTCGATAGGCAAAAGGAACAGTGAACCCCAAATATATCGACTACGCTC<br>GTAGACGTTCAAGTGGCGTTATCTTTGGACGTGGGTTCAACTCCCGCCAG<br>CTCCA |

TABLE 13

| tmDNA Sequence for *Bacillus brevis* |
|---|
| (SEQ ID NO: 21)<br>GGGGGCGGAAAGGATTCGACGGGGATGGTAGAGCATGAGAAGCGAGCCGG<br>GGGGTTGCGGACCTCGTCACCAACGCAAACGCCATTAACTGGCAACAAAC<br>AACTTTCTCTCGCTGCTTAATAACCAGTGAGGCTCTCCCACTGCATCGGC<br>CCGTGTGCCGTGGATAGGGCTCAACTTTAACGGGCTACGCCGGAGGCTTC<br>CGCCTGGAGCCAAAGGAAGAAGACCAATCAGGCTAGGTGCCAGGTCAGCG<br>CGTCACTCCGCGAATCTGTCACCGAAACTCTAAACGAGTGACTGCGCTCG<br>GAGATGCTCATGTATCGCTGTTTTCGGACGGGGGTTCGATTCCCGCCGCC<br>TCACCCA |

TABLE 14 tmDNA Sequence for *Bacillus thermoleovorans* (50-60 degres)

(SEQ ID NO: 22)

GGGGGCGGAAAGGATTCGACGGGGGTAGGTCGAGCTTAAGCGGCGAGCCG
AGGGGGACGTCCTCGTAAAAACGTCACCTAAAGATAACTGGCAAACAAAA
CTACGCTTTAGCTGCCTAATTGCTGCAGCTAGCTCCTCCCGCCATCGCCC
GCGTGGCGTTCGAGGGGCTCATATGGAGCGGGCTACGCCCAAATCCGCCG
CCTGAGGATGAGGGAAGAGACGAATCAGGCTAGCCGCCGGGAGGCCTGTC
GGTAGGCGGAACGGACGGCGAAGCGAAATATACCGACTACGCTCGTAGAT
GCTTAAGTGGCGATGCCTCTGGACGTGGGTTCGATTCCCGCCGCCTCCCC
ACCA

TABLE 15 tmDNA Sequence for *Clostridium innocuum*

(SEQ ID NO: 23)

GGGGGCGGAAAGGATTCGACGGGGATATGTCTGGTACAGACTGCAGTCGA
GTGGTTACGTAATAACCAATTAAATTTAAACGGAAAAACTAAATTAGCTA
ACCTCTTTGGTGGAAACCAGAGAATGGCTTTCGCTGCTTAATAACCGATA
TAGGTTCGCAGCCGCCTCTGCATGCTTCTTCCTTGACCATGTGGATGTGC
GCGTAAGACGCAAGGGATAAGGAATCTGGTTTGCCTGAGATCAGATTCAC
GAAAATTCTTCAGGCACATTCATCAGCGGATGTTCATGACCTGCTGATGT
CTTAATCTTCATGGACTAAACTGTAGAGGTCTGTACGTGGGGCTGTTTCT
GGACAGGAGTTCGATTCCCGCCGCCTCACCACCA

TABLE 16 tmDNA Sequence for *Clostridium lentocellum*

(SEQ ID NO: 24)

GGGGGCGGAAAGGATTCGACGGGGGTCACATCTACTGGGGCAGCCATCCG
TAGAACGCCGGAGTCTACGTTAAAAGCTGGCACTTAAAGTAAACGCTGAA
GATAATTTAGCAATCGCTGCCTAATTAAGGCGCAGTCCTCCTAGGTCTTC
CGCAGCCTAGATCAGGGCTTCGACTCGCGGATCCTTCACCTGGCAAAGCT
TTGAGCCAACGTGAACACTATGAAGCTACTAAAATCTAGAGCCTGTCTTT
GGGCGCTAGATGGAGGGAATGTCAAAACAAAGAATATGATGGTAGAGACC
ACGCTATATGGGCTTTCGGACAGGGGTTCGATTCCCGCCGCCTTCACCA

TABLE 17 tmDNA Sequence for *Clostridium perfringens*

(SEQ ID NO: 25)

GGGGCTGATTCTGGATTCGACGGGGGTAAGATGGGTTTGATAAGCGAGTC
GAGGGAAGCATGGTGCCTCGATAATAAAGTATGCATTAAAGATAAACGCA
GAAGATAATTTTGCATTAGCAGCTTAATTTAGCGCTGCTCATCCTTCCTC
AATTGCCCACGGTTGAGAGTAAGGGTGTCATTTAAAAGTGGGGAACCGAG
CCTAGCAAAGCTTTGAGCTAGGAACGGAATTTATGAAGCTTACCAAAGAG
GAAGTTTGTCTGTGGACGTTCTCTGAGGGAATTTTAAAACACAAGACTAC
ACTCGTAGAAAGTCTTACTGGTCTGCTTTCGGACACGGGTTCAACTCCCG
CCACTCCA

TABLE 18 tmDNA Sequence for *Clostridium stercorarium*

(SEQ ID NO: 26)

GGGGGCGGAAAGGATTCGACGGGGTTATTGAAGCAAGAGTAGCGGGTAGA
GGATTCTCGTTGGCCTCTTTAAAAAACGAGAGCTAAAAATAAACGCAAAC
AACGATAACTACGCTTTAGCTGCTGCGTAAGTAACACGCAGCCCGTCGGC
CCCGGGGTTCCTGCGCCTCGGGATACCGGCGTCATCAAGGCAGGGAACCA
GCCGGATCAGGCTTCAGGTCCGGTGGGATTTAATGAAGCTACCGACTTAT
AAAGCCTGTCTCTGGGCGTTATAAGAAGGGAATGTCAAAACAGAGACTGC
ACCCGGAGAAGCTCTTGTGGATATGGTTCCGGACACGAGTTCGATTCCCG
CCGCCTCCACCA

TABLE 19 tmDNA Sequence for *Enterococcus faecium* (sp.)

(SEQ ID NO: 27)

GGGGCTGATTATGGATTCGACAGGATNGTTGAGCTTGAATTGCGTTTCGT
AGGTTACGGCTACGTTAAAACGTTACAGTTAAATATAACTGCTAAAAACG
AAAACAATTCTTTCGCTTTAGCTGCCTAAAAACCAGCTAGCGAAGATCCT
CCCGGCATCGCCCATGTGCTCGGGTCAGGGTCCTAATCGAAGTGGGATAC
GCTAAATTTTTCCGTCTGTAAAATTTAGAGGAGCTTACCAGACTAGCAAT
ACAAGAATGCCTGTCACTCGGCACGCTGTAAAGCGAACCTTTAAATGAGT
GTCTATGAACGTAGAGATTTAAGTGGGAATATGTTTTGGACGCGGGTTCA
ACTCCCGCCAGCTCCACCA

TABLE 20 tmDNA Sequence for *Heliobacillus mobilis* (photosyn/gram +)

(SEQ ID NO: 28)

GGGGCTGATTCTGGATTCGACGGGGAACGTGTTTGCTTGGGATGCGAGCC
GGGTTGCCGCCAGGACCGTAAAAAGGGCGGAAGGCTTTAATTGCCGAAGA
TAACTACGCTTTAGCTGCTTAATTGCAGTCTAACCTCTTCTCCTCTGTGC
TCTCGGTGAGGATGTAAGGGGTCATTTAAGAGAGCTGGCTTCGACCAATT
CTCGGAGGTCCAAGCGAGATTTATCGAGATAGCCTGACCAACGCTCTGTC
TGCCGTGCGGAAGGAAGGCGAAATCTAAAACGACAGACTACGCTCGTAGT
GTCCTTTGTGGGCATTTCTTCGGACGCGGGTTCAACTCCCGCCAGCTCCA
CCA

TABLE 21 tmDNA Sequence for *Heliospirillum gestii*

(SEQ ID NO: 29)

GGGGCTGATTCTGGATTCGACGGGGAACGTGTTTGCTTAGGACGCGAGCC
GGGTTGCCGCCAGGACCGTAAAAAGGGCGGAAGGCTTTAATTGCCGAAGA
TAACTACGCTTTAGCTGCTTAATTGCAGTCTAACCTCTTCTCCTCTGTGC
TCTCGGTGAGGATGTAAGGGGTCATTTAAGAGAGCTGGCTCGAACCAATT
CTCGGAGGTTCGGGTAAGACTTATCGAGATAGCCTGACCAACGCTCTGTC
TGCCGTGCGGAAGGATGGCGAAATCTAAAACGACAGAATACGCTCGTAGT
GTCCTTTGTGGGCATTTCTTCGGACGCGGGTTCAACTCCCGCCAGCTCCA
CCA

TABLE 22 tmDNA Sequence for *Lactobacillus acidophilus*

(SEQ ID NO: 30)

GGGGCTGATTCTGGATTCGACAGGCGTAGACCCGCATTGACTGCGGTTCG
TAGGTTACGTCTACGTAAAAACGTTACAGTTAAATATAACTGCAAATAAC
AAAAATTCTTACGCATTAGCTGCTTAATTTAGCGCATGCGTTGCTCTTTG
TCGGTTTACTCGTGGCTGACACTGAGTATCAACTTAGCGAGTTACGTTTA
ACTACCTCACCTGAATAGTTGAAAAGAGTCTTAGCAGGTTAGCTAGTCCA
TACTAGCCCTGTTATATGGCGTTTTGGACTAGTGAAGTTCAAGTAATATA
ACTATGATCGTAGAGGTCAGTGACGAGATGCGTTTGGACAGCGGGTTCAA
CTCCCGCCAGCTCCACCA

TABLE 23 tmDNA Sequence for *Staphylococcus epidermidis*

(SEQ ID NO: 31)

GGGGCTGATTCTGCATTCGACAGGGGTCCCCGAGCTTATTAAGCGTGTGG
AGGGTTGGCTCCGTCATCAACACATTTCGGTTAAATATAACTGACAAATC
AAACAATAATTTCGCAGTAGCTGCGTAATAGCCACTGCATCGCCTAACAG
CATCTCCTACGTGCTGTTAACGCGATTCAACCCTAGTAGGATATGCTAAA
CACTGCCGCTTGAAGTCTGTTTAGATGAAATATAATCAAGCTAGTATCAT
GTTGGTTGTTTATTGCTTAGCATGATGCGAAAATTATCAATAAACTACAC
ACGTAGAAAGATTTGTATCAGGACCTCTGGACGCGGGTTCAACTCCCGCC
AGCTCCACCA

TABLE 24

| tmDNA Sequence for *Streptococcus faecium* |
|---|
| (SEQ ID NO: 32) |
| GGGGCTGATTCTGGATTCGACAGGCACAGTTTGAGCTTGAATTGCGTTTC<br>GTAGGTTACGTCTACGTTAAAACGTTACAGTTAAATATAACTGCTAAAAA<br>CGAAAACAACTCTTACGCTTTAGCTGCCTAAAAACAGTTAGCGTAGATCC<br>TCTCGGCATCGCCCATGTGCTCGAGTAAGGGTCTCAAATTTAGTGGGATA<br>CGTGACAACTTTCCGTCTGTAAGTTGTTAAAGAGATCATCAGACTAGCGA<br>TACAGAATGCCTGTCACTCGGCAAGCTGTAAAGCGAAACCACAAATGAGT<br>TGACTATGAACGTAGATTTTTAAGTGGCGATGTGTTTGGACGCGGGTTCA<br>ACTCCCGCCGTTCCACCA |

TABLE 25

| tmDNA Sequence for *Thermoanaerobacterium saccharolyticum* (*Bacillus/clostridium*) |
|---|
| (SEQ ID NO: 33) |
| GGGGTAGTAGAGGTAAAAGTAGCGAGCCGAGGTTCCATCTGCTCGTAAAA<br>CGGTGGACTTAAATATAAACGCAAACGATAATTTAGCTTACGCTGCTTAA<br>TTACAAGCAGCCGTTCAACCTTTGATTCCCACATCAAAGGATTGGGCGTC<br>GATTTAGTGGGGAACTGATTTATCAAAGCTTTGAGATAAATCGGATTTTA<br>TGAAGCTACCAAAGCAGTTATCCTGTCACTGGGAGAACTGCAGAGGGAAT<br>GTCAAAACAGTGACTGCGCTCGGAGAAGCTTTTACTGTGACACCTTCGGA<br>CCGGGGTTCAACTCCCGCCAGCTCCACCA |

TABLE 26

| tmDNA Sequence for *Mycoplasma fermentans* |
|---|
| (SEQ ID NO: 34) |
| GGGGCTGATTCTGGATTCGACATGCATTGGGTGATACTAATATCAGTAGT<br>TTGGCAGACTATAATGCATCTAGGCTTTATAATCGCAGAAGATAAAAAAG<br>CAGAAGAAGTTAATATTTCTTCACTTATGATTGCACAAAAAATGCAATCA<br>CAATCAAACCTTGCTTTCGCTTAGTTAAAAGTGACAAGTGGTTTTAAAGT<br>TGACATTTTCCTATATATTTTAAAATCGGCTTTTAAGGAGAACAGGAGTC<br>TGAAAGGGTTCCAAAAATCTATATTGTTTGCATTTCGGTAGTATAGATTA<br>ATTAGAAATGATAAACTGTAAAAAGTATTGGTATTGACTTGGTGTGTGGA<br>CTCGGGTTCAACTCCCGCCAGCTCCACCA |

TABLE 27

| tmDNA Sequence for *Mycoplasma hyorhinis* |
|---|
| (SEQ ID NO: 35) |
| GGGGCTGATTCTGGATTCGACATACATAAAAGGATATAAATTGCAGTGGT<br>CTTGTAAACCATAAGACAATTTCTTTACTAAGCGGAAAAGAAAACAAAAA<br>AGAAGATTATTCATTATTAATGATTGCTTCAACTCAATCAAATCTAGCTT<br>TTGCATTTTAAAAAACTAGTAGACCAATTTGCTTCTCACGAATTGTAATC<br>TTTATATTAGAGAATAGTTAAAAATCTGATCACTTTTTAATGAATTTATA<br>GATCACAGGCTTTTTTAATCTTTTTGTTATTTTAGATAAAGAGTCTTCTT<br>AAAAATAACTAAACTGTAGGAATTTATATTTAATTATGCGTGGACCCGGG<br>TTCAACTCCCGCCAGCTCCACCA |

TABLE 28

| tmDNA Sequence for *Mycoplasma pirum* |
|---|
| (SEQ ID NO:36) |
| GGGGAGTCATGGTTTTGACATGAATGATGGACCCATAGAGGCAGTGGGGT<br>ATGCCCCTTATAGCTCAAGGTTTAAATTAACCGACAAAACTGACGAAAAC<br>GTTGCCGTTGATACAAATTTATTAATCAACCAACAAGCTCAATTTAACTA<br>CGCATTTGCATAGTATAAAAAAATAAATTGTGCTACTCATTGTAATTAGG<br>TTACTAAATTACTTTGTTTTATATAGTCCTGTAACTAGTTCTAGTGATGT<br>CTATAAACTAGAATGAGATTTATAGACTTATTTGTTGGCGGTTGTGCCAT<br>AGCCTAAATCAACAAAGACAATTTATTTATGGTACTAAACTGTAGATTCT<br>ATGATGAAATTATTTGTGGAAACGGGTTCGATTCCCGCCATCTCCACCA |

TABLE 29

| tmDNA Sequence for *Mycoplasma salivarium* |
|---|
| (SEQ ID NO: 37) |
| GGGGCTGATTCTGGATTCGACAGGCATTCGATTCATTATGTTGCAGTGGT<br>TTGCAAACCATAAGGCACTAGGCTTTTTTAAACGCAAAAGACCAAAAAAC<br>AGAAGATCAAGCAGTTGATCTAGCATTTATGAATAATTCACAAATGCAAT<br>CAAATCTAGTTTTCGCTTAGTAAAATTAGTCAATTTATTATGGTGCTCAA<br>CATAATAAATGGTAGTATGAGCTTAATATCATATGATTTTAGTTAATATG<br>ATAGGATTTGTAACTAAACTATGTTATAGAAATTTGTAAATTATATATAT<br>GACATAGGAAATTTAATTTACTAAACTGTAGATGCATAATGTTGAAGATG<br>TGTGGACCGGGGTTCAACTCCCGCCAGCTCCACCA |

TABLE 30

| tmDNA Sequence for *Herpetosiphon aurantiacus* |
|---|
| (SEQ ID NO: 38) |
| GGGGGCGGAAAGGATTCGACGGGGAGGGCCAATCGTAAGTGGCAAGCCGA<br>GACGCTGAGCCTCGTTAAATCGGCAACGCCATTAACTGGCAAAAACACTT<br>TCCGCGCTCCTGTAGCGCTTGCTGCCTAATTAAGGCAACACGTCTCTACT<br>AGCCTCAGCCCGATGGGCTTGTAGCGGCGACACTTAGTCGGGTCGCTCCC<br>CTAGTTATGTCTGTGGGCTAGGGGCTAAGATTAACAGGCTGGTCGTGGCC<br>CGCTTTGTCTATCGGGTGGTGCACCGATAAGATTTAATCAATAGACTACG<br>CTTGTAGATGCTTGCGGTTTAACTTTTTGGACGCGGGTTCGATTCCCGCC<br>GCCTCACCACCA |

TABLE 31

| tmDNA Sequence for *Thermomicrobium roseum* (352 nts, temp. 70 degrees, green non sulfur) |
|---|
| (SEQ ID NO: 39) |
| GGGGCTGATTCTGGATTCGACAGGGCCGTAGGTGCGAGGATTGCAGGTCG<br>AGGTCGCCCACGAACTCGTAAAAAGGGGCAGCCAAGTAACTGGCGAGCGC<br>GAACTCGCTCTGGCTGCGTAATTCACGCAGCCACGTCTGCCCGGACCCTT<br>CCCTGGTGGGTTCGGAGCGGGCGCCGCAAGACCGGGGTGCCCCTGGCCCA<br>AGCGCCGGTGCGGGCCAGGTCAAGCGTGATCCGGCTCGGCTGACCGGGAT<br>CCTGTCGGTGGGAGCCTGGCAGCGACAGTAGAACACCGACTAAGCCTGTA<br>GCATATCCTCGGCTGAACGCTCTGGACGCGGGTTCAACTCCCGCCAGCTC<br>CACCA |

TABLE 32

| tmDNA Sequence for *Chlorobium limicola* |
|---|
| (SEQ ID NO: 40) |
| GGGGCTGATTCTGGATTCGACAGGATACGTGTGAGATGTCGTTGCACTCC<br>GAGTTTCAGCATGGACGGACTCGTTAAACAAGTCTATGTACCATTAGATG<br>CAGACGATTATTCGTATGCAATGGCTGCCTGATTAGCACAAGTTAACTCA<br>GACGCCATCGTCCTGCGGTGAATGCGCTTACTCTGAAGCCGCCGGATGGC<br>ATAACCCGCGCTTGAGCCTACGGGTTCGCGCAAGTAAGCTCCGTACATTC<br>ATGCCCGAGGGGCTGTGCGGGTAATTTCTCGGGATAAGGGGACGAACGCT<br>GCTGGCGGTGTAATCGGCCCACGAAAACCCAATCACCAGAGATGAGTGTG<br>GTGACTGCATCGAGCAGTGTTTTGGACGCGGGTTCAACTCCCGCCAGCTC<br>CACCA |

TABLE 33

| tmDNA Sequence for *Pirellula staleyi* (*planctomyces*) |
|---|
| (SEQ ID NO: 41) |
| GGGGCTGATTCTGGATTCGACCGGATAGCCTGAAGCGAATACGGCGTGCC<br>GTGGTTGATCAGATGGCCACGTAAAAAGCTGATCACAAACTTAACTGCCG<br>AGAGCAATCTCGCACTTGCTGCCTAACTAAACGGTAGCTTCCGACTGAGG<br>GCTTTAGCCGGAGAGGCCCAAAAGTTGGTCACCAAATCCGGACCGCCTCG<br>TGCCATGATCGAAACGCACGAGGTCAAAAAAGTTTCGATCTAGTGCAGGG |

TABLE 33-continued

| tmDNA Sequence for *Pirellula staleyi* (*planctomyces*) |
|---|
| TGTAGCCAGCAGCTAGGCGACAAACTGTGCAAAAATCAAATTTTCTGCTA |
| CGCACGTAGATGTGTTCGTGAAAATGTCTCGGGACGGGGGTTCAACTCCC |
| GCCACTCCACCA |

TABLE 34

| tmDNA Sequence for *Planctomyces limnophilus* |
|---|
| (SEQ ID NO: 42) |
| GGGGCTGATTCTGGATTCGACAACCTCTCAAGAGGAGCGTGGCCACTATG |
| GGACTCGATTATGTTGAATTCGTCATGGATCTTGAAGAGACCTTCGACAT |
| CAAACTGGATGACAAACATTTTTCAGCAGTCAAAACACCACGCGATTTGG |
| CAATCATTATTCGGGATCAATTAGCTGCTGAAGGCAGAATCTGGGATGAA |
| TCGAATGCTTTTCGCAAAATCTCGAATTTGAATTGGACGATGTTGCCCGA |
| GTTCCGGATGTGGACTCAAATCAAAAGCTCTCTACCAGTTTCTTTTCACC |
| GACTGCGTCCCAGCACCCGTCTCGTTCAACTCCCGCCANTCCACCA |

TABLE 35

| tmDNA Sequence for *Planctomyces maris* |
|---|
| (SEQ ID NO: 43) |
| GGGGCTGATTCTGGATTCGACTGGTTCACCGTATGTTAAGGTGGCGGTGC |
| CGTGGTTGATCAGTTGGCCACGTAAAAAGCTGATCACAATCTAATTGCAA |
| ACAAGCAATTTTCAATGGCTGCTTAATAAAAGCAACCCCGGCTTAGGAAT |
| CTCTGTCTGAGGAGTCCGACAGCTGGTCACAAAATCAGACTGGTATCAGA |
| TCAATGTCCGCTCCGTCTGATACGAGATTCGTGGTGGACTGGTTTCCAAC |
| AGGCTCTGTTTATCGTGCCCGAAGAAACGAGACTCAAACGATAAAATATG |
| CACCGTAGAGGCTTTAGCTGAGGGTTCACAGGACGCGGGTTCAACTCCCG |
| CCAGCTCCACCA |

TABLE 36

| tmDNA Sequence for *Alcaligenes eutrophus* |
|---|
| (SEQ ID NO: 44) |
| GGGGTTGATTCTGGATTCGACGTGGGTTACAAAGCAGTGGAGGGCATACC |
| GAGGACCCGTCACCTCGTTAATCAATGGGAATGCAATAACTGCTAACGAC |
| GAACGTTACGCACTGGCCGCTTAATTGCGGCCGTCCTCGCACTGGCTCGC |
| TGACGGGCTAGGGTCGCAAGACCACGCGAGGTCATTTACGTCAGATAAGC |
| TCCGGAAGGGTCACGAAGCCGGGGACGAAAACCTAGTGACTCGCCGTCGT |
| AGAGCGTGTTCGTCCGCGATGCGCCGGTTAAATCAAATGACAGAACTAAG |
| TATGTAGAACTCTCTGTGGAGGGCTTACGGACGCGGGTTCAACTCCCGCC |
| AGCTCCACCA |

TABLE 37

| tmDNA Sequence for *Alcaligenes faecalis* (beta proteobacteria) |
|---|
| (SEQ ID NO: 45) |
| GGGGGCGGAAAGGATTCGACGGGGGTCAAGAAGCAGCACAGGGCGTGTCG |
| AGCACCAGTACGCTCGTAAATCCACTGGAAAACTATAAACGCCAACGACG |
| AGCGTTTCGCTCTAGCCGCTTAAGGCTGGGCCACTGCACTAATTTGTCTT |
| TGGGTTAGGTAGGGCAACCTACAGCAGTGTTATTTACAAAGAATCGAATC |
| GGTCTGCGCCACGAAGTCCGGTTCTAAAACTTAGTGGATCGCCAAGGAAA |
| GGCCTGTCAATTGGCATAGTCCAAGGTTAAAACTTAAAATTAATTGACTA |
| CACATGTAGAACTGTCTGTGGACGGCTTGCGGACGGGGGTTCGATTCCCG |
| CCGCCTCCACCA |

TABLE 38

| tmDNA Sequence for *Chromobacterium violaceum* (beta-purple) |
|---|
| (SEQ ID NO: 46) |
| GGGGCTGATTCTGGATTCGACGGGGGTTGCGAAGCAGATGAGGGCATACC |
| GGGATTTCAGTCACCCCGTAAAACGCTGAATTTATATAGTCGCAAACGAC |
| GAAACTTACGCTCTGGCAGCCTAACGGCCGGCCAGACACTACAACGGTTC |
| GCAGATGGGCCGGGGGCGTCAAAACCCTGTAGTGTCACTCTACATCTGCT |
| AGTGCTGTTCCGGGTTACTTGGTTCAGTGCGAAATAATAGGTAACTCGCC |
| AAAGTCCAGCCTGTCCGTCGGCGTGGCAGAGGTTAAATCCAAATGACACG |
| ACTAAGTATGTAGAACTCACTGTAGAGGACTTTCGGACGCGGGTTCAACT |
| CCCGCCAGCTCCACCA |

TABLE 39

| tmDNA Sequence for *Hydrogenophaga palleroni* (beta-purple) |
|---|
| (SEQ ID NO: 47) |
| GGGGCTGATTCTGGATTCGACGTGGGTTCGGACGCGCAGCAGGGCATGTC |
| GAGGTTCTGTCACCTCGTAAATCAGCAGAAAAAAACCAACTGCAAACGAC |
| GAACGTTTCGCACTCGCCGCTTAAACACCGGTGAGCCTTGCAACAGCAGG |
| CCGATGGGCTGGGCAAGGGGGTCGCAAGACCTCCCGGCTGCAAGGTAATT |
| TACATCGGCTGGTTCTGCGTCGGGCACCTTGGCGCAGGATGAGATTCAAG |
| GATGCTGGCTTCCCGTTTAGCGTGCCACTGCGCGACTCGGGCGGCGAGAC |
| CCAAATCAGACGGCTACACATGTAGAACTGCTCGAAAAAGGCTTGCGGAC |
| GGGGGTTCAACTCCCGCCAGCTCCACCA |

TABLE 40

| tmDNA Sequence for *Methylobacillus glycogenes* (beta-purple) |
|---|
| (SEQ ID NO: 48) |
| GGGGGCGGAAAGGATTCGACGGGGGTTGCAAAGCAGCGCAGGGCATACCG |
| AGGCCTAGTCACCTCGTAAATAAACTAGAACAAGTATAGTCGCAAACGAC |
| GAAACTTACGCTCTAGCCGCTTAATCCCGGCTGGACGCTGCACCGAAGGG |
| CCTCTCGGTCGGGTGGGGTAACCCACAGCAGCGTCATTAAGAGAGGATCG |
| TGCGATATTGGGTTACTTAATATCGTATTAAATCCAAGGTAACTCGCCTG |
| CTGTTTGCTTGCTCGTTGGTGAGCATCAGGTTAAATCAAACAACACAGCT |
| AAGTATGTAGAACTGTCTGTGGAGGGCTTGCGGACGGGGGTTCGATTCCC |
| GCCGCCTCACCACCA |

TABLE 41

| tmDNA Sequence for *Nitrosomonas cryotolerans* (beta-purple) |
|---|
| (SEQ ID NO: 49) |
| GGGGCTGATTCTGGATTCGACGTGGGTTGCAAAGCAGCGCAGGGCATACC |
| GAGGACCAGAATACCTCGTAAATACATCTGGAAAAAAATAGTCGCAAACG |
| ACGAAAACTACGCTTTAGCCGCTTAATACGGCTAGCCTCTGCACCGATGG |
| GCCTTAACGTCGGGTCTGGCAACAGACAGCAGAGTCATTAGCAAGGATCG |
| CGTTCTGTAGGGTCACTTTACAGAACGTTAAACAATAGGTGACTCGCCTG |
| CCATCAGCCCGCCAGCTGGCGGTTGTCAGGTTAAATTAAAGAGCATGGCT |
| AAGTATGTAGAACTGTCTGTAGAGGACTTGCGGACGCGGGTTCAACTCCC |
| GCCAGTCCACCA |

TABLE 42

| tmDNA Sequence for *Pseudomonas testosteroni* |
|---|
| (SEQ ID NO: 50) |
| GGGGCTGATTCTGGATTCGACGTGGGTTCGGGACCGGTGCGGTGCATGTC |
| GAGCTTGAGTGACGCTCGTAAATCTCCATTCAAAAAACTAACTGCAAACG |
| ACGAACGTTTCGCACTCGCCGCTTAATCCGGTGAGCCTTGCAACAGCACG |
| CTAGTGGGCTGGGCAAGGGGGTAGCAATACCTCCCGGCTGCAAGGGAATT |
| TTCATTAGCTGGCTGGATACCGGGCTTCTTGGTATTTGGCGAGATTTTAG |
| GAAGCTGGCTACCCAAGCAGCGTGTGCCTGCGGGGTTTGGGTGGCGAGAT |

TABLE 42-continued

| tmDNA Sequence for *Pseudomonas testosteroni* |
|---|
| TTAAAACAGAGCACTAAACATGTAGATCTGTCCGGCGAAGGCTTACGGAC |
| GCGGGTTCAACTCCCGCCAGCTCCACCA |

TABLE 43

| tmDNA Sequence for *Ralstonia pickettii* (*Burkholderia*) |
|---|
| (SEQ ID NO: 51) |
| GGGGGCGGAAAGGATTCGACGGGGGTTGCGAAGCAGCGGAGGGCATACCG |
| AGGACCCGTCACCTCGTTAATCAATGGGAATGCAATAACTGCTAACGACG |
| AACGTTACGCACTGGCAGCCTAAGGGCCGCCGTCCTCGCACTGGCTCGCT |
| GACGGGCTAGGGTCGCAAGACCAGCGAGGTCATTTACGTCAGATAAGCTT |
| TAGGTGAGTCACGGGCCTAGAGACGAAAACTTAGTGAATCGCCGTCGTAG |
| AGCGTGTTCGTCCGCGATGCGGCGGTTAAATCAAATGACAGAACTAAGTA |
| TGTAGAACTCTCTGTGGAGGGCTTGCGGACGCGGGTTCGATTCCCGCCGC |
| CTCACCACCA |

TABLE 44

| tmDNA Sequence for *Variovax paradoxus* (*pseudomonas* sp.) |
|---|
| (SEQ ID NO: 52) |
| GGGGCTGATTCTGGATTCGACGTGGGTTCGGAGTCGCAGCGGGGCATGTC |
| GAGCTGAATGCGCTCGTAAAACAGATTCAAACAAACTAACTGCAAACGAC |
| GAACGTTTCGCACTCGCTGCTTAATTGCCAGTGAGCCTTGCAACAGTTGG |
| CCGATGGGCTGGGCAAGGGGGTCTGGAGCAATCCTGACCTCCCGGCTGCA |
| AGGATAACTACATGGGCTGGCTCCGATCCGGGTACCTTGGGTCGGGGCGA |
| GAAAATAGGGTACTGGCGTCCGGTTTAGCGTGTGACTGCGCGACTCCGGA |
| AGCGAGACTCAAAACAGATCACTAAACATGTAGAACTGCGCGATGAAGGC |
| TTGCGGACGGGGGTTCAACTCCCGCCAGCTCCACCA |

TABLE 45

| tmDNA Sequence for *Bdellovibrio bacteriovorus* (delta proteobacterie) |
|---|
| (SEQ ID NO: 53) |
| GGGGGCGGAAAGGATTCGACGGGGGTGCTGAAGCATAAGGAGCATACCGG |
| GGCGGATGAGGACCTCGTTAAAAACGTCCACTTTGTAATTGGCAACGATT |
| ACGCACTTGCAGCTTAATTAAGCAGCACGATCAACCTTGTGGTGGTTCCG |
| CACTTGGATTGATCGTCATTTAGGGACCTCGGCGTGTTGGGTTTTCTCCA |
| GCAGACATGCTTAAATTTACTGGGGGAGAGGTCTTAGGGATTTTGTCTGT |
| GGAAGCCCGAGGACCAATCTAAAACACTGACTAAGTATGTAGCGCCTTAT |
| CGTGGATCATTTGCGGACGGGGGTTCGATTCCCGCCGCCTCCACCA |

TABLE 46

| tmDNA Sequence for *Myxococcus xanthus* (delta proteobacterie) |
|---|
| (SEQ ID NO: 54) |
| GGGGGCGGAAAGGATTCGACGGGGGCATTGAAGTTCGAGACGCGTGCCGA |
| GCTTGTCAGGTAGCTCGTAAATTCAACCCGGCAAAGACACAAAAGCCAAC |
| GACAACGTTGAGCTCGCGCTGGCTGCCTAAAAACAGCCCATAGTGCGCGG |
| TCCCCCCGCCCTCGGCCTGTGGGGTTGGGACAGACCGTCATAATGCAGGC |
| TGGCTGCCGAGGGTGCCTGGACCCGAGGTGGCGAGATCTTCCCAGGACCG |
| GCTCTGAGTATCCCGTCCGTGGGAGCCTCAGGGACGTAGCAAATCGCGGA |
| CTACGCACGTAGGGTCGAAGAGCGGACGGCTTTCGGACGCGGGTTCGATT |
| CCCGCCGCCTCCACCA |

TABLE 47

| tmDNA Sequence for *Sulfurospirillum Deleyianum* |
|---|
| (SEQ ID NO: 55) |
| GGGGCTGATTCTGGATTCGACAGGAGTAGTTTTAGCTTATGGCTGCATGT |
| CGGGAGTGAGGGTCTTCCGTTACACAACCTTCAAACAATAACTGCTAACA |
| ACAGTAACTATCGTCCTGCTTACGCGCTAGCTGCGTAAGTTTAACAAATA |
| ATGGACTGCTCTCCCCTTTGATGCTATCTTAGGAGGTCTTGGAGAGTATC |
| ATAGATTTGATAGCTATATTACATGAACGCCTTTACATGTAATGAAGTTA |
| AAGGCTCGTTTTGCGTAGTTTTCTGATTGTTGTACGAAGCAAAATTAAAC |
| ACTATCAACAATATCTAAGCATGTAGACGTCATAGGTGGCTATTTTTGGA |
| CTGCGGGTTCAACTCCCGCCAGCTCCACCA |

TABLE 48

| tmDNA Sequence for *Chromatium vinosum* |
|---|
| (SEQ ID NO: 56) |
| GGGGCTGATTCTGGATTCGACGTGGGTCGCGAAACCTAAGGTGCATGCCG |
| AGGTGCGGTTGACCTCGTAAAACCCTCCGCAAACTTATAGTTGCCAACGA |
| CGACAACTACGCTCTCGCTGCTTAATCCCAGCGGGCCTCTGACCGTCACT |
| TGCCTGTGGGCGGCGGATTCCAGGGGTAACCTCACACAGGATCGTGGTGA |
| CGGGAGTCCGGACCTGATCCACTAAAACCTAACGGAATCGCCGACTGATC |
| GCCCTGCCCTTCGGGCGGCAGAAGGCTAAAAACAATAGAGTGGGCTAAGC |
| ATGTAGGACCGAGGGCAGAGGGCTTGCGGACGCGGGTTCAACTCCCGCCA |
| GCTCCACCA |

TABLE 49

| tmDNA Sequence for *Pseudomonas fluorescens* (gamma proteobacteria) |
|---|
| (SEQ ID NO: 57) |
| GGGGCTGATTCTGGATTCGACGCCGGTTGCGAACCTTTAGGTGCATGCCG |
| AGTTGGTAACAGAACTCGTAAATCCACTGTTGCAACTTTCTATAGTTGCC |
| AATGACGAAACCTACGGGGAATACGCTCTCGCTGCGTAAGCAGCCTTAGC |
| CCTTCCCTCCTGGTACCTTCGGGTCCAGCAATCATCAGGGGATGTCTGTA |
| AACCCAAAGTGATTGTCATATAGAACAGAATCGCCGTGCAGTACGTTGTG |
| GACGAAGCGGCTAAAACTTACACAACTCGCCCAAAGCACCCTGCCCGTCG |
| GGTCGCTGAGGGTTAACTTAATAGACACGGCTACGCATGTAGTACCGACA |
| GCAGAGTACTGGCGGACGCGGGTTCAACTCCCGCCAGCTCCACCA |

TABLE 50

| tmDNA Sequence for *Borrelia afzeli* |
|---|
| (SEQ ID NO: 58) |
| GGGGCTGATTCTGGATTCGACTGAAAATGCTAATATTGTAAGTTGCAAGC |
| AGAGGGAATCTCTTAAAACTTCTAAAATAAATGCAAAAAATAATAACTTT |
| ACAAGTTCAAACCTTGTAATGGCTGCTTAAGTTAGCAGAGAGTTTTGTTG |
| AATTTGGCTTTGAGATTCACTTATACTCTTTTAGACATCGAAGCTTGCTT |
| AAAAATGTTTTCAAGTTGATTTTTAGGGACTTTTATACTTGAGAGCAATT |
| TGGCGGTTTGCTAGTATTTCCAAACCATATTGCTTAGTAAAATACTAGAT |
| AAGCTTGTAGAAGCTTATAGTATTGTTTTTAGGACGCGGGTTCAACTCCC |
| GCCAGTCCACCA |

TABLE 51

| tmDNA Sequence for *Borrelia crociduarae* |
|---|
| (SEQ ID NO: 59) |
| GGGGCTGATTCTGGATTCGACTAAGAACTTTAGTAGCATAAATGGCAAGC |
| AGAGTGAATCTCTTAAAACTTCTTTAATAAATGCAAAAAATAATAACTTT |
| ACAAGTTCAGATCTTGTAATGGCTGCTTAATTTAGCAGAGAGTTTTGTTG |
| GATTTTGCTTTGAGGTTCAACTTATACTCTTTAAGACATCAAAGTATGCC |
| TAAAAATGTTTCAAGTTGATTTTTAGGGACCTTTAAACTTGAGAGTAATT |
| TGGTGGTTTGCTTGTTTTCCAAGCCTTATTGCTTTTTCTAAAAATTAGCT |
| AAGCTTGTAGATATTTATGATATTATTTTTAGGACGCGGGTTCAACTCCC |
| GCCAGTTCCACCA |

TABLE 52

| tmDNA Sequence for *Borrelia hermsii* |
| --- |
| (SEQ ID NO: 60) |
| GGGGCTGATTCTGGATTCGACTAAAAACTTTAGTAGCATAAATTGCAAGC |
| AGAGGGAATCTCTTAAAACTTCTTTAATAAATGCAAGAAATAATAACTTT |
| ACAAGTTCAAATCTTGTAATGGCTGCTTAAATTAGCAGAGAGTTCTGCTG |
| GATTTTGCTTTGAGGTTCAGCTTATACTCTTTTAAGACATCAAAGCTTGC |
| TTAAAAATATTTCAAGTTGATTTTTAGGGACTTTTAAATTTGAGAGTAAT |
| TTGGCGGTTTGCTAGTTTTTCCAAACCTTATTACTTAAAGAAAACACTAG |
| CTAAGCTTGTAGATATTTATGATATTATTTTTAGGACGCGGGTTCAACTC |
| CCGCCAGCTCCACCA |

TABLE 53

| tmDNA Sequence for *Borrelia garinii* |
| --- |
| (SEQ ID NO: 61) |
| GGGGCTGATTCTGGATTCGACTGAAAATGCGAATATTGTAAGTTGCAGGC |
| AGAGGGAATCTCTTAAAACTTCTAAAATAAATGCAAAAAATAATAACTTT |
| ACAAGCTCAAACCTTGTAATGGCTGCTTAAGTTAGCAGGGAGTTTCGTTG |
| AATTTGGCTTTGAGGTTCACTTATACTCTTTTCGATATCGAAGCTTGCTT |
| AAAAATGTTTTCAAGTTAATTTTTAGGGACTTTTGTACTTGAGAGCAATT |
| TGGCGGTTTGCTAGTATTTCCAAACCATATTGCTTAAGTAAAATGCTAGA |
| TAAGCTTGTAGAAGCTTATAATATTGTTTTTAGGACGCGGGTTCAACTCC |
| CGCCAGTCCACCA |

TABLE 54

| tmDNA Sequence for *Thermodesulfobacterium commune* (70 degrees) |
| --- |
| (SEQ ID NO: 62) |
| GGGGGCGGAAAGGATTCGACGGGGATAGGTAGGATTAAACAGCAGGCCGT |
| GGTCGCACCCAACCACGTTAAATAGGGTGCAAAAACACAACTGCCAACGA |
| ATACGCCTACGCTTTGGCAGCCTAAGCGTGCTGCCACGCACCTTTAGACC |
| TTGCCTGTGGGTCTAAAGGTGTGTGACCTAACAGGCTTTGGGAGGCTTAA |
| TCGGTGGGGTTAAGCCTCCCGAGATTACATCCCACCTGGTAGGGTTGCTT |
| GGTGCCTGTGACAAGCACCCTACGAGATTTTCCCACAGGCTAAGCCTGTA |
| GCGGTTTAATCTGAACTATCTCCGGACGCGGGTTCGATTCCCGCCGCCTC |
| CCCACCA |

TABLE 55

| tmDNA Sequence for *Thermotoga neapolitana* (*Thermotogales*) |
| --- |
| (SEQ ID NO: 63) |
| GGGGGCGGAAAGGATTCGACGGGGATGGAGTCCCCTGGGAAGCGAGCCGA |
| GGTCCCCACCTCCTCGTAAAAAAGGTGGGAACACGAATAAGTGCCAACGA |
| ACCTGTTGCTGTTGCCGCCTAATAGATAGGCGGCCGTCCTCTCCGGAGTT |
| GGCTGGGCTCCGGAAGAGGGCGTGAGGGATCCAGCCTACCGATCTGGGCT |
| CCGCCTTCCGGCCCGGATCGGGAAGGTTCAGGAAGGCTGTGGGAAGCGAC |
| ACCCTGCCCGTGGGGGTCCTTCCCGAGACACGAAACACGGGCTGCGCTC |
| GGAGAAGCCCAGGGGCCTCCATCTTCNGACGCGGGTTCGATTCCCGCCAC |
| CTCCACCA |

TABLE 56

| tmDNA Sequence for *Deinococcus proteolyticus* |
| --- |
| (SEQ ID NO: 64) |
| GGGGGCGGAAAGGATTCGACGGGGGAACGGAAAGCGCTGCTGCGTGCCGA |
| GGAGCCGTTGGCCTCGTAAACAAACGGCAAAGCCATTAACTGGCGAAAAT |
| AACTACGCTCTCGCTGCTTAAGTGAGACAGTGACCACGTAGCCCCGCCTT |
| TGGCGACGTGTGAACTGAGACAAAAGAAGGCTAGCTTAGGTGAGGTTCCA |
| TAGCCAAAAGTGAAACCAAATGGAAATAAGGCGGACGGCAGCCTGTTTGC |
| TGGCAGCCCAGGCCCGACAATTTAAGAGCAGACTACGCACGTAGATGCAC |
| GCTGGATGGACCTTTGGACGCGGGTTCGATTCCCGCCAGCTCCACCA |

TABLE 57

| tmDNA Sequence for *Prosthecobacter fusformis* (*verrucomicrobia*) |
| --- |
| (SEQ ID NO: 65) |
| GGGGCTGATTCTGGATTCGACGGGGAGTACAAGGATCAAAAGCTGCAAGC |
| CGAGGTGCCGTTACCTCGTAAAACAACGGCAAAAAAGAAGTGCCAACACA |
| AATTTAGCATTAGCTGCTTAATTTAGCAGCTACGCTCTTCTAACCCGGGC |
| TGGCAGGGTTAGAAGGGTGTCATAATGAGCCAGCTGCCCCTTCCGACTCC |
| CCTAAGGAAGGGAAAGATGTAGGGGATAGGTGCTTACAGAATCCTGCGGG |
| AGGGAGTCTGTAAGTGCCGAAAAGTTAAAACTCCCGCTAAGCTTGTAGAG |
| GCTTTTGATTCTTGCTCTCTGGACGCGGGTTCAACTCCCGCCAGCTCCAC |
| CA |

TABLE 58

| tmDNA Sequence for *Verrucomicrobium spinosum* (*verrucomicrobium*) |
| --- |
| (SEQ ID NO: 66) |
| GGGNNNNATTTGGAATTCGCCGAATGCTAGAAGTGGAGGCTGCATGCCGC |
| GGATGATTCGTTGGCCGCTTTACCAATTCGGATCAAACAACTAAATGCGG |
| ACTCTAACGAGCTTGCCCTCGCCGCTTAATTGACGGTGACGTTCCTCCAG |
| TGAAGTCTGTGAATTGGAGGAGCGACTACTTACAGGCTGGCCAAAAGAGC |
| GGGCGACCGGCCCCAAGGCGAGATCTACAGGCCGCTGGATGGACGGCATC |
| CTGGCAGTAGGAGGCTGGACATCGAGATCAAATNATTGCCTGAGCATGGA |
| GACGCTTTCATAAAGGNGTTCGGACAGGG |

Example 4

Alignment of tmRNA Sequences

The newly discovered tmRNA sequences and several known tmRNA sequences were aligned to identify target sites for drug development. The alignments of the sequences are shown in FIGS. 3A-11B. The nucleotides in the tmRNA sequences of these figures exist in several motifs (Felden et al., 1999). These motifs include nucleotides considered to be in RNA helices (Watson-Crick base-pairs GC or AU, or GU Wobble base-pairs). Nucleotides that are in single stranded RNA domains, hence not base-paired. Some nucleotides in the single stranded domains are universally conserved nucleotides. Other nucleotides are the exceptions to a quasi-sequence conservation in the sequences alignment. Several nucleotides exist in well established non-canonical structural motifs in RNA structures; for example AG-GA pairs, AA pairs, etc. Some nucleotides are universally conserved Wobble GU base-pairs.

All the gene sequences have been decomposed in several structural domains that have been indicated with names at the top of each block of sequences. These domains are respectively from the 5'-end to the 3'-end of the sequences: H1, H5, H2, PK1, H4, PK2, PK3, PK4, H5 and H6. The bars delineate all the structural domains. H means helices and PK means pseudoknot. A pseudoknot is made of the pairing of parts of an RNA-loop with an upstream sequence. Consequently, two helices are made (shown in Felden et al., 1999) for all the 4 pseudoknots PK1 to PK4 for each sequence. Moreover, the tRNA-like domain as well as the coding sequence, namely the two functional units of the molecule, have also been indicated for each sequence.

The sequences, especially as identified by the sequence alignment, represent targets for the development of drugs which may be broadly applicable to many kinds of bacteria, or may be broadly applicable only to a particular genera of phylum of bacteria, or may be specifically applicable to a single species of bacteria.

Common Structural Features for Drug Targeting:

For all the novel tmRNA sequences, as well as with the ones that are already known, there are systematically several structural domains that are always found. These domains can be used as targets for the development of drugs which may be genera specific or which may be eubacteria specific. These domains are either RNA helices which can be sometimes interrupted by bulges or pseudoknots. The RNA helices which are always present are H1, H2, H5 and H6. Helices H1 and H6 are found in all canonical transfer RNAs. Thus, H1 and H6 are not good targets for drug development because drugs that would target them will also interfere with the biology of the individual that has a given disease. Consequently, very good candidates for development of drugs for targeting as many bacteria as possible are helices H2 and H5. Moreover, helices H2 and H5 are critical for the folding of all these tmRNA since both of them connect the two ends of the molecule together. Disruption of either H2 or H5 with a specific drug would lead to inactive tmRNA molecules in vivo. Similarly, pseudoknots PK1, PK2 and PK3 are always found in the bacterial tmRNAs. The PK1 structural domain is strictly conserved in the tmRNAs and is located upstream of the coding sequence. Since these pseudoknots are not found in all canonial transfer RNAs, they can also be targeted with specific drugs. Disruption of either PK1 or PK2 or PK3 with a specific drug would lead to inactive tmRNA molecules in vivo.

Specific Structural Features in Each Phylum that could be Targeted by Drugs:

In addition to developing drugs which broadly target many bacteria, drugs are developed which are more genera specific. For trying to target specifically a given bacteria or a complete phylum, the coding sequence (shown in all the alignments) is a very good candidate. Indeed, this region of the RNA is very accessible for DNA antisense binding, which has been shown for *Escherichia coli*, and thus, is also available for interaction with other drugs. Moreover, this is a critical functional domain of the molecule in its quality-control mechanism in cells. In addition, this coding sequence would be the ideal target to use for designing specific PCR-based diagnostic assays for infection diseases.

Interestingly, some structural domains are present only in a given bacterial phyla and could be targeted for discovering a drug that will be specific of a phylum, but not of the others. For example:

(1) in the cyanobacteria, the fourth pseudoknot PK4 is made of two smaller pseudoknots called PK4a and PK4b;

(2) in the mycoplasma, helix H2 is made of only 4 base-pairs instead of 5 in the other species;

(3) for two sequences of chlorobium as well as *Bacteroides thetaiotaomicron* and ppm gingiv., there is an additional domain just downstream of the coding sequence that is unique to them;

(4) there is always a stem-loop in the coding sequence of the actinobacteria (Felden et al., 1999); and (5) all the beta proteobacteria possess a sequence insertion in pseudoknot PK2 (shown in the alignment).

The novel sequences described herein, when aligned, show that specific structural domains within tmRNA are strictly conserved, as for example pseudoknot PK1 is located upstream (at the 5'-side) of the coding sequence. As previously disclosed, this pseudoknot is a target for future antibacterial drugs. Moreover, recent data have shown that this PK1 pseudoknot, among all the four pseudoknots within tmRNA gene sequences (sometimes there's only 2 or 3 detectable pseudoknots, depending upon the sequences), is the only one that its correct folding is essential for the biological activity of tmRNA (Nameki et al., 1999; Nameki et al., 2000).

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Andersson, S. G. et al. (1998). *Nature* 396:133-140.
Ando, H. et al. (1996). *Genes & Genet. Syst.* 71:47-50.
Breithaupt, H. (1999). *Nature Biotechnol.* 17:1165-1169.
Felden, B. et al. (1996). *Biochimie* 78:979-983.
Felden, B. et al. (1997). *RNA* 3:89-103.
Felden, B. et al. (1998). *EMBO J.* 17:3188-3196.
Felden et al. (1999). *Biochim. Biophys. Acta* 1446:145-148.
Gray, M. W. and Spencer, D. F. (1996). In *Evolution of Microbial Life*, Cambridge University Press, pp. 109-126.
Hickerson, R. P. et al. (1998). *J. Mol. Biol.* 279:577-587.
Himeno, H. et al. (1997). *J. Mol. Biol.* 268:803-808.
Huang, C. et al. (2000). *EMBO J.* 19:1098-1107.
Julio, S. M et al. (2000). *J. Bacteriol.* 182:1558-1563.
Keiler, K. C. et al. (1996). *Science* 271:990-993.
Komine, Y. et al. (1994). *Proc. Natl. Acad. Sci. USA* 20:9223-9227.
Mateeva, O. et al. (1997). *Nucleic Acids Res.* 25:5010-5016.
Muto, A. et al. (1998). *Trends Biochem. Sci.* 1:25-29.
Nameki, N. et al. (1999). *J. Mol. Biol.* 286:733-744.
Nakemi, N. et al. (2000). *FEBS Lett.* 470:345-349.
*Remington's Pharmaceutical Sciences,* 18th Ed., Mack Publishing Co., Easton, Pa., 1990.
Tu, G. F. et al. (1995). *J. Biol. Chem.* 270:9322-9326.
Ushida, C. et al. (1994). *Nucleic Acids Res.* 16:3392-3396.
Williams, K. P. (1999). *Nucleic Acids Res.* 27:165-166.
Williams, K. P. and Bartel, D. P. (1996). *RNA* 2:1306-1310.
Wower, J. and Zwieb, C. (1999). *Nucleic Acids Res.* 27:167.
Yang, D. et al. (1985). *Proc. Natl. Acad. Sci. USA* 82:4443-4447.

What is claimed is:

1. An isolated nucleic acid sequence selected from the group consisting of a tmRNA sequence for *Pseudomonas aeruginosa*, a tmDNA sequence encoding said tmRNA sequence, and a full-length complement of said tmDNA sequence, wherein the tmRNA sequence for *Pseudomonas aeruginosa* has the sequence set forth in SEQ ID NO:158.

2. A method for diagnosing a bacterial infection associated with *Pseudomonas aeruginosa* comprising determining the presence of a bacterial nucleic acid sequence selected from the group consisting of a tmRNA sequence for *Pseudomonas aeruginosa*, a tmDNA sequence encoding said tmRNA sequence, and a full-length complement of said tmDNA sequence, wherein the tmRNA sequence for *Pseudomonas aeruginosa* has the sequence set forth in SEQ ID NO:158.

3. The method of claim 2, wherein the determination is made by performing an amplification-based assay.

4. The isolated nucleic acid sequence of claim 1, wherein the nucleic acid sequence is the tmDNA sequence encoding the tmRNA sequence for *Pseudomonas aeruginosa*.

5. The method of claim 2, wherein the bacterial nucleic acid sequence is the tmDNA sequence encoding the tmRNA sequence for *Pseudomonas aeruginosa*.

6. The method of claim 3, wherein the bacterial nucleic acid sequence is the tmDNA sequence encoding the tmRNA sequence for *Pseudomonas aeruginosa*.

* * * * *

SEQUENCE LISTING

```
<160> NUMBER OF SEQ ID NOS: 175

<210> SEQ ID NO 1
<211> LENGTH: 21
<212> TYPE: DNA
<213> ORGANISM: Artificial
<220> FEATURE:
```

-continued

<223> OTHER INFORMATION: PCR primer

<400> SEQUENCE: 1
ggggctgatt ctggattcga c 21

<210> SEQ ID NO 2
<211> LENGTH: 21
<212> TYPE: DNA
<213> ORGANISM: Artificial
<220> FEATURE:
<223> OTHER INFORMATION: PCR primer

<400> SEQUENCE: 2
tggagctggc gggagttgaa c 21

<210> SEQ ID NO 3
<211> LENGTH: 21
<212> TYPE: DNA
<213> ORGANISM: Artificial
<220> FEATURE:
<223> OTHER INFORMATION: PCR primer

<400> SEQUENCE: 3
gggggcggaa aggattcgac g 21

<210> SEQ ID NO 4
<211> LENGTH: 21
<212> TYPE: DNA
<213> ORGANISM: Artificial
<220> FEATURE:
<223> OTHER INFORMATION: PCR primer

<400> SEQUENCE: 4
tggaggcggc gggaatcgaa c 21

<210> SEQ ID NO 5
<211> LENGTH: 21
<212> TYPE: DNA
<213> ORGANISM: Artificial
<220> FEATURE:
<223> OTHER INFORMATION: PCR primer

<400> SEQUENCE: 5
ggggatgtca tggttttgac a 21

<210> SEQ ID NO 6
<211> LENGTH: 21
<212> TYPE: DNA
<213> ORGANISM: Artificial
<220> FEATURE:
<223> OTHER INFORMATION: PCR primer

<400> SEQUENCE: 6
tggagatggc gggaatcgaa c 21

<210> SEQ ID NO 7
<211> LENGTH: 21
<212> TYPE: DNA
<213> ORGANISM: Artificial
<220> FEATURE:
<223> OTHER INFORMATION: PCR primer

<400> SEQUENCE: 7
ggggatgaca ggctatcgac a 21

-continued

<210> SEQ ID NO 8
<211> LENGTH: 21
<212> TYPE: DNA
<213> ORGANISM: Artificial
<220> FEATURE:
<223> OTHER INFORMATION: PCR primer

<400> SEQUENCE: 8
tggagatggc gggacttgaa c 21

<210> SEQ ID NO 9
<211> LENGTH: 352
<212> TYPE: DNA
<213> ORGANISM: Acidobacterium capsulatum

<400> SEQUENCE: 9
gggggcggaa aggattcgac ggggttgact gcggcaaaga ggcatgccgg ggggtgggca 60
cccgtaatcg ctcgcaaaac aatacttgcc aacaacaatc tggcactcgc agcttaatta 120
aataagttgc cgtcctctga ggcttcgcct gtgggccgag gcaggacgtc atacagcagg 180
ctggttcctt cggctgggtc tgggccgcgg ggatgagatc cacggactag cattctgcgt 240
atcttgtcgc ttctaagcgc agagtgcgaa acctaaagga atgcgactga gcatggagtc 300
tcttttctga caccaatttc ggacgcgggt tcgattcccg ccgcctccac ca 352

<210> SEQ ID NO 10
<211> LENGTH: 353
<212> TYPE: DNA
<213> ORGANISM: Coprothermobacter proteolyticus

<400> SEQUENCE: 10
gggggcggaa aggattcgac ggggagtcgg agccttgagc tgcaggcagg gttggctgcc 60
acaccttaaa aagggtagca aggcaaaaat aaatgccgaa ccagaatttg cactagctgc 120
ttaatgtaag cagccgctct ccaaactgag gctgcataag tttggaagag cgtcaaccca 180
tgcagcggct cttaagcagt ggcaccagct gtttaagggt gaaaagagtg gtgctgggca 240
gtgcggttgg gcttcctggg ctgcactgtc gagacttcac aggagggcta agcctgtaga 300
cgcgaaaggt ggcggctcgt cggacgcggg ttcgattccc gccgcctcca cca 353

<210> SEQ ID NO 11
<211> LENGTH: 399
<212> TYPE: DNA
<213> ORGANISM: Bacteroides thetaiotaomicron

<400> SEQUENCE: 11
ggggctgatt ctggattcga cagcgggcag aaatggtagg taagcatgca gtgggtcggt 60
aatttccact taaatctcag ttatcaaaac tttatctggc gaaactaatt acgctcttgc 120
tgcttaatcg aatcacagta gattagctta atccaggcac taggtgccag gacgagacat 180
cactcggaag ctgttgctcc gaagcattcc ggttcagtgg tgcagtaaca tcggggatag 240
tcagaagcgg cctcgcgttt ttgatgaaac tttagaggat aaggcaggaa ttgatggctt 300
tggttctgct cctgcacgaa aatttaggca aagataagca tgtagaaagc ttatgatttc 360
ctcgtttgga cgagggttca actcccgcca gctccacca 399

<210> SEQ ID NO 12
<211> LENGTH: 352
<212> TYPE: DNA
<213> ORGANISM: Dictyoglomus thermophilum -continued

<400> SEQUENCE: 12
ggggctgatt ctggattcga cagggagtac aaggatcaaa agctgcaagc cgaggtgccg 60
ttacctcgta aaacaacggc aaaaaagaag tgccaacaca aatttagcat tagctgctta 120
atttagcagc tacgctcttc taacccgggc tggcagggtt agaagggtgt cataatgagc 180
cagctgcccc ttccgactcc cctaaggaag ggaaagatgt aggggatagg tgcttacaga 240
atcctgcggg agggagtctg taagtgccga aaagttaaaa ctcccgctaa gcttgtagag 300
gcttttgatt cttgctctct ggacgcgggt tcaactcccg ccagctccac ca 352

<210> SEQ ID NO 13
<211> LENGTH: 313
<212> TYPE: DNA
<213> ORGANISM: Artificial
<220> FEATURE:
<223> OTHER INFORMATION: sequence isolated from rumenal fluid

<400> SEQUENCE: 13
acgcccttgt ctcagacgag ggcactcgtt aaaaagtctg aaaagaataa ctgcagaacc 60
tgtagctatg gctgcttaat ttaagggcaa cccttggatc cgcctccatc ccgaaggggt 120
ggcatccgag tcgcaaatcg ggataggatg gatcttggca acgaggagta catccgaaat 180
ttgtcgctgc tggctgaagc atcgccgttc ctctttgggc gtggcaaggc aagattaaat 240
tcagaggata agcgtgtagt agcgagtgag taggtgtttt tggacgcggg ttcaagtccc 300
gccatctcca cca 313

<210> SEQ ID NO 14
<211> LENGTH: 350
<212> TYPE: DNA
<213> ORGANISM: Artificial
<220> FEATURE:
<223> OTHER INFORMATION: sequence isolated from sludge

<400> SEQUENCE: 14
ggggatgtca tggttttgac agggaaccag gaggtgtgag atgcatgccg gagacgctgt 60
ccgctccgtt atcaagcagc aaacaaaact aattgcaaac aacaattact ccttagcagc 120
gtaagcagct aacgttcaac ctctccggac cgccgggagg ggatttgggc gtcgaaacag 180
cgcggacgct ccggatagga cgcccataat atccggctaa gaccatgggt ctggctctcg 240
cgggtctgat tgtcttccac cgcgcgggcc gcgatcaaag acaactaagc atgtaggttc 300
ttgcatggcc tgttctttgg acgcgggttc gattcccgcc atctccacca 350

<210> SEQ ID NO 15
<211> LENGTH: 359
<212> TYPE: DNA
<213> ORGANISM: Fibrobacter succinogenes

<400> SEQUENCE: 15
ggggctgatt ctggattcga cagggttacc gaagtgttag ttgcaagtcg aggtctcaga 60
cgagggctac tcgttaaaaa gtctgaaaaa aaataagtgc tgacgaaaac tacgcactcg 120
ctgcctaatt aacggcaacg ccgggcctca ttccgctccc atcggggtgt acgtccggac 180
gcaatatggg atagggaagt gtcatgcctg ggggcatctc ccgagatttt ctaggctggt 240
caaactccgc gccgaccttc ttgggcgtgg ataagacgag atcttaaatt cgaagggaac 300
acttgtagga acgtacatgg acgtgatttt ggacaggggt tcaactcccg ccagctcca 359

-continued

<210> SEQ ID NO 16
<211> LENGTH: 350
<212> TYPE: DNA
<213> ORGANISM: Fusobacterium mortiferum

<400> SEQUENCE: 16

```
ggggctgatt ctggattcga cggggttatg aggttatagg tagcatgcca ggatgaccgc     60

tgtgagaggt caacacatcg tttagatgga aacagaaatt acgctttagc tgcttaatta    120

gtcagctcac ctctggtttc tctcttctgt aggagaatcc aaccgaggtg ttaccaatat    180

acagattacc tttagtgatt tctctaagct caaagggaca ttttagagaa tagcttcagt    240

tagccctgtc tgcgggagtg attgttgcga aataaaatag tagactaagc attgtagaag    300

cctatggcgc tggtagtttc ggacacgggt tcaactcccg ccagctccaa               350
```

<210> SEQ ID NO 17
<211> LENGTH: 377
<212> TYPE: DNA
<213> ORGANISM: Corynebacterium xerosis

<400> SEQUENCE: 17

```
ggggctgatt ctggattcga cttcgtacat tgagccaggg gaagcgtgcc ggtgaaggct     60

ggagaccacc gcaagcgtcg cagcaaccaa ttaagcgccg agaactctca gcgcgactac    120

gccctcgctg cctaagcagc gaccgcgtgt ctgtcagacc gggtaggcct ctgatccgga    180

ccctggcatc gtttagtggg gctcgctcgc cgacttggtc gcaagggtcg gcggggacac    240

tcacttgcga ctgggcccgt catccggtca tgttcgactg aaccggaggg ccgagcagag    300

accacgcgcg aactgcgcac ggagaagccc tggcgaggtg acggaggacc cgggttcaac    360

tcccgccagc tccacca                                                   377
```

<210> SEQ ID NO 18
<211> LENGTH: 372
<212> TYPE: DNA
<213> ORGANISM: Micrococcus luteus
<220> FEATURE:
<221> NAME/KEY: misc_feature
<222> LOCATION: (1)..(372)
<223> OTHER INFORMATION: n is an unknown base

<400> SEQUENCE: 18

```
ggggctattc tggattcgac ggtgtgtgtc gcgtcgggag aagcgggccg aggatgcaga     60

gtcatctcgt caaacgctct ctgcaaacca ataagtgccg aatccaagcg cactgacttc    120

gctctcgctg cctgatcagt gatcgagtcc gtcaccccga ggtcgctgtc gcctcggatc    180

gtggcgtcag ctagatagcc actgggcgtc accctcgccg gggtcgtga cgccgacatc     240

aatccggctg ggtccgggtt ggccgcccgt ctgcgggacg gccaggaccg agcaacaccc    300

acagcagact gcgcccggag aagacctggc aacacctcat cggacgcggg ttcaactccc    360

gcantcccac ca                                                        372
```

<210> SEQ ID NO 19
<211> LENGTH: 372
<212> TYPE: DNA
<213> ORGANISM: Mycobacterium smegmatis

<400> SEQUENCE: 19

```
tcatctcggc ttgttcgcgt gaccgggaga tccgagtaga gacatagcga actgcgcacg     60

gagaggggct gattcctgga ttcgacttcg agcatcgaat ccagggaagc gtgccggtgc    120
```

-continued aggcaagaga ccaccgtaag cgtcgttgca accaattaag cgccgattcc aatcagcgcg 180
actacgccct cgctgcctaa gcgacggctg gtctgtcaga ccgggagtgc cctcggcccg 240
gatcctggca tcagctagag ggacccaccc acgggttcgg tcgcgggacc tgtggggaca 300
tcaaacagcg actgggatcg agcctcgagg acatgccgta ggacccgggt tcaactcccg 360
ccagctccac ca 372

<210> SEQ ID NO 20
<211> LENGTH: 355
<212> TYPE: DNA
<213> ORGANISM: Bacillus badius

<400> SEQUENCE: 20
gggggtgatt ctggattcga cagggatagt tcgagcttgg gctgcgagcc ggagggccgt 60
cttcgtacca acgcaaacgc ctaaatataa ctggcaaaaa agatttagct ttagctgcct 120
aatataggtt cagctgctcc tcccgctatc gtccatgtag tcgggtaagg ggtccaaact 180
tagtggacta cgccggagtt ctccgcctgg ggacaaagga agagatcaat caggctagct 240
gcccggacgc ccgtcgatag gcaaaaggaa cagtgaaccc caaatatatc gactacgctc 300
gtagacgttc aagtggcgtt atctttggac gtgggttcaa ctcccgccag ctcca 355

<210> SEQ ID NO 21
<211> LENGTH: 357
<212> TYPE: DNA
<213> ORGANISM: Bacillus brevis

<400> SEQUENCE: 21
gggggcggaa aggattcgac ggggatggta gagcatgaga agcgagccgg ggggttgcgg 60
acctcgtcac caacgcaaac gccattaact ggcaacaaac aactttctct cgctgcttaa 120
taaccagtga ggctctccca ctgcatcggc ccgtgtgccg tggatagggc tcaactttaa 180
cgggctacgc cggaggcttc cgcctggagc caaaggaaga agaccaatca ggctaggtgc 240
caggtcagcg cgtcactccg cgaatctgtc accgaaactc taaacgagtg actgcgctcg 300
gagatgctca tgtatcgctg ttttcggacg ggggttcgat tcccgccgcc tcaccca 357

<210> SEQ ID NO 22
<211> LENGTH: 354
<212> TYPE: DNA
<213> ORGANISM: Bacillus thermoleovorans

<400> SEQUENCE: 22
gggggcggaa aggattcgac gggggtaggt cgagcttaag cggcgagccg agggggacgt 60
cctcgtaaaa acgtcaccta aagataactg gcaaacaaaa ctacgcttta gctgcctaat 120
tgctgcagct agctcctccc gccatcgccc gcgtggcgtt cgaggggctc atatggagcg 180
ggctacgccc aaatccgccg cctgaggatg agggaagaga cgaatcaggc tagccgccgg 240
gaggcctgtc ggtaggcgga acggacggcg aagcgaaata taccgactac gctcgtagat 300
gcttaagtgg cgatgcctct ggacgtgggt tcgattcccg ccgcctcccc acca 354

<210> SEQ ID NO 23
<211> LENGTH: 384
<212> TYPE: DNA
<213> ORGANISM: Clostridium innocuum

<400> SEQUENCE: 23
gggggcggaa aggattcgac ggggatatgt ctggtacaga ctgcagtcga gtggttacgt 60

-continued

```
aataaccaat taaatttaaa cggaaaaact aaattagcta acctctttgg tggaaaccag    120

agaatggctt tcgctgctta ataaccgata taggttcgca gccgcctctg catgcttctt    180

ccttgaccat gtggatgtgc gcgtaagacg caagggataa ggaatctggt ttgcctgaga    240

tcagattcac gaaaattctt caggcacatt catcagcgga tgttcatgac ctgctgatgt    300

cttaatcttc atggactaaa ctgtagaggt ctgtacgtgg ggctgtttct ggacaggagt    360

tcgattcccg ccgcctcacc acca                                           384


<210> SEQ ID NO 24
<211> LENGTH: 349
<212> TYPE: DNA
<213> ORGANISM: Clostridium lentocellum

<400> SEQUENCE: 24

gggggcggaa aggattcgac gggggtcaca tctactgggg cagccatccg tagaacgccg     60

gagtctacgt taaaagctgg cacttaaagt aaacgctgaa gataatttag caatcgctgc    120

ctaattaagg cgcagtcctc ctaggtcttc cgcagcctag atcagggctt cgactcgcgg    180

atccttcacc tggcaaagct ttgagccaac gtgaacacta tgaagctact aaaatctaga    240

gcctgtcttt gggcgctaga tggagggaat gtcaaaacaa agaatatgat ggtagagacc    300

acgctatatg ggctttcgga caggggttcg attcccgccg ccttcacca                349


<210> SEQ ID NO 25
<211> LENGTH: 358
<212> TYPE: DNA
<213> ORGANISM: Clostridium perfringens

<400> SEQUENCE: 25

ggggctgatt ctggattcga cgggggtaag atgggtttga taagcgagtc gagggaagca     60

tggtgcctcg ataataaagt atgcattaaa gataaacgca gaagataatt ttgcattagc    120

agcttaattt agcgctgctc atccttcctc aattgcccac ggttgagagt aagggtgtca    180

tttaaaagtg gggaaccgag cctagcaaag ctttgagcta ggaacggaat ttatgaagct    240

taccaaagag gaagtttgtc tgtggacgtt ctctgaggga attttaaaac acaagactac    300

actcgtagaa agtcttactg gtctgctttc ggacacgggt tcaactcccg ccactcca      358


<210> SEQ ID NO 26
<211> LENGTH: 362
<212> TYPE: DNA
<213> ORGANISM: Clostridium stercorarium

<400> SEQUENCE: 26

gggggcggaa aggattcgac ggggttattg aagcaagagt agcgggtaga ggattctcgt     60

tggcctcttt aaaaaacgag agctaaaaat aaacgcaaac aacgataact acgctttagc    120

tgctgcgtaa gtaacacgca gcccgtcggc cccggggttc ctgcgcctcg ggataccggc    180

gtcatcaagg cagggaacca gccggatcag gcttcaggtc cggtgggatt taatgaagct    240

accgacttat aaagcctgtc tctgggcgtt ataagaaggg aatgtcaaaa cagagactgc    300

acccggagaa gctcttgtgg atatggttcc ggacacgagt tcgattcccg ccgcctccac    360

ca                                                                   362


<210> SEQ ID NO 27
<211> LENGTH: 369
<212> TYPE: DNA
```

-continued

<213> ORGANISM: Enterococcus faecium
<220> FEATURE:
<221> NAME/KEY: misc_feature
<222> LOCATION: (1)..(369)
<223> OTHER INFORMATION: n is an unknown base

<400> SEQUENCE: 27
ggggctgatt atggattcga caggatngtt gagcttgaat tgcgtttcgt aggttacggc 60
tacgttaaaa cgttacagtt aaatataact gctaaaaacg aaaacaattc tttcgcttta 120
gctgcctaaa aaccagctag cgaagatcct cccggcatcg cccatgtgct cgggtcaggg 180
tcctaatcga agtgggatac gctaaatttt tccgtctgta aaatttagag gagcttacca 240
gactagcaat acaagaatgc ctgtcactcg gcacgctgta aagcgaacct ttaaatgagt 300
gtctatgaac gtagagattt aagtgggaat atgttttgga cgcgggttca actcccgcca 360
gctccacca 369

<210> SEQ ID NO 28
<211> LENGTH: 353
<212> TYPE: DNA
<213> ORGANISM: Heliobacillus mobilis

<400> SEQUENCE: 28
ggggctgatt ctggattcga cggggaacgt gtttgcttgg gatgcgagcc gggttgccgc 60
caggaccgta aaaagggcgg aaggctttaa ttgccgaaga taactacgct ttagctgctt 120
aattgcagtc taacctcttc tcctctgtgc tctcggtgag gatgtaaggg gtcatttaag 180
agagctggct tcgaccaatt ctcggaggtc caagcgagat ttatcgagat agcctgacca 240
acgctctgtc tgccgtgcgg aaggaaggcg aaatctaaaa cgacagacta cgctcgtagt 300
gtcctttgtg ggcatttctt cggacgcggg ttcaactccc gccagctcca cca 353

<210> SEQ ID NO 29
<211> LENGTH: 353
<212> TYPE: DNA
<213> ORGANISM: Heliospirillum gestii

<400> SEQUENCE: 29
ggggctgatt ctggattcga cggggaacgt gtttgcttag gacgcgagcc gggttgccgc 60
caggaccgta aaaagggcgg aaggctttaa ttgccgaaga taactacgct ttagctgctt 120
aattgcagtc taacctcttc tcctctgtgc tctcggtgag gatgtaaggg gtcatttaag 180
agagctggct cgaaccaatt ctcggaggtt cgggtaagac ttatcgagat agcctgacca 240
acgctctgtc tgccgtgcgg aaggatggcg aaatctaaaa cgacagaata cgctcgtagt 300
gtcctttgtg ggcatttctt cggacgcggg ttcaactccc gccagctcca cca 353

<210> SEQ ID NO 30
<211> LENGTH: 368
<212> TYPE: DNA
<213> ORGANISM: Lactobacillus acidophilus

<400> SEQUENCE: 30
ggggctgatt ctggattcga caggcgtaga cccgcattga ctgcggttcg taggttacgt 60
ctacgtaaaa acgttacagt taaatataac tgcaaataac aaaaattctt acgcattagc 120
tgcttaattt agcgcatgcg ttgctctttg tcggtttact cgtggctgac actgagtatc 180
aacttagcga gttacgttta actacctcac ctgaatagtt gaaaagagtc ttagcaggtt 240
agctagtcca tactagccct gttatatggc gttttggact agtgaagttc aagtaatata 300

-continued

```
actatgatcg tagaggtcag tgacgagatg cgtttggaca gcgggttcaa ctcccgccag    360

ctccacca                                                             368
```

<210> SEQ ID NO 31
<211> LENGTH: 360
<212> TYPE: DNA
<213> ORGANISM: Staphylococcus epidermidis

<400> SEQUENCE: 31

```
ggggctgatt ctgcattcga caggggtccc cgagcttatt aagcgtgtgg agggttggct     60

ccgtcatcaa cacatttcgg ttaaatataa ctgacaaatc aaacaataat ttcgcagtag    120

ctgcgtaata gccactgcat cgcctaacag catctcctac gtgctgttaa cgcgattcaa    180

ccctagtagg atatgctaaa cactgccgct tgaagtctgt ttagatgaaa tataatcaag    240

ctagtatcat gttggttgtt tattgcttag catgatgcga aaattatcaa taaactacac    300

acgtagaaag atttgtatca ggacctctgg acgcgggttc aactcccgcc agctccacca    360
```

<210> SEQ ID NO 32
<211> LENGTH: 368
<212> TYPE: DNA
<213> ORGANISM: Streptococcus faecium

<400> SEQUENCE: 32

```
ggggctgatt ctggattcga caggcacagt ttgagcttga attgcgtttc gtaggttacg     60

tctacgttaa aacgttacag ttaaatataa ctgctaaaaa cgaaaacaac tcttacgctt    120

tagctgccta aaaacagtta gcgtagatcc tctcggcatc gcccatgtgc tcgagtaagg    180

gtctcaaatt tagtgggata cgtgacaact ttccgtctgt aagttgttaa agagatcatc    240

agactagcga tacagaatgc ctgtcactcg gcaagctgta aagcgaaacc acaaatgagt    300

tgactatgaa cgtagatttt taagtggcga tgtgtttgga cgcgggttca actcccgccg    360

ttccacca                                                             368
```

<210> SEQ ID NO 33
<211> LENGTH: 328
<212> TYPE: DNA
<213> ORGANISM: Thermoanaerobacterium saccharolyticum

<400> SEQUENCE: 33

```
ggggtagtag aggtaaaagt agcgagccga ggttccatct gctcgtaaaa cggtggactt     60

aaatataaac gcaaacgata atttagctta cgctgcttaa ttacaagcag ccgttcaacc    120

tttgattccc acatcaaagg attgggcgtc gatttagtgg ggaactgatt tatcaaagct    180

ttgagataaa tcggatttta tgaagctacc aaagcagtta tcctgtcact gggagaactg    240

cagagggaat gtcaaaacag tgactgcgct cggagaagct tttactgtga caccttcgga    300

ccggggttca actcccgcca gcccacca                                       328
```

<210> SEQ ID NO 34
<211> LENGTH: 379
<212> TYPE: DNA
<213> ORGANISM: Mycoplasma fermentans

<400> SEQUENCE: 34

```
ggggctgatt ctggattcga catgcattgg gtgatactaa tatcagtagt ttggcagact     60

ataatgcatc taggctttat aatcgcagaa gataaaaaag cagaagaagt taatatttct    120
```

-continued

```
tcacttatga ttgcacaaaa aatgcaatca caatcaaacc ttgctttcgc ttagttaaaa    180

gtgacaagtg gttttaaagt tgacattttc ctatatattt taaaatcggc ttttaaggag    240

aacaggagtc tgaaagggtt ccaaaaatct atattgtttg catttcggta gtatagatta    300

attagaaatg ataaactgta aaaagtattg gtattgactt ggtgtgtgga ctcgggttca    360

actcccgcca gctccacca                                                 379
```

<210> SEQ ID NO 35
<211> LENGTH: 373
<212> TYPE: DNA
<213> ORGANISM: Mycoplasma hyorhinis

<400> SEQUENCE: 35

```
ggggctgatt ctggattcga catacataaa aggatataaa ttgcagtggt cttgtaaacc     60

ataagacaat ttctttacta agcggaaaag aaaacaaaaa agaagattat tcattattaa    120

tgaatgcttc aactcaatca aatctagctt ttgcatttta aaaaactagt agaccaattt    180

gcttctcacg aattgtaatc tttatattag agaatagtta aaaatctgat cactttttaa    240

tgaatttata gatcacaggc ttttttaatc tttttgttat tttagataaa gagtcttctt    300

aaaaataact aaactgtagg aatttatatt taattatgcg tggacccggg ttcaactccc    360

gccagctcca cca                                                       373
```

<210> SEQ ID NO 36
<211> LENGTH: 399
<212> TYPE: DNA
<213> ORGANISM: Mycoplasma pirum

<400> SEQUENCE: 36

```
ggggagtcat ggttttgaca tgaatgatgg acccatagag gcagtggggt atgcccctta     60

tagctcaagg tttaaattaa ccgacaaaac tgacgaaaac gttgccgttg atacaaattt    120

attaatcaac caacaagctc aatttaacta cgcatttgca tagtataaaa aaataaattg    180

tgctactcat tgtaattagg ttactaaatt actttgtttt atatagtcct gtaactagtt    240

ctagtgatgt ctataaacta gaatgagatt tatagactta tttgttggcg gttgtgccat    300

agcctaaatc aacaaagaca atttatttat ggtactaaac tgtagattct atgatgaaat    360

tatttgtgga aacgggttcg attcccgcca tctccacca                           399
```

<210> SEQ ID NO 37
<211> LENGTH: 385
<212> TYPE: DNA
<213> ORGANISM: Mycoplasma salivarium

<400> SEQUENCE: 37

```
ggggctgatt ctggattcga caggcattcg attcattatg ttgcagtggt ttgcaaacca     60

taaggcacta ggctttttta aacgcaaaag accaaaaaac agaagatcaa gcagttgatc    120

tagcatttat gaataattca caaatgcaat caaatctagt tttcgcttag taaaattagt    180

caatttatta tggtgctcaa cataataaat ggtagtatga gcttaatatc atatgatttt    240

agttaatatg ataggatttg taactaaact atgttataga aatttgtaaa ttatatatat    300

gacataggaa atttaattta ctaaactgta gatgcataat gttgaagatg tgtggaccgg    360

ggttcaactc ccgccagctc cacca                                          385
```

<210> SEQ ID NO 38
<211> LENGTH: 362

-continued

<212> TYPE: DNA
<213> ORGANISM: Herpetosiphon aurantiacus

<400> SEQUENCE: 38
gggggcggaa aggattcgac ggggagggcc aatcgtaagt ggcaagccga gacgctgagc 60
ctcgttaaat cggcaacgcc attaactggc aaaaacactt tccgcgctcc tgtagcgctt 120
gctgcctaat taaggcaaca cgtctctact agcctcagcc cgatgggctt gtagcggcga 180
cacttagtcg ggtcgctccc ctagttatgt ctgtgggcta ggggctaaga ttaacaggct 240
ggtcgtggcc cgctttgtct atcgggtggt gcaccgataa gatttaatca atagactacg 300
cttgtagatg cttgcggttt aactttttgg acgcgggttc gattcccgcc gcctcaccac 360
ca 362

<210> SEQ ID NO 39
<211> LENGTH: 355
<212> TYPE: DNA
<213> ORGANISM: Thermomicrobium roseum

<400> SEQUENCE: 39
ggggctgatt ctggattcga cagggccgta ggtgcgagga ttgcaggtcg aggtcgccca 60
cgaactcgta aaaaggggca gccaagtaac tggcgagcgc gaactcgctc tggctgcgta 120
attcacgcag ccacgtctgc ccggaccctt ccctggtggg ttcggagcgg gcgccgcaag 180
accggggtgc ccctggccca agcgccggtg cgggccaggt caagcgtgat ccggctcggc 240
tgaccgggat cctgtcggtg ggagcctggc agcgacagta gaacaccgac taagcctgta 300
gcatatcctc ggctgaacgc tctggacgcg ggttcaactc ccgccagctc cacca 355

<210> SEQ ID NO 40
<211> LENGTH: 405
<212> TYPE: DNA
<213> ORGANISM: Chlorobium limicola

<400> SEQUENCE: 40
ggggctgatt ctggattcga caggatacgt gtgagatgtc gttgcactcc gagtttcagc 60
atggacggac tcgttaaaca agtctatgta ccattagatg cagacgatta ttcgtatgca 120
atggctgcct gattagcaca agttaactca gacgccatcg tcctgcggtg aatgcgctta 180
ctctgaagcc gccggatggc ataacccgcg cttgagccta cgggttcgcg caagtaagct 240
ccgtacattc atgcccgagg ggctgtgcgg gtaatttctc gggataaggg gacgaacgct 300
gctggcggtg taatcggccc acgaaaaccc aatcaccaga gatgagtgtg gtgactgcat 360
cgagcagtgt tttggacgcg ggttcaactc ccgccagctc cacca 405

<210> SEQ ID NO 41
<211> LENGTH: 362
<212> TYPE: DNA
<213> ORGANISM: Pirellula staleyi

<400> SEQUENCE: 41
ggggctgatt ctggattcga ccggatagcc tgaagcgaat acggcgtgcc gtggttgatc 60
agatggccac gtaaaaagct gatcacaaac ttaactgccg agagcaatct cgcacttgct 120
gcctaactaa acggtagctt ccgactgagg gctttagccg gagaggccca aaagttggtc 180
accaaatccg gaccgcctcg tgccatgatc gaaacgcacg aggtcaaaaa agtttcgatc 240
tagtgcaggg tgtagccagc agctaggcga caaactgtgc aaaaatcaaa ttttctgcta 300

-continued

```
cgcacgtaga tgtgttcgtg aaaatgtctc gggacggggg ttcaactccc gccactccac    360

ca                                                                   362


<210> SEQ ID NO 42
<211> LENGTH: 346
<212> TYPE: DNA
<213> ORGANISM: Planctomyces limnophilus
<220> FEATURE:
<221> NAME/KEY: misc_feature
<222> LOCATION: (1)..(346)
<223> OTHER INFORMATION: n is an unknown base

<400> SEQUENCE: 42

ggggctgatt ctggattcga caacctctca agaggagcgt ggccactatg ggactcgatt     60

atgttgaatt cgtcatggat cttgaagaga ccttcgacat caaactggat gacaaacatt    120

tttcagcagt caaaacacca cgcgatttgg caatcattat tcgggatcaa ttagctgctg    180

aaggcagaat ctgggatgaa tcgaatgctt ttcgcaaaat ctcgaatttg aattggacga    240

tgttgcccga gttccggatg tggactcaaa tcaaaagctc tctaccagtt tcttttcacc    300

gactgcgtcc cagcacccgt ctcgttcaac tcccgccant ccacca                   346


<210> SEQ ID NO 43
<211> LENGTH: 362
<212> TYPE: DNA
<213> ORGANISM: Planctomyces maris

<400> SEQUENCE: 43

ggggctgatt ctggattcga ctggttcacc gtatgttaag gtggcggtgc cgtggttgat     60

cagttggcca cgtaaaaagc tgatcacaat ctaattgcaa acaagcaatt ttcaatggct    120

gcttaataaa agcaaccccg gcttaggaat ctctgtctga ggagtccgac agctggtcac    180

aaaatcagac tggtatcaga tcaatgtccg ctccgtctga tacgagattc gtggtggact    240

ggtttccaac aggctctgtt tatcgtgccc gaagaaacga gactcaaacg ataaaatatg    300

caccgtagag gctttagctg agggttcaca ggacgcgggt tcaactcccg ccagctccac    360

ca                                                                   362


<210> SEQ ID NO 44
<211> LENGTH: 360
<212> TYPE: DNA
<213> ORGANISM: Alcaligenes eutrophus

<400> SEQUENCE: 44

ggggttgatt ctggattcga cgtgggttac aaagcagtgg agggcatacc gaggacccgt     60

cacctcgtta atcaatggga atgcaataac tgctaacgac gaacgttacg cactggccgc    120

ttaattgcgg ccgtcctcgc actggctcgc tgacgggcta gggtcgcaag accacgcgag    180

gtcatttacg tcagataagc tccggaaggg tcacgaagcc ggggacgaaa acctagtgac    240

tcgccgtcgt agagcgtgtt cgtccgcgat gcgccggtta aatcaaatga cagaactaag    300

tatgtagaac tctctgtgga gggcttacgg acgcgggttc aactcccgcc agctccacca    360


<210> SEQ ID NO 45
<211> LENGTH: 362
<212> TYPE: DNA
<213> ORGANISM: Alcaligenes faecalis

<400> SEQUENCE: 45

gggggcggaa aggattcgac gggggtcaag aagcagcaca gggcgtgtcg agcaccagta     60
```

-continued

```
cgctcgtaaa tccactggaa aactataaac gccaacgacg agcgtttcgc tctagccgct    120

taaggctggg ccactgcact aatttgtctt tgggttaggt agggcaacct acagcagtgt    180

tatttacaaa gaatcgaatc ggtctgcgcc acgaagtccg gttctaaaac ttagtggatc    240

gccaaggaaa ggcctgtcaa ttggcatagt ccaaggttaa aacttaaaat taattgacta    300

cacatgtaga actgtctgtg gacggcttgc ggacgggggt tcgattcccg ccgcctccac    360

ca                                                                   362
```

<210> SEQ ID NO 46
<211> LENGTH: 366
<212> TYPE: DNA
<213> ORGANISM: Chromobacterium violaceum

<400> SEQUENCE: 46

```
ggggctgatt ctggattcga cgggggttgc gaagcagatg agggcatacc gggatttcag     60

tcaccccgta aaacgctgaa tttatatagt cgcaaacgac gaaacttacg ctctggcagc    120

ctaacggccg gccagacact acaacggttc gcagatgggc cgggggcgtc aaaaccctgt    180

agtgtcactc tacatctgct agtgctgttc cgggttactt ggttcagtgc gaaataatag    240

gtaactcgcc aaagtccagc ctgtccgtcg gcgtggcaga ggttaaatcc aaatgacacg    300

actaagtatg tagaactcac tgtagaggac tttcggacgc gggttcaact cccgccagct    360

ccacca                                                               366
```

<210> SEQ ID NO 47
<211> LENGTH: 378
<212> TYPE: DNA
<213> ORGANISM: Hydrogenophaga palleroni

<400> SEQUENCE: 47

```
ggggctgatt ctggattcga cgtgggttcg gacgcgcagc agggcatgtc gaggttctgt     60

cacctcgtaa atcagcagaa aaaaaccaac tgcaaacgac gaacgtttcg cactcgccgc    120

ttaaacaccg gtgagccttg caacagcagg ccgatgggct gggcaagggg gtcgcaagac    180

ctcccggctg caaggtaatt tacatcggct ggttctgcgt cgggcacctt ggcgcaggat    240

gagattcaag gatgctggct tcccgtttag cgtgccactg cgcgactcgg gcggcgagac    300

ccaaatcaga cggctacaca tgtagaactg ctcgaaaaag gcttgcggac gggggttcaa    360

ctcccgccag ctccacca                                                  378
```

<210> SEQ ID NO 48
<211> LENGTH: 365
<212> TYPE: DNA
<213> ORGANISM: Methylobacillus glycogenes

<400> SEQUENCE: 48

```
gggggcggaa aggattcgac gggggttgca aagcagcgca gggcataccg aggcctagtc     60

acctcgtaaa taaactagaa caagtatagt cgcaaacgac gaaacttacg ctctagccgc    120

ttaatcccgg ctggacgctg caccgaaggg cctctcggtc gggtggggta acccacagca    180

gcgtcattaa gagaggatcg tgcgatattg ggttacttaa tatcgtatta aatccaaggt    240

aactcgcctg ctgtttgctt gctcgttggt gagcatcagg ttaaatcaaa caacacagct    300

aagtatgtag aactgtctgt ggagggcttg cggacggggg ttcgattccc gccgcctcac    360

cacca                                                                365
```

-continued

<210> SEQ ID NO 49
<211> LENGTH: 362
<212> TYPE: DNA
<213> ORGANISM: Nitrosomonas cryotolerans

<400> SEQUENCE: 49
ggggctgatt ctggattcga cgtgggttgc aaagcagcgc agggcatacc gaggaccaga 60
atacctcgta aatacatctg gaaaaaaata gtcgcaaacg acgaaaacta cgctttagcc 120
gcttaatacg gctagcctct gcaccgatgg gccttaacgt cgggtctggc aacagacagc 180
agagtcatta gcaaggatcg cgttctgtag ggtcacttta cagaacgtta aacaataggt 240
gactcgcctg ccatcagccc gccagctggc ggttgtcagg ttaaattaaa gagcatggct 300
aagtatgtag aactgtctgt agaggacttg cggacgcggg ttcaactccc gccagtccac 360
ca 362

<210> SEQ ID NO 50
<211> LENGTH: 378
<212> TYPE: DNA
<213> ORGANISM: Pseudomonas testosteroni

<400> SEQUENCE: 50
ggggctgatt ctggattcga cgtgggttcg ggaccggtgc ggtgcatgtc gagcttgagt 60
gacgctcgta aatctccatt caaaaaacta actgcaaacg acgaacgttt cgcactcgcc 120
gcttaatccg gtgagccttg caacagcacg ctagtgggct gggcaagggg gtagcaatac 180
ctcccggctg caagggaatt ttcattagct ggctggatac cgggcttctt ggtatttggc 240
gagattttag gaagctggct acccaagcag cgtgtgcctg cggggtttgg gtggcgagat 300
ttaaaacaga gcactaaaca tgtagatctg tccggcgaag gcttacggac gcgggttcaa 360
ctcccgccag ctccacca 378

<210> SEQ ID NO 51
<211> LENGTH: 360
<212> TYPE: DNA
<213> ORGANISM: Ralstonia pickettii

<400> SEQUENCE: 51
gggggcggaa aggattcgac gggggttgcg aagcagcgga gggcataccg aggacccgtc 60
acctcgttaa tcaatgggaa tgcaataact gctaacgacg aacgttacgc actggcagcc 120
taagggccgc cgtcctcgca ctggctcgct gacgggctag ggtcgcaaga ccagcgaggt 180
catttacgtc agataagctt taggtgagtc acgggcctag agacgaaaac ttagtgaatc 240
gccgtcgtag agcgtgttcg tccgcgatgc ggcggttaaa tcaaatgaca gaactaagta 300
tgtagaactc tctgtggagg gcttgcggac gcgggttcga ttcccgccgc ctcaccacca 360

<210> SEQ ID NO 52
<211> LENGTH: 386
<212> TYPE: DNA
<213> ORGANISM: Variovorax paradoxus

<400> SEQUENCE: 52
ggggctgatt ctggattcga cgtgggttcg gagtcgcagc ggggcatgtc gagctgaatg 60
cgctcgtaaa acagattcaa acaaactaac tgcaaacgac gaacgtttcg cactcgctgc 120
ttaattgcca gtgagccttg caacagttgg ccgatgggct gggcaagggg gtctggagca 180
atcctgacct cccggctgca aggataacta catgggctgg ctccgatccg ggtaccttgg 240

-continued gtcggggcga gaaaataggg tactggcgtc cggtttagcg tgtgactgcg cgactccgga 300
agcgagactc aaaacagatc actaaacatg tagaactgcg cgatgaaggc ttgcggacgg 360
gggttcaact cccgccagct ccacca 386

<210> SEQ ID NO 53
<211> LENGTH: 346
<212> TYPE: DNA
<213> ORGANISM: Bdellovibrio bacteriovirus

<400> SEQUENCE: 53
gggggcggaa aggattcgac gggggtgctg aagcataagg agcataccgg ggcggatgag 60
gacctcgtta aaaacgtcca ctttgtaatt ggcaacgatt acgcacttgc agcttaatta 120
agcagcacga tcaaccttgt ggtggttccg cacttggatt gatcgtcatt tagggacctc 180
ggcgtgttgg gttttctcca gcagacatgc ttaaatttac tgggggagag gtcttaggga 240
ttttgtctgt ggaagcccga ggaccaatct aaaacactga ctaagtatgt agcgccttat 300
cgtggatcat ttgcggacgg gggttcgatt cccgccgcct ccacca 346

<210> SEQ ID NO 54
<211> LENGTH: 366
<212> TYPE: DNA
<213> ORGANISM: Myxococcus xanthus

<400> SEQUENCE: 54
gggggcggaa aggattcgac gggggcattg aagttcgaga cgcgtgccga gcttgtcagg 60
tagctcgtaa attcaacccg gcaaagacac aaaagccaac gacaacgttg agctcgcgct 120
ggctgcctaa aaacagccca tagtgcgcgg tccccccgcc ctcggcctgt ggggttggga 180
cagaccgtca taatgcaggc tggctgccga gggtgcctgg acccgaggtg gcgagatctt 240
cccaggaccg gctctgagta tcccgtccgt gggagcctca gggacgtagc aaatcgcgga 300
ctacgcacgt agggtcgaag agcggacggc tttcggacgc gggttcgatt cccgccgcct 360
ccacca 366

<210> SEQ ID NO 55
<211> LENGTH: 380
<212> TYPE: DNA
<213> ORGANISM: Sulfurospirillum deleyianum

<400> SEQUENCE: 55
ggggctgatt ctggattcga caggagtagt tttagcttat ggctgcatgt cgggagtgag 60
ggtcttccgt tacacaacct tcaaacaata actgctaaca acagtaacta tcgtcctgct 120
tacgcgctag ctgcgtaagt ttaacaaata atggactgct ctcccctttg atgctatctt 180
aggaggtctt ggagagtatc atagatttga tagctatatt acatgaacgc ctttacatgt 240
aatgaagtta aaggctcgtt ttgcgtagtt ttctgattgt tgtacgaagc aaaattaaac 300
actatcaaca atatctaagc atgtagacgt cataggtggc tatttttgga ctgcgggttc 360
aactcccgcc agctccacca 380

<210> SEQ ID NO 56
<211> LENGTH: 359
<212> TYPE: DNA
<213> ORGANISM: Chromatium vinosum

<400> SEQUENCE: 56

-continued

```
ggggctgatt ctggattcga cgtgggtcgc gaaacctaag gtgcatgccg aggtgcggtt     60

gacctcgtaa aaccctccgc aaacttatag ttgccaacga cgacaactac gctctcgctg    120

cttaatccca gcgggcctct gaccgtcact tgcctgtggg cggcggattc caggggtaac    180

ctcacacagg atcgtggtga cgggagtccg gacctgatcc actaaaacct aacggaatcg    240

ccgactgatc gccctgccct tcgggcggca gaaggctaaa aacaatagag tgggctaagc    300

atgtaggacc gagggcagag ggcttgcgga cgcgggttca actcccgcca gctccacca     359


<210> SEQ ID NO 57
<211> LENGTH: 395
<212> TYPE: DNA
<213> ORGANISM: Pseudomonas fluorescens

<400> SEQUENCE: 57

ggggctgatt ctggattcga cgccggttgc gaacctttag gtgcatgccg agttggtaac     60

agaactcgta aatccactgt tgcaactttc tatagttgcc aatgacgaaa cctacgggga    120

atacgctctc gctgcgtaag cagccttagc ccttccctcc tggtaccttc gggtccagca    180

atcatcaggg gatgtctgta aacccaaagt gattgtcata tagaacagaa tcgccgtgca    240

gtacgttgtg gacgaagcgg ctaaaactta cacaactcgc ccaaagcacc ctgcccgtcg    300

ggtcgctgag ggttaactta atagacacgg ctacgcatgt agtaccgaca gcagagtact    360

ggcggacgcg ggttcaactc ccgccagctc cacca                               395


<210> SEQ ID NO 58
<211> LENGTH: 362
<212> TYPE: DNA
<213> ORGANISM: Borrelia afzelii

<400> SEQUENCE: 58

ggggctgatt ctggattcga ctgaaaatgc taatattgta agttgcaagc agagggaatc     60

tcttaaaact tctaaaataa atgcaaaaaa taataacttt acaagttcaa accttgtaat    120

ggctgcttaa gttagcagag agttttgttg aatttggctt tgagattcac ttatactctt    180

ttagacatcg aagcttgctt aaaaatgttt tcaagttgat ttttagggac ttttatactt    240

gagagcaatt tggcggtttg ctagtatttc caaaccatat tgcttagtaa aatactagat    300

aagcttgtag aagcttatag tattgttttt aggacgcggg ttcaactccc gccagtccac    360

ca                                                                   362


<210> SEQ ID NO 59
<211> LENGTH: 363
<212> TYPE: DNA
<213> ORGANISM: Borrelia crocidurae

<400> SEQUENCE: 59

ggggctgatt ctggattcga ctaagaactt tagtagcata aatggcaagc agagtgaatc     60

tcttaaaact tctttaataa atgcaaaaaa taataacttt acaagttcag atcttgtaat    120

ggctgcttaa tttagcagag agttttgttg gattttgctt tgaggttcaa cttatactct    180

ttaagacatc aaagtatgcc taaaaatgtt tcaagttgat ttttagggac ctttaaactt    240

gagagtaatt tggtggtttg cttgttttcc aagccttatt gctttttcta aaaattagct    300

aagcttgtag atatttatga tattattttt aggacgcggg ttcaactccc gccagttcca    360

cca                                                                  363
```

-continued

<210> SEQ ID NO 60
<211> LENGTH: 365
<212> TYPE: DNA
<213> ORGANISM: Borrelia hermsii

<400> SEQUENCE: 60
ggggctgatt ctggattcga ctaaaaactt tagtagcata aattgcaagc agagggaatc 60
tcttaaaact tctttaataa atgcaagaaa taataacttt acaagttcaa atcttgtaat 120
ggctgcttaa attagcagag agttctgctg gattttgctt tgaggttcag cttatactct 180
tttaagacat caaagcttgc ttaaaaatat ttcaagttga tttttaggga cttttaaatt 240
tgagagtaat ttggcggttt gctagttttt ccaaacctta ttacttaaag aaaacactag 300
ctaagcttgt agatatttat gatattattt ttaggacgcg ggttcaactc ccgccagctc 360
cacca 365

<210> SEQ ID NO 61
<211> LENGTH: 363
<212> TYPE: DNA
<213> ORGANISM: Borrelia garinii

<400> SEQUENCE: 61
ggggctgatt ctggattcga ctgaaaatgc gaatattgta agttgcaggc agagggaatc 60
tcttaaaact tctaaaataa atgcaaaaaa taataacttt acaagctcaa accttgtaat 120
ggctgcttaa gttagcaggg agtttcgttg aatttggctt tgaggttcac ttatactctt 180
ttcgatatcg aagcttgctt aaaaatgttt tcaagttaat ttttagggac ttttgtactt 240
gagagcaatt tggcggtttg ctagtatttc caaaccatat tgcttaagta aaatgctaga 300
taagcttgta gaagcttata atattgtttt taggacgcgg gttcaactcc cgccagtcca 360
cca 363

<210> SEQ ID NO 62
<211> LENGTH: 357
<212> TYPE: DNA
<213> ORGANISM: Thermodesulfobacterium commune

<400> SEQUENCE: 62
gggggcggaa aggattcgac ggggataggt aggattaaac agcaggccgt ggtcgcaccc 60
aaccacgtta aatagggtgc aaaaacacaa ctgccaacga atacgcctac gctttggcag 120
cctaagcgtg ctgccacgca cctttagacc ttgcctgtgg gtctaaaggt gtgtgaccta 180
acaggctttg ggaggcttaa tcggtggggt taagcctccc gagattacat cccacctggt 240
agggttgctt ggtgcctgtg acaagcaccc tacgagattt tcccacaggc taagcctgta 300
gcggtttaat ctgaactatc tccggacgcg ggttcgattc ccgccgcctc cccacca 357

<210> SEQ ID NO 63
<211> LENGTH: 358
<212> TYPE: DNA
<213> ORGANISM: Thermotoga neapolitana
<220> FEATURE:
<221> NAME/KEY: misc_feature
<222> LOCATION: (1)..(358)
<223> OTHER INFORMATION: n is an unknown base

<400> SEQUENCE: 63
gggggcggaa aggattcgac ggggatggag tcccctggga agcgagccga ggtccccacc 60
tcctcgtaaa aaaggtggga acacgaataa gtgccaacga acctgttgct gttgccgcct 120

-continued

```
aatagatagg cggccgtcct ctccggagtt ggctgggctc cggaagaggg cgtgagggat    180

ccagcctacc gatctgggct ccgccttccg gcccggatcg ggaaggttca ggaaggctgt    240

gggaagcgac accctgcccg tggggggtcc ttcccgagac acgaaacacg ggctgcgctc    300

ggagaagccc aggggcctcc atcttcngac gcgggttcga ttcccgccac ctccacca      358


<210> SEQ ID NO 64
<211> LENGTH: 347
<212> TYPE: DNA
<213> ORGANISM: Deinococcus proteolyticus

<400> SEQUENCE: 64

gggggcggaa aggattcgac gggggaacgg aaagcgctgc tgcgtgccga ggagccgttg     60

gcctcgtaaa caaacggcaa agccattaac tggcgaaaat aactacgctc tcgctgctta    120

agtgagacag tgaccacgta gccccgcctt tggcgacgtg tgaactgaga caaaagaagg    180

ctagcttagg tgaggttcca tagccaaaag tgaaaccaaa tggaaataag gcggacggca    240

gcctgtttgc tggcagccca ggcccgacaa tttaagagca gactacgcac gtagatgcac    300

gctggatgga cctttggacg cgggttcgat tcccgccagc tccacca                  347


<210> SEQ ID NO 65
<211> LENGTH: 352
<212> TYPE: DNA
<213> ORGANISM: Prosthecobacter fusiformis

<400> SEQUENCE: 65

ggggctgatt ctggattcga cggggagtac aaggatcaaa agctgcaagc cgaggtgccg     60

ttacctcgta aaacaacggc aaaaaagaag tgccaacaca aatttagcat tagctgctta    120

atttagcagc tacgctcttc taacccgggc tggcagggtt agaagggtgt cataatgagc    180

cagctgcccc ttccgactcc cctaaggaag ggaaagatgt aggggatagg tgcttacaga    240

atcctgcggg agggagtctg taagtgccga aaagttaaaa ctcccgctaa gcttgtagag    300

gcttttgatt cttgctctct ggacgcgggt tcaactcccg ccagctccac ca             352


<210> SEQ ID NO 66
<211> LENGTH: 329
<212> TYPE: DNA
<213> ORGANISM: Verrucomicrobium spinosum
<220> FEATURE:
<221> NAME/KEY: misc_feature
<222> LOCATION: (1)..(329)
<223> OTHER INFORMATION: n is an unknown base

<400> SEQUENCE: 66

gggnnnnatt tggaattcgc cgaatgctag aagtggaggc tgcatgccgc ggatgattcg     60

ttggccgctt taccaattcg gatcaaacaa ctaaatgcgg actctaacga gcttgccctc    120

gccgcttaat tgacggtgac gttcctccag tgaagtctgt gaattggagg agcgactact    180

tacaggctgg ccaaaagagc gggcgaccgg ccccaaggcg agatctacag gccgctggat    240

ggacggcatc ctggcagtag gaggctggac atcgagatca aatnattgcc tgagcatgga    300

gacgctttca taaaggngtt cggacaggg                                      329


<210> SEQ ID NO 67
<211> LENGTH: 318
<212> TYPE: RNA
<213> ORGANISM: Thermoanaerobacterium saccharolyticum

<400> SEQUENCE: 67
```

-continued

```
cgggggguagu agagguaaaa guagcgagcc gagguuccau cugcucguaa aacgguggac     60

uuaaauauaa acgcaaacga uaauuuagcu uacgcugcuu aauuacaagc agccguucaa    120

ccuuugauuc ccacaucaaa ggauugggcg ucgauuuagu ggggaacuga uuuaucaaag    180

cuuugagaua aaucggauuu uaugaagcua ccaaagcagu uauccuguca cugggagaac    240

ugcagaggga augucaaaac agugacugcg cucggagaag cuuuuacugu gacaccuucg    300

gaccggggguu caacuccc                                                 318
```

<210> SEQ ID NO 68
<211> LENGTH: 187
<212> TYPE: RNA
<213> ORGANISM: Clostridium acetobutylicum

<400> SEQUENCE: 68

```
aaucuggcgu cgagagcggg gaaacgagcc uuacaaagcu uugaguaagg aacggaauuu     60

augaagcuac ugaagugaaa agcuuguuug uaggcguuuc auggagggaa uguuaaaaua    120

caaacugcac ucggagaugc uuaaaugaaa ccauuuucgg acaggggguuc gauuccccuc   180

gccucca                                                              187
```

<210> SEQ ID NO 69
<211> LENGTH: 335
<212> TYPE: RNA
<213> ORGANISM: Clostridium stercorarium

<400> SEQUENCE: 69

```
cggggguuauu gaagcaagag uagcggguag aggauucucg uuggccucuu uaaaaaaacga   60

gagcuaaaaa uaaacgcaaa caacgauaac uacgcuuuag cugcugcgua aguaacacgc    120

agcccgucgg ccccggggguu ccugcgccuc gggauaccgg cgucaucaag gcagggaacc   180

agccggauca ggcuucaggu ccggugggau uuaaugaagc uaccgacuua uaaagccugu    240

cucugggcgu uauaagaagg gaaugucaaa acagagacac caaugcaccc ggagaagcuc    300

uuguggauau gguuccggac acgaguucga uuccc                               335
```

<210> SEQ ID NO 70
<211> LENGTH: 336
<212> TYPE: RNA
<213> ORGANISM: Clostridium perfringens

<400> SEQUENCE: 70

```
cgggggguaag augggguuuga uaagcgaguc gagggaagca uggugccucg auaauaaagu   60

augcauuaaa gauaaacgca gaagauaauu uugcauuagc agcuuaauuu agcgcugcuc    120

auccuuccuc aauugcccac gguugagagu aagggguguca uuuaaaagug gggaaccgag   180

ccuagcaaag cuuugagcua ggaacggaau uuaugaagcu uagaggaagu uugucugugg    240

acguucucug agggaauuuu aaaacacaag acacuaaaau cuaguacacu cguagaaagu    300

cuuacugguc ugcuuucgga cacggguuca acuccc                              336
```

<210> SEQ ID NO 71
<211> LENGTH: 305
<212> TYPE: RNA
<213> ORGANISM: Clostridium lentocellum

<400> SEQUENCE: 71

```
cggggggucac aucuacuggg gcagccaucc guagaacgcc ggagucuacg uuaaaagcug    60
```

-continued gcacuuaaag uaaacgcuga agauaauuua gcaaucgcug ccuaauuaag gcgcaguccu 120
ccuaggucuu ccgcagccua gaucagggcu ucgacucgcg gauccuucac cuggcaaagc 180
uuugagccaa cgugaacacu augaagcuag ccugucuuug ggcgcuagau ggagggaaug 240
ucaaaacaaa gaauaugaug guagagacca cgcuauaugg gcuuucggac aggggguucga 300 uuccc 305

<210> SEQ ID NO 72
<211> LENGTH: 319
<212> TYPE: RNA
<213> ORGANISM: Heliobacillus mobilis

<400> SEQUENCE: 72
cggggaacgu guuugcuugg gaugcgagcc ggguugccgc caggaccgua aaaagggcgg 60
aaggcuuuaa uugccgaaga uaacuacgcu uuagcugcuu uauugcaguc uaaccucuuc 120
uccucugugc ucucggugag gauguaaggg gucauuuaag agagcuggcu ucgaccaauu 180
cucggagguc caagcgagau uuaucgagau agccugacca acgcucuguc ugccgugcgg 240
aaggaaggcg aaaucuaaaa cgacagauac gcucguagug uccuuugugg gcauuucuuc 300
ggacgcgggu ucaacuccc 319

<210> SEQ ID NO 73
<211> LENGTH: 321
<212> TYPE: RNA
<213> ORGANISM: Heliospirillum gestii

<400> SEQUENCE: 73
cggggaacgu guuugcuuag gacgcgagcc ggguugccgc caggaccgua aaaagggcgg 60
aaggcuuuaa uugccgaaga uaacuacgcu uuagcugcuu aauugcaguc uaaccucuuc 120
uccucugugc ucucggugag gauguaaggg gucauuuaag agagcuggcu cgaaccaauu 180
cucggagguu cggguaagac uuaucgagau cagccugacc aacgcucugu cugccgugcg 240
gaaggauggc gaaaucuaaa acgacagaau acgcucguag uguccuuugu gggcauuucu 300
ucggacgcgg guucaacucc c 321

<210> SEQ ID NO 74
<211> LENGTH: 325
<212> TYPE: RNA
<213> ORGANISM: Brevibacillus brevis

<400> SEQUENCE: 74
cggggauggu agagcaugag aagcgagccg gggggguugcg gaccucguca ccaacgcaaa 60
cgccauuaac uggcaacaaa caacuuucuc ucgcugcuua auaaccagug aggcucuccc 120
acugcaucgg cccgugugcc guggauaggg cucaacuuua acgggcuacg ccggaggcuu 180
ccgccuggag ccaaaggaag aagaccaauc aggcuaggug ccaggucagc gcgucacucc 240
gcgaaucugu caccgaaacu cuaaacgagu gacugcgcuc ggagaugcuc auguaucgcu 300
guuuucggac gggggguucga uuccc 325

<210> SEQ ID NO 75
<211> LENGTH: 360
<212> TYPE: RNA
<213> ORGANISM: Bacillus subtilis

<400> SEQUENCE: 75
ggggacguua cggauucgac agggauggau cgagcuugag cugcgagccg agaggcgauc 60

-continued

```
ucguaaacac gcacuuaaau auaacuggca aaacuaacag uuuuaaccaa aacguagcau    120

uagcugccua auaagcgcag cgagcucuuc cugacauugc cuaugugucu gugaagagca    180

cauccaagua ggcuacgcuu gcguucccgu cugagaacgu aagaagagau gaacagacua    240

gcucucggaa ggcccgcccg caggcaagaa gaugagugaa accauaaaua ugcaggcuac    300

gcucguagac gcuuaaguaa ucgauguuuc uggacguggg uucgacuccc accgucucca    360
```

<210> SEQ ID NO 76
<211> LENGTH: 325
<212> TYPE: RNA
<213> ORGANISM: Bacillus badius

<400> SEQUENCE: 76

```
cagggauagu ucgagcuugg gcugcgagcc ggagggccgu cuucguacca acgcaaacgc     60

cuaaauauaa cuggcaaaaa agauuuagcu uuagcugccu aauauagguu cagcugcucc    120

ucccgcuauc guccauguag ucggguaagg gguccaaacu uaguggacua cgccggaguu    180

cuccgccugg ggacaaagga agagaucaau caggcuagcu gcccggacgc ccgucgauag    240

gcaaaaggaa cagugaaccc caaauauauc gacuacgcuc guagacguuc aaguggcguu    300

aucuuuggac gugggguucaa cuccc                                        325
```

<210> SEQ ID NO 77
<211> LENGTH: 341
<212> TYPE: RNA
<213> ORGANISM: Bacillus megaterium

<400> SEQUENCE: 77

```
ggggacguua cggauucgac aggguaguuc gagcuuaggu ugcgagucga ggagauggcc     60

ucguuaaaac aucaacgcca auaauaacug gcaaaucuaa caauaacuuc gcuuuagcug    120

cauaauagua gcuuagcguu ccucccucca ucgcccaugu gguaggguaa gggacucacu    180

uuaagugggc uacgccggag uucgccgucu gaggacgaag gaagagaaua aucagacuag    240

cgacugggac gccuguuggu aggcagaaca gcucgcgaau gaucaauaug ccaacagccg    300

uacacucgua gacgcuuaag uggccauauu ucuggacgug g                        341
```

<210> SEQ ID NO 78
<211> LENGTH: 315
<212> TYPE: RNA
<213> ORGANISM: Bacillus thermoleovorans

<400> SEQUENCE: 78

```
cgggggguagg ucgagcuuaa gcggcgagcc gagggggacg uccucguaaa aacgucaccu     60

aaagauaacu ggcaaacaaa acuacgcuuu agcugccuaa uugcugcagc uagcuccucc    120

cgccaucgcc cgcguggcgu ucgaggggcu cauauggagc gggcuacgcc caaauccgcc    180

gccugaggau gagggaagag acgaaucagg cuccgggagg ccugucggua ggcggaacgg    240

acggcgaagc gaaauauacc gacuacgcuc guagaugcuu aaguggcgau gccucuggac    300

gugggguucga uuccc                                                    315
```

<210> SEQ ID NO 79
<211> LENGTH: 335
<212> TYPE: RNA
<213> ORGANISM: Enterococcus faecium

<400> SEQUENCE: 79

-continued caggcacagu uugagcuuga auugcguuuc guagguuacg ucuacguuaa aacguuacag 60
uuaaauauaa cugcuaaaaa cgaaaacaac ucuuacgcuu uagcugccua aaaacaguua 120
gcguagaucc ucucggcauc gcccaugugc ucgaguaagg gucucaaauu uagugggaua 180
cgugacaacu uuccgucugu aaguuguuaa agagaucauc agacuagcga uacagaaugc 240
cugucacucg gcaagcugua aagcgaaacc acaaaugagu ugauaugaac guagauuuuu 300
aaguggcgau guguuuggac gcggguucaa cuccc 335

<210> SEQ ID NO 80
<211> LENGTH: 364
<212> TYPE: RNA
<213> ORGANISM: Enterococcus faecalis

<400> SEQUENCE: 80
gggggcguua cggauucgac aggcauaguu gagcuugaau ugcguuucgu agguuacggc 60
uacguuaaaa cguuacaguu aaauauaacu gcuaaaaacg aaaacaauuc uuucgcuuua 120
gcugccuaaa aaccagcuag cgaagauccu cccggcaucg cccaugugcu cgggucaggg 180
uccuaaucga agugggauac gcuaaauuuu uccgucugua aaauuuagag gagcuuacca 240
gacucagcaa uacagaaugc cugucacucg gcacgcugua aagcgaaccu uuaaaugagu 300
guuaugaacg uagagauuua aguggcaaua uguuuggacg cggguucgac ucccgccguc 360
ucca 364

<210> SEQ ID NO 81
<211> LENGTH: 346
<212> TYPE: RNA
<213> ORGANISM: Streptococcus pyogenes

<400> SEQUENCE: 81
gggguuguua cggauucgac aggcauuaug aggcauguuu ugcgucccau cggcagaugu 60
aaauugccag uuaaauauaa cugcaaaaaa uacaaacucu uacgcuuuag cugccuaaaa 120
accagcuagc gugacuucua caagauugcu uguguccugu uagaagucuc aaaauagcaa 180
gcuacgguua cgaaauuguc uaguuucgug acaagagauu gauagacucc gcaaacuaau 240
ggcuugaguu augugucuuu aguuuguuaa augaagacau aaccuaugga cguagacaaa 300
uauguuggca gguguuugga cgugggguucg acucccacca gcucca 346

<210> SEQ ID NO 82
<211> LENGTH: 344
<212> TYPE: RNA
<213> ORGANISM: Streptococcus pneumoniae

<400> SEQUENCE: 82
ggggucguua cggauucgac aggcauuaug aggcauauuu ugcgacucgu guggcgacgu 60
aaacgcucag uuaaauauaa cugcaaaaaa uaacacuucu uacgcucuag cugccuaaaa 120
accagcaggc gugacccgau uuggauugcu cguguucaau gacaggucuu auuauuagcg 180
agauacgauu aagccuuguc uagcgguuug auaagagauu gauagacucg caguuucuag 240
acuugaguua ugugucgagg ggcuguuaaa auaauacaua acuaugguug uagacaaaua 300
uguuggcagg uguuuggacg uggguucgac ucccaccggc ucca 344

<210> SEQ ID NO 83
<211> LENGTH: 364
<212> TYPE: RNA
<213> ORGANISM: Streptococcus gordonii -continued

<400> SEQUENCE: 83

```
ggggucguua cggauucgac aggcauuaug aggcauauuu ugcgacucau cuagcggaug     60

uaaaacgcca guuaaauaua acugcaaaaa auaauacuuc uuacgcuuua gcugccuaaa    120

aaccagcggg cgugacccga uucggauugc uugugucuga ugacaggucu uauuauuagc    180

aagcuacggu agaaucuugu cuagugauuu uacaagagau ugauagacua cguuagaacu    240

gagucagccg cuugauuugg gcuugaguua ugugucaaaa ucaaguuaaa acaauacaua    300

gcuaugguug uagacaaaua uguuggcaga uguuuggacg uggguucgac ucccaccggc    360

ucca                                                                 364
```

<210> SEQ ID NO 84
<211> LENGTH: 329
<212> TYPE: RNA
<213> ORGANISM: Streptococcus mutans

<400> SEQUENCE: 84

```
ggggucguua cggauucgac aggcauuaug agaccuauuu ugcgacucau cuagcggaug     60

uaaaacgcca guuaaauaua acugcaaaaa auacaaauuc uuacgcagua gcugccuaaa    120

aaccagccug ugugaucaau aacaaauugc uuguguuugu ugauuggucu uauuguuaac    180

aagcugcugu ucuaaaagag uucuacugac uccgcaucgu uagaguuuga guuauguauu    240

guaacggugu uaaauaaaca cauaaccuau aguuguagac aaauggguua gcagauguuu    300

ggacgugggu ucgacuccca ccggcucca                                      329
```

<210> SEQ ID NO 85
<211> LENGTH: 328
<212> TYPE: RNA
<213> ORGANISM: Staphylococcus epidermidis

<400> SEQUENCE: 85

```
caggggaccc cgagcuuauu aagcgugucg gaggguuggc uccgucauca acacauuucg     60

guuaaauaua acugacaaau caaacaauaa uuucgcagua gcugcguaau agccacugca    120

ucgccuaaca gcaucuccua cgugcuguua acgcgauuca acccuaguag gauaugcuaa    180

acacugccgc uugaagucug uuuagaugaa auauaaucaa gcuaguauca uguugguugu    240

uuauugcuua gcaugaugcg aaaauuauca auaaacuaca cacguagaaa gauuuguauc    300

aggaccucug gacgcggguu caacuccc                                       328
```

<210> SEQ ID NO 86
<211> LENGTH: 359
<212> TYPE: RNA
<213> ORGANISM: Staphylococcus aureus

<400> SEQUENCE: 86

```
ggggacguuc auggauucga caggggaccc ccgagcucau uaagcguguc ggaggguugu     60

cuucgucauc aacacacaca guuuauaaua acuggcaaau caaacaauaa uuucgcagua    120

gcugccuaau cgcacucugc aucgccuaac agcauuuccu augugcuguu aacgcgauuc    180

aaccuuaaua ggauaugcua aacacugccg uuugaagucu guuuagaaga aacuuaauca    240

aacuagcauc auguugguug uuuaucacuu uucaugaugc gaaaccuauc gauaaacuac    300

acacguagaa agauguguau caggaccuuu ggacgcgggu ucaaaucccg ccgucucca     359
```

<210> SEQ ID NO 87

-continued

<211> LENGTH: 334
<212> TYPE: RNA
<213> ORGANISM: Lactobacillus acidophilus

<400> SEQUENCE: 87
caggcguaga cccgcauuga cugcgguucg uagguuacgu cuacguaaaa acguuacagu 60
uaaauauaac ugcaaauaac aaaaauucuu acgcauuagc ugcuuaauuu agcgcaugcg 120
uugcucuuug ucgguuuacu cguggcugac acugaguauc aacuuagcga guuacguuua 180
acuaccucac cugaauaguu gaaaagaguc uuagcagguu agcuagucca uacuagcccu 240
guuauauggc guuuuggacu agugaaguuc aaguaauaua acuaugaucg uagaggucag 300
ugacgagaug cguuuggaca gggguucaac uccc 334

<210> SEQ ID NO 88
<211> LENGTH: 347
<212> TYPE: RNA
<213> ORGANISM: Aquifex aeolicus

<400> SEQUENCE: 88
gggggcggaa aggauucgac ggggacaggc gguccccgag gagcaggccg gguggcuccc 60
guaacagccg cuaaaacagc ucccgaagcu gaacucgcuc ucgcugccua auuaaacggc 120
agcgcguccc cgguagguuu gcggguggcc uaccggaggg cgucagagac acccgcucgg 180
gcuacucggu cgcacggggc ugaguagcug acaccuaacc cgugcuaccc ucggggagcu 240
ugcccguggg cgacccgagg ggaaauccug aacacgggcu aagccuguag agccucggau 300
guggccgccg uccucggacg cgggguucgau ucccgccgcc uccacca 347

<210> SEQ ID NO 89
<211> LENGTH: 355
<212> TYPE: RNA
<213> ORGANISM: Thermotoga maritima

<400> SEQUENCE: 89
gggggcgaac gguuucgacg gggauggagu ccccugggaa gcgagccgag guccccaccu 60
ccucguaaaa aaggugggac aaagaauaag ugccaacgaa ccuguugcug uugccgcuua 120
auagauaagc ggccguccuc uccgaaguug gcugggcuuc ggaagagggc gugagagauc 180
cagccuaccg auucaguucg ccuuccggcc ugaaucggga aaacucagga aggcuguggg 240
agaggacacc cugcccgugg gaggucccuc ccgagagcga aaacacgggc ugcgcucgga 300
gaagcccagg ggccuccauc uucggacggg gguucgaauc cccccgccuc cacca 355

<210> SEQ ID NO 90
<211> LENGTH: 355
<212> TYPE: RNA
<213> ORGANISM: Thermotoga neapolitana

<400> SEQUENCE: 90
gggggcggaa aggauucgac ggggauggag uccccuggga agcgagccga gguccccacc 60
uccucguaaa aaaggugggga acacgaauaa gugccaacga accuguugcu guugccgccu 120
aauagauagg cggccguccu cuccggaguu ggcugggcuc cggaagaggg cgugagggau 180
ccagccuacc gaucugggcu ccgccuuccg gcccggaucg ggaagguuca ggaaggcugu 240
gggaagcgac acccugcccg ugggggguccc uucccgagac acgaaacacg ggcugcgcuc 300
ggagaagccc aggggccucc aucuucggac gggggguucga uucccgccgc cucca 355

-continued

<210> SEQ ID NO 91
<211> LENGTH: 350
<212> TYPE: RNA
<213> ORGANISM: Thermus thermophilus

<400> SEQUENCE: 91
gggggugaaa cggucucgac gggggucgcc gagggcgugg cugcgcgccg aggugcgggu 60
ggccucguaa aaacccgcaa cggcauaacu gccaacacca acuacgcucu cgcggcuuaa 120
ugaccgcgac cucgcccggu agcccugccg ggggcucacc ggaagcgggg acacaaaccc 180
ggcuagcccg gggccacgcc cucuaacccc gggcgaagcu ugaaggggc ucgcuccugg 240 ccgcccgucc gcgggccaag ccaggaggac acgcgaaacg cggacuacgc gcguagaggc 300
cacgccccgg cgaccuucgg acgggggguuc gauuccccc accuccacca 350

<210> SEQ ID NO 92
<211> LENGTH: 349
<212> TYPE: RNA
<213> ORGANISM: Deinococcus radiodurans

<400> SEQUENCE: 92
gggggugacc cgguuucgac aggggaacug aaggugaugu ugcgugucga ggugccguug 60
gccucguaaa caaacggcaa agccauuuaa cuggcaacca gaacuacgcu cucgcugcuu 120
aagugagaug acgaccgugc agcccggccu uuggcgucgc ggaagucacu aaaaaagaag 180
gcuagcccag gcgauucucc auagccgacg gcgaaacuuu auggagcuac ggccugcgag 240
aaccugccca cuggugagcg ccggcccgac aaucaaacag ugggauacac acguagacgc 300
acgcuggacg gaccuuugga cggcgguucg acuccgccca ccuccacca 349

<210> SEQ ID NO 93
<211> LENGTH: 347
<212> TYPE: RNA
<213> ORGANISM: Deinococcus proteolyticus

<400> SEQUENCE: 93
gggggcggaa aggauucgac gggggaacgg aaagcgcugc ugcgugccga ggagccguug 60
gccucguaaa caaacggcaa agccauuaac uggcgaaaau aacuacgcuc ucgcugcuua 120
agugagagca gugaccacgu agccccgccu uuggcgacgu gugaacugag acaaaagaag 180
gcuagcuuag gugagguucc auagccaaaa gugaaaccaa auggaaauaa ggcggacggc 240
agccuguuug cuggcagccc aggcccgaca auuuaagagc agacuacgca cguagaugca 300
cgcuggaugg accuuuggac ggcgguucga uucccgccgc cucacca 347

<210> SEQ ID NO 94
<211> LENGTH: 334
<212> TYPE: RNA
<213> ORGANISM: Thermomicrobium roseum

<400> SEQUENCE: 94
cagggccgua ggugcgagga uugcaggucg aggucgccca cgaacucgua aaaaggggca 60
ccaaguaacu ggcgagcgcg aacucgcucu ggcugcguaa uucacgcagc cacgucugcc 120
cggacccuuc ccuggugggu ucggagcggg cgccgcaaga ccggggugcc ccuggcccaa 180
gcgccggugc gggccagguc aagcgugauc cggcucggcu gaccgggauc cugucggugg 240
gagccuggca gcgacaguag aacaccgacu aagccuguag cauauccucg gcugaacgcu 300
cuggacgggg guucaacucc cgccagcucc acca 334

-continued

<210> SEQ ID NO 95
<211> LENGTH: 353
<212> TYPE: RNA
<213> ORGANISM: Coprothermobacter proteolyticus

<400> SEQUENCE: 95
gggggcggaa aggauucgac ggggagucgg agccuugagc ugcaggcagg guuggcugcc 60
acaccuuaaa aagggguagca aggcaaaaau aaaugccgaa ccagaauuug cacuagcugc 120
uuaauguaag cagccgcucu ccaaacugag gcugcauaag uuuggaagag cgucaaccca 180
ugcagcggcu cuuaagcagu ggcaccagcu guuuaagggu gaaaagagug gugcugggca 240
gugcgguugg gcuuccuggg cugcacuguc gagacuucac aggagggcua agccuguaga 300
cgcgaaaggu ggcggcucgu cggacgcggg uucgauuccc gccgccucca cca 353

<210> SEQ ID NO 96
<211> LENGTH: 360
<212> TYPE: RNA
<213> ORGANISM: Herpetosiphon aurantiacus

<400> SEQUENCE: 96
gggggcggaa aggauucgac ggggagggcc aaucguaagu ggcaagccga gacgcugagc 60
cucguuaaau cggcaacgcc auuaacuggc aaaaacacuu uccgcgcucc uguagcgcuu 120
gcugccuaau uaaggcaaca cgucucuacu agccucagcc cgaugggcuu guagcggcga 180
cacuuagucg ggucgcuccc cuaguuaugu cugugggcua ggggcuaaga uuaacaggcu 240
ggucguggcc cgcuuugucu aucgggugu gcaccgauaa gauuuaauca auagacuacg 300
cuuguagaug cuugcgguuu aacuuuuugg acgcggguuc gauucccgcc gccuccacca 360

<210> SEQ ID NO 97
<211> LENGTH: 355
<212> TYPE: RNA
<213> ORGANISM: Thermodesulfobacterium commune

<400> SEQUENCE: 97
gggggcggaa aggauucgac ggggauaggu aggauuaaac agcaggccgu ggucgcaccc 60
aaccacguua aauagggugc aaaaacacaa cugccaacga auacgccuac gcuuuggcag 120
ccuaagcgug cugccacgca ccuuuagacc uugccugugg gucuaaaggu gugugaccua 180
acaggcuuug ggaggcuuaa ucggugggu uaagccuccc gagauuacau cccaccuggu 240
aggguugcuu ggugccugug acaagcaccc uacgagauuu ucccacaggc uaagccugua 300
gcgguuuaau cugaacuauc uccggacgcg gguucgauuc ccgccgccuc cacca 355

<210> SEQ ID NO 98
<211> LENGTH: 329
<212> TYPE: RNA
<213> ORGANISM: Verrucomicrobium spinosum
<220> FEATURE:
<221> NAME/KEY: misc_feature
<222> LOCATION: (1)..(329)
<223> OTHER INFORMATION: n is an unknown base

<400> SEQUENCE: 98
gggnnnnauu uggaauucgc cgaaugcuag aaguggaggc ugcaugccgc ggaugauucg 60
uuggccgcuu uaccaauucg gaucaaacaa cuaaaugcgg acucuaacga gcuugcccuc 120
gccgcuuaau ugacggugac guuccuccag ugaagucugu gaauuggagg agcgacuacu 180
uacaggcugg ccaaaagagc gggcgaccgg ccccaaggcg agaucuacag gccgcuggau 240
ggacggcauc cuggcaguag gaggcuggac aucgagauca aaunauugcc ugagcaugga 300
gacgcuuuca uaaaggnguu cggacaggg 329

<210> SEQ ID NO 99
<211> LENGTH: 351
<212> TYPE: RNA
<213> ORGANISM: Dictyoglomus thermophilum

<400> SEQUENCE: 99
gggggcggaa aggauucgac ggggaguaca aggaucaaaa gcugcaagcc gaggugccgu 60
uaccucguaa aacaacggca aaaaagaagu gccaacacaa auuuagcauu agcugcuuaa 120
uuuagcagcu acgcucuucu aacccgggcu ggcaggguua gaagggugug auaaugagcc 180
agcugccccu uccgacuccc cuaaggaagg gaaagaugua ggggauaggu gcuuacagaa 240
uccugcggga gggagucugu aagugccgaa aaguuaaaac ucccgcuaag cuuguagagg 300
cuuuugauuc uugcucucug gacgcggguu cgauucccgc cgccuccacc a 351

<210> SEQ ID NO 100
<211> LENGTH: 399
<212> TYPE: RNA
<213> ORGANISM: Synechocystis sp. PCC 6803

<400> SEQUENCE: 100
ggggccgcaa ugguuucgac agguuggcga aagcuugccc gugauacagg ucgagaguga 60
gucuccucuc gcaaaucaaa ggcucaaaaa aaaguaacug cgaauaacau cgucagcuuc 120
aaacggguag ccauagcagc cuagucugua aaagcuacau uuucuuguca aagaccguuu 180
acuucuuuuc ugacuccguu aaggauuaga gguuaacccc aacggaugcu uuguuuggcu 240
cuucucuagu uagcuaaaca aucaagacuc agacuagagc aucccaccau cagggauaau 300
cgaugguccc cguccuaggg cuagaaggac uaaaccugug aaugagcgga aaguuaauac 360
ccaguuugga cagcaguuca auucugcucg gcuccacca 399

<210> SEQ ID NO 101
<211> LENGTH: 385
<212> TYPE: RNA
<213> ORGANISM: Nostoc muscorum

<400> SEQUENCE: 101
ggguccgucg guuucgacag guuggcgaac gcuacucugu gauucagguc gagagugagu 60
cuccucugca aaucaaggcu caaaacaaaa guaaaugcga auaacaucgu uaaaauuugcu 120 cguaaggacg cucuaguagc ugccuaaaua gccucuuuca gguucgagcg ucuucgguuu 180
gacuccguua aggacugaag accaaccccc aacggaugcu cuagcaaugu ucucugguug 240
gcuugcuagc uaagauuuaa ucagagcauc cuacguucgg gauaaugaac gauucccgcc 300
uugaggguca gaaaggcuaa accugugaau gagcgggggg ucaauaccca auuuggacag 360
caguucgacu cugcucgauc cacca 385

<210> SEQ ID NO 102
<211> LENGTH: 393
<212> TYPE: RNA
<213> ORGANISM: Synechococcus PCC 6301

<400> SEQUENCE: 102
ggggcuguaa ugguuucgac guguugguga auccuucacc gugauucagg ccgagaggga 60

-continued

```
guccacucuc guaaauccag gcucaaccaa aaguaacugc gaacaacauc guuccuuucg    120

cucguaaggc ugcuccugua gcugcuuaaa cgccacaaac uuucuggcuc gagcgucuag    180

ucguagacuc cguuaaauacg ccuagacuua aacccccaac ggaugcugag uggcggccuc   240

agguccgucc ucucgcuaag caaaaaccug agcaucccgc caacggggau aaucguuggc    300

ucccgcacag ugggucaacc gugcuaagcc ugugaacgag cggaaaguua cuagucaaug    360

cggacagcgg uucgauuccg cucagcucca cca                                 393
```

<210> SEQ ID NO 103
<211> LENGTH: 312
<212> TYPE: RNA
<213> ORGANISM: Leptolyngbya sp. (ATCC 27894)

<400> SEQUENCE: 103

```
ggcucaaaaa aauagaugca aacaacaucg uaccuuucgc ucguaaaacu gcaccuguug     60

cagcauaaaa caccucuaau ucagguucga gcgcuuaccg ucugacaccg uuaaagauag    120

uaagcacaac cccaacgguu gcucuagaau uucgccuuug gucggcauuc uagcuaagac    180

aauaccaaag cauccuauug uccgggacaa aggacaguuc ccgcuucgag gauuagagaa    240

gcuaaaccug ugaaugauug auagagcuaa uacccaguuu ggacacgggu ucaacucccg    300

ccagcuccac ca                                                        312
```

<210> SEQ ID NO 104
<211> LENGTH: 323
<212> TYPE: RNA
<213> ORGANISM: Porphyra purpurea

<400> SEQUENCE: 104

```
ggggcugcaa gguuucuaca uugugaaaaa acaaauauau gaaaguaaaa cgagcucauu     60

auuagagcuu uuaguuaaau aaaugcagaa aauaauauua uugcuuuuuc ucgaaaauua    120

gcuguugcau aaauagucuc aauuuuugua auucgaagug auagacucuu auacacuacg    180

aauauucugu uagaguugcu cuuaauaaaa gaaaaguaaa aaaauacaaa uucuuauguu    240

uuuuaccuga auugauucaa uuuaagguua guauuuuuug auuuuuacaa uggacguggg    300

uucaaguccc accagcucca cca                                            323
```

<210> SEQ ID NO 105
<211> LENGTH: 294
<212> TYPE: RNA
<213> ORGANISM: Cyanophora paradoxa

<400> SEQUENCE: 105

```
ggggcuguuu agguuucgac guuuuuuucu aauuauguuu guuaagcaag ucgaggauuu     60

guucuaucuc gaaaaucaag aacucucaaa auuuaaacgc aacuaauauu guacguuuua    120

accguaaagc agcuuucgcu guuuaauaau uacuuuuaau uuaaaaaccu aauuuuuuua    180

ggaauuuauu uauuuauugu uuauccugcu uaaugaauua aaaaaagcua uacuugugaa    240

uaaacgcaua auuuaaaaaa acggacgugg guucaaaucc caccagcucc acca          294
```

<210> SEQ ID NO 106
<211> LENGTH: 371
<212> TYPE: RNA
<213> ORGANISM: Odontella sinensis

<400> SEQUENCE: 106

```
ggggcugacu ugguuucgac auuuaaaaau uguuacagua ugaugcaggu cgaaguuucu     60
```

-continued

```
aaucuucgua aaaaaagaga aauuuauaau aaaugcuaau aauuuaauuu cuucuguguu    120

uaaaaguuua ucaacuaagc aaaauaguuu aaauuuaagu uuugcuguuu aaguuuuaug    180

cacauuuaau gaucuaguaa auaacuuugu ucgcuauaau uuauauuuau aacuagacuu    240

uugucuuuuu uauaguuuag aauaacuuua ucauuucaaa ccucguucca ucuaguugaa    300

cuaaaccugu gaacgaauac uauaauaaaa uuuuuagaug gacgugggau cgacucccau    360

cagcuccacc a                                                         371
```

<210> SEQ ID NO 107
<211> LENGTH: 348
<212> TYPE: RNA
<213> ORGANISM: Thalassiorsira weissflogii

<400> SEQUENCE: 107

```
ggggcugauu ugguuucgac auuuaaaacu ucuuucuaug ugucagguca aaguuuguau     60

ucuuuguaaa aaaauacuaa aauacuaaua aaugcuaaua auauaauacc guuuauuuuu    120

aaagcaguaa aaacaaaaaa agaagcaaug gcuuuaaauu uugcuguaua guucauuaac    180

uuagguuauu aaauauuuuu ucauuauaac uggacuuuuu cucaguuuau aguuuagaau    240

aaauuuaaau uuugcaaaac ucguucgaaa auuuucgggc uaaaccugua aacgcaaaua    300

cuaagaaauu uuagauggac augguucaa uucccaucag uuccacca                 348
```

<210> SEQ ID NO 108
<211> LENGTH: 330
<212> TYPE: RNA
<213> ORGANISM: Guillardia theta

<400> SEQUENCE: 108

```
ggggcugauu uggauucgac auauaaauuu gcguguuuca uuaugaagca agucaaguuu     60

aaugaucuug uaaaaaacau uaaaguacaa auaaaugcaa gcaauauagu uucauuuagu    120

ucaaaacguu uagucucuuu ugcauaagca aaaugugua auaacuuucu uaguagaaau    180

uggagaaguu uacuaagauu uauauuuacu ccauaauuau uuuaaagaug guaaaaaggu    240

gauucaucau uuguauguuu cuaaacuuug ugaaagaaua gugggcucca uuuauaauga    300

acgugggguuc aaaucccacc agcuccacca                                    330
```

<210> SEQ ID NO 109
<211> LENGTH: 353
<212> TYPE: RNA
<213> ORGANISM: Mycoplasma hyorhinis

<400> SEQUENCE: 109

```
cauacauaaa aggauauaaa uugcaguggu cuuguaaacc auaagacaau uucuuuacua     60

agcggaaaag aaaacaaaaa agaagauuau ucauuauuaa ugaaugcuuc aacucaauca    120

aaucuagcuu uugcauuuua aaaaacuagu agaccaauuu gcuucucacg aauuguaauc    180

uuuauauuag agaauaguua aaaaucugau cacuuuuuaa ugaauuuaua gaucacaggc    240

uuuuuuaauc uuuuuguuau uuuagauaaa gagucuucuu aaaaauaacu aaacuguagg    300

aauuuauauu uaauuaugcg uggacccggg uucaacuccc gccagcucca cca           353
```

<210> SEQ ID NO 110
<211> LENGTH: 411
<212> TYPE: RNA
<213> ORGANISM: Mycoplasma capricolum -continued

<400> SEQUENCE: 110
ggggauguca uggauuugac aggauaucuu uaguacauau aagcaguagu guuguagacu 60
auaaauacua cuagguuuaa aaaaacgcaa auaaaaaacga agaaacuuuu gaaaugccag 120
cauuuaugau gaauaaugca ucagcuggag caaacuuuau guuugcuuaa uaacuacuag 180
uuuaguuaua guauuucacg aauuauagau auuuuaagcu uuauuuauaa ccguauuacc 240
caagcuuaau agaauauaug auugcaauaa auauauuuga aaucuaauug caaaugauau 300
uuaaccuuua guuaauuuua guuaaauauu uuaauuagaa aauuaacuaa acuguagaaa 360
guauguauua auauaucuug gacgcgaguu cgauucucgc caucuccacc a 411

<210> SEQ ID NO 111
<211> LENGTH: 381
<212> TYPE: RNA
<213> ORGANISM: Mycoplasma pirum

<400> SEQUENCE: 111
caugaaugau ggacccauag aggcaguggg guaugccccu uauagcucaa gguuuaaauu 60
aaccgacaaa acugacgaaa acguugccgu ugauacaaau uuauuaauca accaacaagc 120
ucaauuuaac uacgcauuug cauaguauaa aaaaauaaau ugugcuacuc auuguaauua 180
gguuacuaaa uuacuuuguu uuauauaguc cuguaacuag uucuagugau gucuauaaac 240
uagaaugaga uuuauagacu uauuuguugg cgguugugcc auagccuaaa ucaacaaaga 300
caauuuauuu augguacuaa acuguagauu cuaugaugaa auuauuugug gaaacggguu 360
cgauucccgc caucuccacc a 381

<210> SEQ ID NO 112
<211> LENGTH: 387
<212> TYPE: RNA
<213> ORGANISM: Mycoplasma pneumoniae

<400> SEQUENCE: 112
ggggauguag agguuuugac auaauguuga aaggaaaaca guugcagugg gguaugcccc 60
uuacagcucu agguauaaua accgacaaaa auaacgacga aguuuuggua gauccaaugu 120
ugaucgcuaa ccaacaagca aguaucaacu acgcuuucgc uuagaacaua cuaaagcuac 180
acgaauugaa ucgccauagu uugguucgug ucacaguuua uggcucgggg uuaacugguu 240
caacuuaauc cuuaaauuau gaacuuaucg uuuacuuguu ugucuuauga ucuaaaguaa 300
gcgagacauu aaaacauaag acuaaacugu agaagcuguu uuaccaaucc uuuauggaaa 360
cggguucgau ucccgucauc uccacca 387

<210> SEQ ID NO 113
<211> LENGTH: 388
<212> TYPE: RNA
<213> ORGANISM: Mycoplasma genitalium

<400> SEQUENCE: 113
ggggauguuu uggguuugac auaaugcuga uagacaaaca guagcauugg gguaugcccc 60
uuacagcgcu agguucaaua accgacaaag aaaauaacga aguguuggua gauccaaauu 120
ugaucauuaa ccaacaagca aguguuaacu uugcuuuugc auaaguagau acuaaagcua 180
cagcugguga auagucauag uuugcuagcu gucauaguuu augacucgag guuaaaucgu 240
ucaauuuaac cuuuaaaaau agaacuuguu guuuccauga uuguuuugug aucaauugga 300
aacaagacaa aaauccacaa aacuaaaaug uagaagcugu uuguuguguc cuuuauggaa 360

-continued acggguucga uucccgucau cuccacca 388

<210> SEQ ID NO 114
<211> LENGTH: 412
<212> TYPE: RNA
<213> ORGANISM: Ureaplasma urealyticum

<400> SEQUENCE: 114
ggggauguca cgguuucgac gugacacauu aauuuuuaau ugcagugggg uuagccccuu 60
aucgcuuucg aggcauuuua aaugcagaaa auaaaaaauc uucugaagua gaauuaaacc 120
cagcguuuau ggcuucagcu acuaaugcaa acuacgcuuu ugcguacuaa uuaguuauua 180
guagaaacgu ucauuaacau aauuacuauu gguugguuuu ugggcuuauu uuacaauagu 240
uuuaaauuua aaauucuuau uguuguuuaa auuuaaauag auuuaacaaa uaguuaguua 300
auuuuaaauu uguuuuauua guuauuaacu acacuauuuu uaauaaaacu aaacuguaga 360
uauuauuaau uauguguugc ggaaaggggu ucgauucccc ucaucuccac ca 412

<210> SEQ ID NO 115
<211> LENGTH: 365
<212> TYPE: RNA
<213> ORGANISM: Mycoplasma salivarium

<400> SEQUENCE: 115
caggcauucg auucauuaug uugcaguggu uugcaaacca uaaggcacua ggcuuuuuua 60
aacgcaaaag accaaaaaac agaagaucaa gcaguugauc uagcauuuau gaauaauuca 120
caaaugcaau caaaucuagu uuucgcuuag uaaaauuagu caauuuauua uggugcucaa 180
cauaauaaau gguaguauga gcuuaauauc auaugauuuu aguuaauaug auaggauuug 240
uaacuaaacu auguuauaga aauuuguaaa uuauauauau gacauaggaa auuuaauuua 300
cuaaacugua gaugcauaau guugaagaug uguggaccgg gguucaacuc ccgccagcuc 360
cacca 365

<210> SEQ ID NO 116
<211> LENGTH: 363
<212> TYPE: RNA
<213> ORGANISM: Clostridium innocuum

<400> SEQUENCE: 116
cggggauaug ucugguacag acugcagucg agugguuacg uaauaaccaa uuaaauuuaa 60
acggaaaaac uaaauuagcu aaccucuuug guggaaacca gagaauggcu uucgcugcuu 120
aauaaccgau auagguucgc agccgccucu gcaugcuucu uccuugacca uguggaugug 180
cgcguaagac gcaagggaua aggaaucugg uuugccugag aucagauuca cgaaaauucu 240
ucaggcacau ucaucagcgg auguucauga ccugcugaug ucuuaaucuu cauggacuaa 300
acuguagagg ucuguacgug gggcuguuuc uggacaggag uucgauuccc gccgccucca 360
cca 363

<210> SEQ ID NO 117
<211> LENGTH: 359
<212> TYPE: RNA
<213> ORGANISM: Mycoplasma fermentans

<400> SEQUENCE: 117
caugcauugg gugauacuaa uaucaguagu uuggcagacu auaaugcauc uaggcuuuau 60

-continued

```
aaucgcagaa gauaaaaaag cagaagaagu uaauauuucu ucacuuauga uugcacaaaa    120

aaugcaauca caaucaaacc uugcuuucgc uuaguuaaaa gugacaagug guuuuaaagu    180

ugacauuuuc cuauauauuu uaaaaucggc uuuuaaggag aacaggaguc ugaaaggguu    240

ccaaaaaucu auauuguuug cauuucggua guauagauua auuagaaaug auaaacugua    300

aaaaguauug guauugacuu ggugugugga cucggguuca acucccgcca gcuccacca     359


<210> SEQ ID NO 118
<211> LENGTH: 320
<212> TYPE: RNA
<213> ORGANISM: Acidobacterium capsulatum

<400> SEQUENCE: 118

cggggauugac ugcggcaaag aggcaugccg gggggugggc acccguaauc gcucgcaaaa    60

caauacuugc caacaacaau cuggcacucg cagcuuaauu aaauaaguug ccguccucug    120

aggcuucgcc ugugggccga ggcaggacgu cauacagcag gcugguuccu ucggcugggu    180

cugggccgcg gggaugagau ccacggacua gcauucugcg uaucuugucg cuucuaagcg    240

cagagugcga aaccuaaagg aaugcgacug agcauggagu cucuuuucug acaccaauuu    300

cggacgcggg uucgauuccc                                                320


<210> SEQ ID NO 119
<211> LENGTH: 319
<212> TYPE: RNA
<213> ORGANISM: Fusobacterium mortiferum

<400> SEQUENCE: 119

cggggguuaug agguuauagg uagcaugcca ggaugaccgc ugugagaggu caacacaucg    60

uuuagaugga aacagaaauu acgcuuuagc ugcuuaauua gucagcucac cucugguuuc    120

ucucuucugu aggagaaucc aaccgaggug uuaccaauau acagauuacc uuuagugauu    180

ucucuaagcu caaagggaca uuuuagagaa uagcuucagu uagcccuguc ugcgggagug    240

auuguugcga aauaaaauag uagacuaagc auuguagaag ccuauggcgc ugguaguuuc    300

ggacacgggu ucaacuccc                                                 319


<210> SEQ ID NO 120
<211> LENGTH: 329
<212> TYPE: RNA
<213> ORGANISM: Fibrobacter succinogenes

<400> SEQUENCE: 120

cagggguuacc gaaguguuag uugcaagucg aggucucaga cgagggcuac ucguuaaaaa    60

gucugaaaaa aaauaagugc ugacgaaaac uacgcacucg cugccuaauu aacggcaacg    120

ccgggccuca uuccgcuccc aucggggugu acguccggac gcaauauggg auagggaagu    180

gucaugccug ggggcaucuc ccgagauuuu cuaggcuggu caaacuccgc gccgaccuuc    240

uugggcgugg auaagacgag aucuuaaauu cgaagggaac acuuguagga acguacaugg    300

acgugauuuu ggacaggggu ucaacuccc                                      329


<210> SEQ ID NO 121
<211> LENGTH: 300
<212> TYPE: RNA
<213> ORGANISM: Artificial
<220> FEATURE:
<223> OTHER INFORMATION: isolated from rumenal fluid

<400> SEQUENCE: 121
```

-continued acgcccuugu cucagacgag ggcacucguu aaaaagucug aaaagaauaa cugcagaacc 60
uguagcuaug gcugcuuaau uuaagggcaa cccuuggauc cgccuccauc ccgaaggggu 120
ggcauccgag ucgcaaaucg ggauaggaug gaucuuggca acgaggagua cauccgaaau 180
uugucgcugc uggcugaagc aucgccguuc cucuuugggc guggcaaggc aagauuaaau 240
ucagaggaua agcguguagu agcgagugag uagguguuuu uggacgcggg uucaaguccc 300

<210> SEQ ID NO 122
<211> LENGTH: 330
<212> TYPE: RNA
<213> ORGANISM: Pirellula staleyi

<400> SEQUENCE: 122
ccggauagcc ugaagcgaau acggcgugcc gugguugauc agauggccac guaaaaagcu 60
gaucacaaac uuaacugccg agagcaaucu cgcacuugcu gccuaacuaa acgguagcuu 120
ccgacugagg gcuuuagccg gagaggccca aaaguugguc accaaauccg gaccgccucg 180
ugccaugauc gaaacgcacg aggucaaaaa aguuucgauc uagugcaggg uguagccagc 240
agcuaggcga caaacugugc aaaaaucaaa uuuucugcua cgcacguaga uguguucgug 300
aaaaugucuc gggacggggg uucaacuccc 330

<210> SEQ ID NO 123
<211> LENGTH: 329
<212> TYPE: RNA
<213> ORGANISM: Planctomyces maris

<400> SEQUENCE: 123
cugguucacc guauguuaag guggcggugc cgugguugau caguuggcca cguaaaaagc 60
ugaucacaau cuaauugcaa acaagcaauu uucaauggcu gcuuaauaaa agcaaccccg 120
gcuuaggaau cucugucuga ggaguccgac agcuggucac aaaaucagac ugguaucaga 180
ucaauguccg cuccgucuga uacgagauuc gugguggacu gguuuccaac aggcucuguu 240
uaucgugccc gaagaaacga gacucaaacg auaaaauaug caccguagag gcuuuagcug 300
aggguucaca ggacgcgggu ucaacuccc 329

<210> SEQ ID NO 124
<211> LENGTH: 318
<212> TYPE: RNA
<213> ORGANISM: Artificial
<220> FEATURE:
<223> OTHER INFORMATION: isolated from sludge

<400> SEQUENCE: 124
cagggaacca ggaggugaga gaugcaugcc ggagacgcug uccgcuccgu uaucaagcag 60
cacaacaaaa uaauugcaaa caacaauuac uccuuagcag cguaagcagc uaacguucaa 120
ccucuccgga ccgccgggag gggauuuggg cgucgaaaca gcgcggacgc uccggauagg 180
acgcccauaa uauccggcua agaccauggg ucuggcucuc gcgggucuga uugucuucca 240
ccgcgcgggc cgcgaucaaa gacaacuaag cauguagguu cuugcauggc cuguucuuug 300
gacgcggguu cgauuccc 318

<210> SEQ ID NO 125
<211> LENGTH: 407
<212> TYPE: RNA
<213> ORGANISM: Porphyromonas gingivalis -continued

<400> SEQUENCE: 125

```
ggggcugacc ggcuuugaca gcgugaugaa gcgguaugua agcauguagu gcgugggugg     60
cuugcacuau aaucucagac aucaaaaguu uaauuggcga aaauaacuac gcucucgcug    120
cguaaucgaa gaauaguaga uuagacgcuu caucgccgcc aaaguggcag cgacgagaca    180
ucgcccgagc agcuuuuucc cgaaguagcu cgauggugcg gugcugacaa aucgggaacc    240
gcuacaggau gcuuccugcc uguggucaga ucgaacggaa gauaaggauc gugcauuggg    300
ucguuucagc cuccgcucgc ucacgaaaau uccaacugaa acuaaacaug uagaaagcau    360
auugauucca uguuuggacg aggguucaau ucccuccagc uccacca                  407
```

<210> SEQ ID NO 126
<211> LENGTH: 379
<212> TYPE: RNA
<213> ORGANISM: Bacteroides thetaiotaomicron

<400> SEQUENCE: 126

```
cagcgggcag aaaugguagg uaagcaugca gugggucggu aauuuccacu uaaaucucag     60
uuaucaaaac uuuaucuggc gaaacuaauu acgcucuugc ugcuuaaucg aaucacagua    120
gauuagcuua auccaggcac uaggugccca ggagagacau cacucggaag cuguugcucc    180
gaagcauucc gguucagugg ugcaguaaca ucggggauag ucagaagcgg ccucgcguuu    240
uugaugaaac uuuagaggau aaggcaggaa uugauggcuu ugguucugcu ccugcacgaa    300
aauuuaggca aagauaagca uguagaaagc uuaugauuuc cucguuugga cgaggguuca    360
acucccgcca gcuccacca                                                 379
```

<210> SEQ ID NO 127
<211> LENGTH: 404
<212> TYPE: RNA
<213> ORGANISM: Chlorobium tepidum

<400> SEQUENCE: 127

```
ggggaugaca ggcuaucgac aggauaggug ugagaugucg uugcacuccg aguuucagca     60
uggacggacu cguuaaacaa gucuauguac caauagaugc agacgauuau ucguaugcaa    120
uggcugccug auuagcacaa guuaauucag aagccaucgu ccugcgguga augcgcuuac    180
ucugaagccg ccggauggca uaacccgcgc uugagccuac ggguucgcgc aaguaagcuc    240
cguacauuca ugcccgaggg ggugugcggg uaaccaaucg ggauaagggg acgaacgcug    300
cuggcggugu aaucggacca cgaaaaacca accaccagag augagugugg uaacugcauc    360
gagcaguguc cuggacgcgg guucaagucc cgccaucucc acca                     404
```

<210> SEQ ID NO 128
<211> LENGTH: 372
<212> TYPE: RNA
<213> ORGANISM: Chlorobium limicola

<400> SEQUENCE: 128

```
caggauacgu gugagauguc guugcacucc gaguuucagc auggacggac ucguuaaaca     60
agucuaugua ccauuagaug cagacgauua uucguaugca auggcugccu gauuagcaca    120
aguuaacuca gacgccaucg uccugcggug aaugcgcuua cucugaagcc gccggauggc    180
auaacccgcg cuugagccua cggguucgcg caaguaagcu ccguacauuc augcccgagg    240
ggcugugcgg guaauuucuc gggauaaggg gacgaacgcu gcuggcggug uaaucggccc    300
acgaaaaccc aaucaccaga gaugagugug gugacugcau cgagcagugu uuuggacgcg    360
```

-continued

```
gguucaacuc cc                                                      372

<210> SEQ ID NO 129
<211> LENGTH: 420
<212> TYPE: RNA
<213> ORGANISM: Chlamydia trachomatis

<400> SEQUENCE: 129

gggggguguaa agguuucgac uuagaaauga agcguuaauu gcaugcggag ggcguuggcu    60

ggccuccuaa aaagccgaca aaacaauaaa ugccgaaccu aaggcugaau gcgaaauuau   120

cagcuucgcu gaucucgaag aucuaagagu agcugcuuaa uuagcaaagu uguuaccuaa   180

auacggguga cccgguguuc gcgagcucca ccagagguuu ucgaaacacc gucauguauc   240

ugguuagaac uuagguccuu uaauucucga ggaaaugagu uugaaauuua augagagucg   300

uuagucucua uaggggguuuc uagcugagga gacauaacgu auaguaccua ggaacuaagc   360

auguagaggu uagcggggag uuuacuaagg acgagaguuc gacucucucc accuccacca   420

<210> SEQ ID NO 130
<211> LENGTH: 421
<212> TYPE: RNA
<213> ORGANISM: Artificial
<220> FEATURE:
<223> OTHER INFORMATION: Chlamydia trachomatis mouse isolate

<400> SEQUENCE: 130

gggggguguaa agguuucgac uuagaaauga agcguuaauu gcaugcggag ggcguuggcu    60

ggccuccuaa aaagccgaca aaacaauaaa ugccgaaccu aaggcugaau gcgaaauuau   120

cagcuucgcu gaucuuaaug aucuaagagu ugcugcuuaa uuagcaaagu uguuaccuaa   180

guacugguaa cccgguguuc gcgagcucca ccagagguuu ucgaaacgcc gucauuuauc   240

ugguuagaau uagggccuuu uaacucucaa gggaacuaau uugaauuuua augagagucg   300

uuggucucua uagagguuuc uagcugagga gauauaacgu aaaauauucu agaaacuaag   360

cauguagagg uuagcgggga guuuacuaag gacgagaguu cgaaucucuc caccuccacc   420

a                                                                  421

<210> SEQ ID NO 131
<211> LENGTH: 426
<212> TYPE: RNA
<213> ORGANISM: Chlamydia pneumoniae

<400> SEQUENCE: 131

ggggguguau agguuucgac uugaaaauga aguguuaauu gcaugcggag ggcguuggcu    60

ggccuccuaa aaagccaaca aaacaauaaa ugccgaaccu aaggcugaau gcgaaauuau   120

uagcuuguuu gacucaguag aggaaagacu agcugcuuaa uuagcaaaag uuguuagcua   180

gauaaucucu agguaacccg guaucugcga gcuccaccag aggcuugcaa aauaccguca   240

uuuaucuggu uggaacuuac uuucucuaau ucucaaggaa guucguucga gauuuuugag   300

agucauuggc ugcuauagag gcuucuagcu aagggagucc aauguaaaca auucuagaag   360

auaagcaugu agagguuagc agggaguuug ucaaggacga gaguucgagu cucuccaccu   420

ccacca                                                             426

<210> SEQ ID NO 132
<211> LENGTH: 328
<212> TYPE: RNA
```

-continued

<213> ORGANISM: Micrococcus luteus

<400> SEQUENCE: 132
cggugugugu cgcgucggga gaagcgggcc gaggaugcag agucaucucg ucaaacgcuc 60
ucugcaaacc aauaagugcc gaauccaagc gcacugacuu cgcucucgcu gccugaucag 120
ugaucgaguc cgucaccccg aggucgcugu cgccucggau cguggcguca gcuagauagc 180
cacugggcgu cacccucgcc gggggucgug acgccgacau caauccggcu ggguccgggu 240
uggccgcccg ucugcgggac ggccaggacc gagcaacacc cacagcagac ugcgcccgga 300
gaagaccugg caacaccuca ucggacgc 328

<210> SEQ ID NO 133
<211> LENGTH: 368
<212> TYPE: RNA
<213> ORGANISM: Mycobacterium leprae

<400> SEQUENCE: 133
ggggcugaaa gguuucgacu ucgcgcaucg aaucaaggga agcgugccgg ugcaggcaag 60
agaccaccgu aagcgucguu gcagcaauau aagcgccgau ucauaugagc gcgacuaugc 120
ucucgcugcc uaagcgaugg cuagucuguc agaccgggaa cgcccucguc ccggagccug 180
gcaucagcua gagggaucua ccgaugggcu cggucgcggg acucgucggg acaccaaccg 240
cgacugggau cgucauccug gcuaguucgc gugaucagga gauccgagua gaggcauagc 300
gaacuacgca cggagaagcc uugagggaaa ugccguagga cccggguucg auucccggca 360
gcuccacc 368

<210> SEQ ID NO 134
<211> LENGTH: 360
<212> TYPE: RNA
<213> ORGANISM: Mycobacterium tuberculosis

<400> SEQUENCE: 134
ggggcugaac gguuucgacu ucgcgcaucg aaucaaggga agcgugccgg ugcaggcaag 60
agaccaccgu aagcgucguu gcgaccaaau aagcgccgau ucacaucagc gcgacuacgc 120
ucucgcugcc uaagcgacgg cuagucuguc agaccgggaa cgcccucggc ccggacccug 180
gcaucagcua ccaccgauga guccggucgc gggacuccuc gggacaacca cagcgacugg 240
gaucgucauc ucggcuaguu cgcgugaccg ggagauccga gcagaggcau agcgaacugc 300
gcacggagaa gccuugaggg aaugccguag gacccggguu cgauucccgg cagcuccacc 360

<210> SEQ ID NO 135
<211> LENGTH: 373
<212> TYPE: RNA
<213> ORGANISM: Mycobacterium avium

<400> SEQUENCE: 135
ggggcugaaa gguuucgacu ucgcgcaucg aaucaaggga agcgugccgg ugcaggcaac 60
ugaccaccgu aagcgucguu gcagauagau aagcgccgau ucacaucagc gcgacuacgc 120
ucucgcugcc uaagcgacag cuagucgagg gaucgucagc ccgggaacgc ccucgacccg 180
gagccuggcg ucagcuagag ggauccaccg augaguucgg ucgcgggacu caucgggaca 240
ccaacagcga cugggaucgu cauccuggcu uguucgcgug accaggagau ccgaguagag 300
gcauagcgaa cugcgcacgg agaagccuug agggaaugcc guaggacccg gguucgauuc 360
ccggcagcuc cac 373

-continued

<210> SEQ ID NO 136
<211> LENGTH: 331
<212> TYPE: RNA
<213> ORGANISM: Corynebacterium xerosis

<400> SEQUENCE: 136
cuucguacau ugagccaggg gaagcgugcc ggugaaggcu ggagaccacc gcaagcgucg 60
cagcaaccaa uuaagcgccg agaacucuca gcgcgacuac gcccucgcug ccuaagcagc 120
gaccgcgugu cugucagacc ggguaggccu cugauccgga cccuggcauc guuuaguggg 180
gcucgcucgc cgacuugguc gcaagggucg gcggggacac ucacuugcga cugggcccgu 240
cauccgguca uguucgacug aaccggaggg ccgagcagag accacgcgcg aacugcgcac 300
ggagaagccc uggcgaggug acggaggacc c 331

<210> SEQ ID NO 137
<211> LENGTH: 354
<212> TYPE: RNA
<213> ORGANISM: Treponema pallidum

<400> SEQUENCE: 137
ggggaugacu agguuucgac uagggaugug ggguguugcg cugcaggugg agugucgauc 60
uccugauucg gcgccuuuau aacugccaau ucugacaguu ucgacuacgc gcucgccgcg 120
uaaucgcggg ccuguguuug cgcugcucug agcgaacaua ucggcccgac gccaaacgga 180
gcuugcucuu acguugugca cggcggacgu agggggacuu uugucugugc uaagacucug 240
gcgcgugcgg ugcaggccua gcagaguccg acaaacgcag uacgcaccgc uaaaccugua 300
ggcgcgcagc acucgcucuu uaggacgggg guucgauucc ccccaucucc acca 354

<210> SEQ ID NO 138
<211> LENGTH: 362
<212> TYPE: RNA
<213> ORGANISM: Borrelia burgdorferi

<400> SEQUENCE: 138
ggggauguuu uggauuugac ugaaaauguu aauauuguaa guugcaggca gagggaaucu 60
cuuaaaacuu cuaaaauaaa ugcaaaaaau aauaacuuua caagcucaaa ucuuguaaug 120
gcugcuuaag uuagcagagg guuuuguuga auuuggcuuu gagguucacu uauacucuuu 180
ucgacaucaa agcuugcuua aaaauguuuu caaguugauu uuuagggacu uuuauacuug 240
agagcaauuu ggugguuugc uaguauuucc aaaccauauu gcuuaauaaa auacuagaua 300
agcuuguaga agcuuauagu auuauuuuua ggacgcgggu ucaauucccg ccaucuccac 360
ca 362

<210> SEQ ID NO 139
<211> LENGTH: 364
<212> TYPE: RNA
<213> ORGANISM: Borrelia garinii

<400> SEQUENCE: 139
ggggcugauu cuggauucga cugaaaaugc gaauauugua aguugcaggc agagggaauc 60
ucuuaaaacu ucuaaaauaa augcaaaaaa uaauaacuuu acaagcucaa accuuguaau 120
ggcugcuuaa guuagcaggg aguuucguug aauuuggcuu ugagguucac uuauacucuu 180
uucgauaucg aagcuugcuu aaaaauguuu ucaaguuaau uuuuagggac uuuuguacuu 240

-continued

```
gagagcaauu uggcgguuug cuaguauuuc caaaccauau ugcuuaagua aaaugcuaga    300

uaagcuugua gaagcuuaua auauuguuuu uaggacgcgg guucaauucc cgccaucucc    360

acca                                                                 364


<210> SEQ ID NO 140
<211> LENGTH: 363
<212> TYPE: RNA
<213> ORGANISM: Borrelia afzelii

<400> SEQUENCE: 140

ggggcugauu cuggauucga cugaaaaugc uaauauugua aguugcaagc agagggaauc     60

ucuuaaaacu ucuaaaauaa augcaaaaaa uaauaacuuu acaaguucaa accuuguaau    120

ggcugcuuaa guuagcagag aguuuuguug aauuuggcuu ugagauucac uuauacucuu    180

uuagacaucg aagcuugcuu aaaaauguuu ucaaguugau uuuuagggac uuuuauacuu    240

gagagcaauu uggcgguuug cuaguauuuc caaaccauau ugcuuaguaa aauacuagau    300

aagcuuguag aagcuuauag uauuguuuuu aggacgcggg uucaauuccc gccaucucca    360

cca                                                                  363


<210> SEQ ID NO 141
<211> LENGTH: 363
<212> TYPE: RNA
<213> ORGANISM: Borrelia crocidurae

<400> SEQUENCE: 141

ggggcugauu cuggauucga cuaagaacuu uaguagcaua aauggcaagc agagugaauc     60

ucuuaaaacu ucuuuaauaa augcaaaaaa uaauaacuuu acaaguucag aucuuguaau    120

ggcugcuuaa uuuagcagag aguuuuguug gauuuugcuu ugagguucaa cuuauacucu    180

uuaagacauc aaaguaugcc uaaaaauguu ucaaguugau uuuuagggac cuuuaaacuu    240

gagaguaauu uggugguuug cuuguuuucc aagccuuauu gcuuuuucua aaaauuagcu    300

aagcuuguag auauuuauga uauuauuuuu uggacgcggg uucaauuccc gccaucucca    360

cca                                                                  363


<210> SEQ ID NO 142
<211> LENGTH: 365
<212> TYPE: RNA
<213> ORGANISM: Borrelia hermsii

<400> SEQUENCE: 142

ggggcugauu cuggauucga cuaaaaacuu uaguagcaua aauugcaagc agagggaauc     60

ucuuaaaacu ucuuuaauaa augcaagaaa uaauaacuuu acaaguucaa aucuuguaau    120

ggcugcuuaa auuagcagag aguucugcug gauuuugcuu ugagguucag cuuauacucu    180

uuuaagacau caaagcuugc uuaaaaaauau uucaaguuga uuuuuaggga cuuuuaaauu    240

ugagaguaau uuggcgguuu gcuaguuuuu ccaaaccuua uuacuuaaag aaaacacuag    300

cuaagcuugu agauauuuau gauauuauuu uuaggacgcg gguucaauuc ccgccaucuc    360

cacca                                                                365


<210> SEQ ID NO 143
<211> LENGTH: 330
<212> TYPE: RNA
<213> ORGANISM: Alcaligenes faecalis

<400> SEQUENCE: 143
```

-continued

```
cgggggucaa gaagcagcac agggcguguc gagcaccagu acgcucguaa auccacugga     60

aaacuauaaa cgccaacgac gagcguuucg cucuagccgc uuaaggcugg gccacugcac    120

uaauuugucu uuggguuagg uagggcaacc uacagcagug uuauuuacaa agaaucgaau    180

cggucugcgc cacgaagucc gguucuaaaa cuuaguggau cgccaaggaa aggccuguca    240

auuggcauag uccaagguua aaacuuaaaa uuaauugacu acacauguag aacugucugu    300

ggacggcuug cggacggggg uucgauuccc                                     330
```

<210> SEQ ID NO 144
<211> LENGTH: 340
<212> TYPE: RNA
<213> ORGANISM: Alcaligenes eutrophus

<400> SEQUENCE: 144

```
cgugggguuac aaagcagugg agggcauacc gaggacccgu caccucguua aucaauggga     60

augcaauaac ugcuaacgac gaacguuacg cacuggccgc uuaauugcgg ccguccucgc    120

acuggcucgc ugacgggcua gggucgcaag accacgcgag gucauuuacg ucagauaagc    180

uccggaaggg ucacgaagcc ggggacgaaa accuagugac ucgccgucgu agagcguguu    240

cguccgcgau gcgccgguua aaucaaauga cagaacuaag uauguagaac ucucugugga    300

gggcuuacgg acgcggguuc gauucccgcc ggcuccacca                         340
```

<210> SEQ ID NO 145
<211> LENGTH: 326
<212> TYPE: RNA
<213> ORGANISM: Ralstonia pickettii

<400> SEQUENCE: 145

```
cgggguugc gaagcagcgg agggcauacc gaggacccgu caccucguua aucaauggga     60

augcaauaac ugcuaacgac gaacguuacg cacuggcagc cuaagggccg ccguccucgc    120

acuggcucgc ugacgggcua gggucgcaag accagcgagg ucauuuacgu cagauaagcu    180

uuaggugagu cacgggccua gagacgaaaa cuuagugaau cgccgucgua gagcguguuc    240

guccgcgaug cggcgguuaa aucaaaugac agaacuaagu auguagaacu cucuguggag    300

ggcuugcgga cgcggguucg auuccc                                         326
```

<210> SEQ ID NO 146
<211> LENGTH: 363
<212> TYPE: RNA
<213> ORGANISM: Neisseria gonorrhoeae

<400> SEQUENCE: 146

```
gggggcgacc uugguuucga cgggggguugc gaagcagaug cgggcauacc ggggucucag     60

auucccguaa aacacugaau ucaaauaguc gcaaacgacg aaacuuacgc uuuagccgcu    120

uaaggcuagc cguugcagca gucggucaau gggcugugug gugaaagcca ccgcaacguc    180

aucuuacauu gacugguuuc cagccggguu acuuggcagg aaauaagacu uaagguaacu    240

gguuuccaaa aggccuguug gucggcauga uggaaauaag auuuucaaau agacacaacu    300

aaguauguag aacgcuuugu agaggacuuu cggacggggg uucgauuccc cccgccucca    360

cca                                                                  363
```

<210> SEQ ID NO 147
<211> LENGTH: 363
<212> TYPE: RNA

-continued

<213> ORGANISM: Neisseria meningitidis

<400> SEQUENCE: 147

```
gggggcgacc uugguuucga cgggggguugc gaagcagaug cgggcauacc ggggucucag     60
auucccguaa aacacugaau ucaaauaguc gcaaacgacg aaacuuacgc uuuagccgcu    120
uaaggcuagc cguugcagca gucggucaau gggcugugug gcgaaagcca ccgcaacguc    180
aucuuacauu gacugguuuc cugccgggu auuuggcagg aaaugagauu uaagguaacu    240
gguuuccaaa aggccuguug gucggcauga uggaaauaag auuuucaaau agacacaacu    300
aaguauguag aacgcuuugu agaggacuuu cggacggggg uucgauuccc cccgccucca    360
cca                                                                  363
```

<210> SEQ ID NO 148
<211> LENGTH: 333
<212> TYPE: RNA
<213> ORGANISM: Chromobacterium violaceum

<400> SEQUENCE: 148

```
cgggggguugc gaagcagaug agggcauacc gggauuucag ucacccccgua aaacgcugaa     60
uuuauauagu cgcaaacgac gaaacuuacg cucuggcagc cuaacggccg gccagacacu    120
acaacgguuc gcagaugggc cgggggcguc aaaacccugu agugucacuc uacaucugcu    180
agugcuguuc cggguuacuu gguucagugc gaaauaauag guaacucgcc aaaguccagc    240
cuguccgucg gcguggcaga gguuaaaucc aaaugacacg acuaaguaug uagaacucac    300
uguagaggac uuucggacgc ggguucaacu ccc                                 333
```

<210> SEQ ID NO 149
<211> LENGTH: 330
<212> TYPE: RNA
<213> ORGANISM: Nitrosomonas cryotolerans

<400> SEQUENCE: 149

```
cgugggguugc aaagcagcgc agggcauacc gaggaccaga auaccucgua aauacaucug     60
gaaaaaaaua gucgcaaacg acgaaaacua cgcuuuagcc gcuuaauacg gcuagccucu    120
gcaccgaugg gccuuaacgu cgggucuggc aacagacagc agagucauua gcaaggaucg    180
cguucuguag ggucacuuua cagaacguua aacaauaggu gacucgccug ccaucagccc    240
gccagcuggc gguugucagg uuaaauuaaa gagcauggcu aaguauguag aacugucugu    300
agaggacuug cggacgcggg uucaacuccc                                     330
```

<210> SEQ ID NO 150
<211> LENGTH: 331
<212> TYPE: RNA
<213> ORGANISM: Methylobacillus glycogenes

<400> SEQUENCE: 150

```
cgggggguugc aaagcagcgc agggcauacc gaggccuagu caccucguaa auaaacuaga     60
acaaguauag ucgcaaacga cgaaacuuac gcucuagccg cuuaaucccg gcuggacgcu    120
gcaccgaagg gccucucggu cgggugggu aacccacagc agcgucauua agagaggauc    180
gugcgauauu ggguuacuua auaucguauu aaauccaagg uaacucgccu gcuguuugcu    240
ugcucguugg ugagcaucag guuaaaucaa acaacacagc uaaguaugua gaacugucug    300
uggagggcuu gcggacgggg guucgauucc c                                   331
```

<210> SEQ ID NO 151
<211> LENGTH: 375
<212> TYPE: RNA
<213> ORGANISM: Pseudomonas testosteroni

<400> SEQUENCE: 151
ggggccgauu cuggauucga cgugggUucg gaccggugc ggugcaugUc gagcuugagu        60
gacgcucgua aaucuccauu caaaaaacua acugcaaacg acgaacguuu cgcacucgcc      120
gcuuaauccg gugagccuug caacagcacg cuagugggcu gggcaagggg guagcaauac      180
cucccggcug caagggaauu ucauuagcu ggcuggauac cgggcuucuu gguauuuggc       240
gagauuuuag gaagcuggcu acccaagcag cgugugccug cggggUuugg guggcgagau      300
uuaaaacaga gcacuaaaca uguagaucug uccggcgaag gcuuacggac gcggguUcaa      360
uucccgccgg cucca                                                     375

<210> SEQ ID NO 152
<211> LENGTH: 353
<212> TYPE: RNA
<213> ORGANISM: Variovorax paradoxus

<400> SEQUENCE: 152
cgugggUucg gagucgcagc ggggcauguc gagcugaaug cgcucguaaa acagauucaa       60
acaaacuaac ugcaaacgac gaacguuucg cacucgcugc uuaauugcca gugagccuug      120
caacaguugg ccgaugggcu gggcaagggg gucuggagca auccugaccu cccggcugca     180
aggauaacua caugggcugg cuccgauccg gguaccuugg gucggggcga gaaaauaggg     240
uacuggcguc cgguuuagcg ugugacugcg cgacuccgga agcgagacuc aaaacagauc     300
acuaaacaug uagaacugcg cgaugaaggc uugcggacgg ggguucaacu ccc            353

<210> SEQ ID NO 153
<211> LENGTH: 345
<212> TYPE: RNA
<213> ORGANISM: Hydrogenophaga palleroni

<400> SEQUENCE: 153
cgugggUucg gacgcgcagc agggcauguc gagguucugu caccucguaa aucagcagaa       60
aaaaaccaac ugcaaacgac gaacguuucg cacucgccgc uuaaacaccg gugagccuug      120
caacagcagg ccgaugggcu gggcaagggg gucgcaagac cucccggcug caagguaauu     180
uacaucggcu gguucugcgu cgggcaccuu ggcgcaggau gagauucaag gaugcuggcu     240
ucccguuuag cgugccacug cgcgacucgg gcggcgagac ccaaaucaga cggcuacaca     300
uguagaacug cucgaaaaag gcuugcggac gggggUucaa cuccc                     345

<210> SEQ ID NO 154
<211> LENGTH: 387
<212> TYPE: RNA
<213> ORGANISM: Bordetella pertussis

<400> SEQUENCE: 154
ggggccgauc cggauucgac gugggucaug aaacagcuca gggcaugccg agcaccagua 60
agcucguuaa uccacuggaa cacuacaaac gccaacgacg agcgucucgc ucucgccgcu 120
uaagcgguga gccgcugcac ugaucugucc uugggucagg cgggggaagg caacuuccca 180
gggggcaacc ccgaaccgca gcagcgacau ucacaaggaa ucggccaccg cuggggucac 240
acggcguugg uuuaaauuac gugaaucgcc cugguccggc ccgucgaucg gcuaagucca 300

-continued ggguuaaauc caaauagauc gacuaagcau guagaacugg uugcggaggg cuugcggacg 360
gggguucaau uccccccggc uccacca 387

<210> SEQ ID NO 155
<211> LENGTH: 323
<212> TYPE: RNA
<213> ORGANISM: Legionella pneumophila

<400> SEQUENCE: 155 cgugggguugc aaaaccggaa gugcaugccg agaaggagau cucucguaaa uaagacucaa 60
uuaaauauaa augcaaacga ugaaaacuuu gcuggugggg aagcuaucgc ugccuaauaa 120
gcacuuuagu uaaaccauca cuguguacug gccaauaaac ccaguauccc guucgaccga 180
gcccgcuuau cgguaucgaa ucaacgguca uaagagauaa gcuagcgucc uaaucuaucc 240
cggguuaugg cgcgaaacuc agggaaucgc uguguaucau ccugcccguc ggaggagcca 300
caguuaaauu caaaagacaa ggc 323

<210> SEQ ID NO 156
<211> LENGTH: 315
<212> TYPE: RNA
<213> ORGANISM: Chromatium vinosum

<400> SEQUENCE: 156
cgugggucgc gaaaccuaag gugcaugccg aggugcgguu gaccucguaa aacccuccgc 60
aaacuuauag uugccaacga cgacaacuac gcucucgcug cuuaauccca gcgggccucu 120
gaccgucacu ugccuguggg cggcggauuc caggggguaac cucacacagg aucgugguga 180
cgggaguccg gaccugaucc acuaaaaccu aacggaaucg ccgacugauc gcccugcccu 240
ucgggcggca gaaggcuaaa aacaauagag ugggcuaagc auguaggacc gagggcagag 300
ggcuugcgga cgcgg 315

<210> SEQ ID NO 157
<211> LENGTH: 318
<212> TYPE: RNA
<213> ORGANISM: Dichelobacter nodosus

<400> SEQUENCE: 157
cucgaggugc augucgagaa ugagagaauc ucguuaaaua cuuucaaaac uuauaguugc 60
aaacgacgac aacuacgcuu uagcggcuua auucccgcuu ucgcuuaccu agauuugucu 120 gugggguuuac cguaagcgac auuaacacag aaucgcuggu uaacgcgucc gcuguuaauc 180
gguuaaauua agcggaaucg cuuguaaaau gccugagcgu uggcuguuua ugaguuaaac 240
cuaauuaacu gcucuaaaca uguaguacca aaaguuaagg auucgcggac gggggguucaa 300 aucccccccgc cuccacca 318

<210> SEQ ID NO 158
<211> LENGTH: 354
<212> TYPE: RNA
<213> ORGANISM: Pseudomonas aeruginosa

<400> SEQUENCE: 158
ggggccgauu aggauucgac gccgguaaca aaacuugagg ggcaugccga gcugguagca 60
gaacucguaa auucgcugcu gcaaacuuau aguugccaac gacgacaacu acgcucuagc 120
ugcuuaaugc ggcuagacag ucgcuagggg augccuguaa acccgaaacg acugucagau 180
agaacaggau cgccgccaag uucgcuguag acguaacggc uaaaacucau acagcucgcu 240

-continued ccaagcaccc ugccacucgg gcggcgcgga guuaacucag uagagcuggc uaagcaugua 300
gaaccgauag cggagagcug gcggacgggg guucaaaucc ccccggcucc acca 354

<210> SEQ ID NO 159
<211> LENGTH: 350
<212> TYPE: RNA
<213> ORGANISM: Pseudomonas fluorescens

<400> SEQUENCE: 159
cgccgguugc gaaccuuuag gugcaugccg aguugguaac agaacucgua aauccacugu 60
ugcaacuuuc uuaguugcca augacgaaac cuacggggaa uacgcucucg cugcguaagc 120
agccuuagcc cuucccuccu gguaccuucg gguccagcaa ucaucagggg augucuguaa 180
acccaaagug auugucauau agaacagaau cgccgugcag uacguugugg acgaagcggc 240
uaaaacuuac acaacucgcc caaagcaccc ugcccgucgg gucgcugagg guuaacuuaa 300
uagacacggc uacgcaugua guaccgacag cagaguacug gcggacgggg 350

<210> SEQ ID NO 160
<211> LENGTH: 323
<212> TYPE: RNA
<213> ORGANISM: Marinobacter hydrocarbonoclasticus

<400> SEQUENCE: 160
cgccggugac gaacccuugg gugcaugccg agauggcagc gaaucucgua aauccaaagc 60
ugcaacguaa uagucgcaaa cgacgaaaac uacgcacugg cggcguaagc cguuccaguc 120
guccuggcug aggcgccuau aacucaguag caacauccca ggacgucauc gcuuauaggc 180
ugcuccguuc accagagcuc acugguguuc ggcuaagauu aaagagcucg ccucuugcac 240
ccugaccuuc gggucgcuug agguuaaauc aauagaagga cacuaagcau guagaccuca 300
aggccuagug cuggcggacg cgg 323

<210> SEQ ID NO 161
<211> LENGTH: 355
<212> TYPE: RNA
<213> ORGANISM: Shewanella putrefaciens

<400> SEQUENCE: 161
gggggcgauu cuggauucga caggauucac gaaacccugg gagcaugccg aggggcgguu 60
ggccucguaa aaagccgcaa aguuauaguu gcaaacgacg auaacuacgc ucuagccgcu 120
uaaugccgcu agccaucuac cacacgcuuu gcacaugggc aguggauuug auggucaucu 180
cacaucgugc uagcgaggga acccugucug ggggugaacc gcgaaacagu accggacuca 240
ccgugaggga uccugucuuu cggaguucaa acgguuaaac aauagaaaga cuaagcaugu 300
agcgccuugg auguagguuu ucuggacgcg gguucaaguc ccgccgccuc cacca 355

<210> SEQ ID NO 162
<211> LENGTH: 314
<212> TYPE: RNA
<213> ORGANISM: Pseudoalteromonas haloplanktis

<400> SEQUENCE: 162
cggaauucaa gaagcccgag gugcaugucg aggugcgguu ugccucguaa aaaagccgca 60
auuuaaagua aucgcaaacg acgauaacua cucucuagca gcuuaggcug gcuagcgcuc 120
cuuccaugua uucuugugga cuggauuuug gagugucacc cuaacaccug aucgcgacgg 180

-continued

```
aaacccuggc cggggguugaa gcguuaaaac uaagcggccu cgccuuuauc uaccguguuu    240

guccgggauu uaaagguuaa uuaaaugaca auacuaaaca uguaguaccg acggucgagg    300

cuuuucggac gggg                                                      314


<210> SEQ ID NO 163
<211> LENGTH: 316
<212> TYPE: RNA
<213> ORGANISM: Aeromonas salmonicida

<400> SEQUENCE: 163

caagauucac gaaacccaag gugcaugccg aggugcggua ggccucguua acaaaccgca     60

aaaaaauagu cgcaaacgac gaaaacuacg cacuagcagc uuaauaaccu gcauagagcc    120

cuucuacccu agcuugccug uguccuaggg aaucggaagg ucauccuuca caggaucgug    180

uggaaguccu gcucggggcg gaagcauuaa aaccaaucga gcuagucaau ucguggcgug    240

ucucuccgca gcggguuggc gaauguaaag agugacuaag cauguaguac cgaggaugua    300

guaauuuugg acgggg                                                    316


<210> SEQ ID NO 164
<211> LENGTH: 363
<212> TYPE: RNA
<213> ORGANISM: Salmonella typhimurium

<400> SEQUENCE: 164

ggggcugauu cuggauucga cgggauuugc gaaacccaag gugcaugccg aggggcgguu     60

ggccucguaa aaagccgcaa aaaaauaguc gcaaacgacg aaaccuacgc uuuagcagcu    120

uaauaaccug cuuagagccc ucucucccua gccuccgcuc uuaggacggg gaucaagaga    180

ggucaaaccc aaaagagauc gcgcggaugc ccugccuggg guugaagcgu uaaaacgaau    240

caggcuaguc ugguaguggc guguccgucc gcaggugcca ggcgaaugua aagacugacu    300

aagcauguag uaccgaggau guaggaauuu cggacgcggg uucaacuccc gccagcucca    360

cca                                                                  363


<210> SEQ ID NO 165
<211> LENGTH: 363
<212> TYPE: RNA
<213> ORGANISM: Escherichia coli

<400> SEQUENCE: 165

ggggcugauu cuggauucga cgggauuugc gaaacccaag gugcaugccg aggggcgguu     60

ggccucguaa aaagccgcaa aaaauagucg caaacgacga aaacuacgcu uuagcagcuu    120

aauaaccugc uuagagcccu cucucccuag ccuccgcucu uaggacgggg aucaagagag    180

gucaaaccca aaagagaucg cguggaagcc cugccugggg uugaagcguu aaaacuuaau    240

caggcuaguu uguuaguggc guguccgucc gcagcuggca agcgaaugua aagacugacu    300

aagcauguag uaccgaggau guaggaauuu cggacgcggg uucaacuccc gccagcucca    360

cca                                                                  363


<210> SEQ ID NO 166
<211> LENGTH: 364
<212> TYPE: RNA
<213> ORGANISM: Yersinia pestis

<400> SEQUENCE: 166

ggggcugauu cuggauucga cgggauucgc gaaacccaag gugcaugccg aggugcggug     60
```

-continued gccucguaaa aaaccgcaaa aaaaauaguu gcaaacgacg aaaacuacgc acuagcagcu 120
uaauaaccug cuuagagccc ucucucccua gccuccgcuc uuaggacggg gaucaagaga 180
ggucaaaccu aaaagagcuc guguggaaac cuugccuggg guggaagcau uaaaacuaau 240
caggauaguu ugucaguagc guguccaucc gcagcuggcc ggcgaaugua augauuggac 300
uaagcaugua gugccgacgg uguaguaauu ucggacgggg guucaaaucc ccccagcucc 360
acca 364

<210> SEQ ID NO 167
<211> LENGTH: 367
<212> TYPE: RNA
<213> ORGANISM: Vibrio cholerae

<400> SEQUENCE: 167
ggggcugauu caggauucga cgggaauuuu gcagucugag gugcaugccg aggugcggua 60
ggccucguua acaaaccgca aaaaaauagu cgcaaacgac gaaaacuacg cacuagcagc 120
uuaauacccu gcucagagcc cuuccucccu agcuuccgcu uguaagacgg ggaaaucagg 180
aaggucaaac caaaucaagc uggcguggau ucccccaccu gagggaugaa gcgcgagauc 240
uaauucaggu uagccauucg uuagcguguc gguucgcagg cgguggugaa auuaaagauc 300
gacuaagcau guaguaccaa agaugaaugg uuuucggacg gggguucaac uccccccagc 360
uccacca 367

<210> SEQ ID NO 168
<211> LENGTH: 366
<212> TYPE: RNA
<213> ORGANISM: Haemophilus influenzae

<400> SEQUENCE: 168
ggggcugauu cuggauucga cgggauuagc gaagcccaag gugcacgucg aggugcggua 60
ggccucguaa auaaaccgca aaaaaauacu cgcaaacgac gaacaauacg cuuuagcagc 120
uuaauaaccu gcauuuagcc uucgcgcucc agcuuccgcu cguaagacgg ggauaacgcg 180
gagucaaacc aaaacgagau cguguggaag ccaccguuug aggaucgaag cacuaaauug 240
aaucaaacua gcuuaaguuu agcgugucug uccgcaugcu uaagugaaau uaaagacgag 300
acuaaacgug uaguacugaa gguagaguaa uuucggacgg ggguucaacu ccccccagcu 360
ccacca 366

<210> SEQ ID NO 169
<211> LENGTH: 366
<212> TYPE: RNA
<213> ORGANISM: Haemophilus actinomycetemcomitans

<400> SEQUENCE: 169
ggggcugauu cuggauucga cgggauuagc gaagcccgaa gugcacgucg aggugcggua 60
ggccucguaa auaaaccgca aaaaaauagu cgcaaacgac gaacaauacg cuuuagcagc 120
uuaauaaccu gccuuuagcc uucgcucccc agcuuccgcu cguaagacgg ggauaaagcg 180
gagucaaacc aaaacgagau cguguggaag ccaccguuug aggaucgaag cauuaaauua 240
aaucaaagua gcuuaauugu cgcguguccg ucagcaggau uaagugaauu uaaagaccgg 300
acuaaacgug uagugcuaac ggcagaggaa uuucggacgg ggguucaacu ccccccagcu 360
ccacca 366

-continued

<210> SEQ ID NO 170
<211> LENGTH: 354
<212> TYPE: RNA
<213> ORGANISM: Desulfovibrio desulfuricans

<400> SEQUENCE: 170
cggggacgug gaagccguag cggcaggucg aggcgccgcu ggccucguaa aaagcggcac 60
aaaaguaauu gccaacaacg auuacgacua cgcuuacgcu gccuaauaac agcgaggcaa 120
ugaccguuua acggucgcgc cgaucagggc caugccugau aacccugauu cacuuaucag 180
gcuggcgaaa accggcucuc gccgggguuu uucgcgagga guuuaccggc gggauuccug 240
cguugugccu ggucaggggc caacagcgcg gugaaauaca uacuugaccu aaaccuguag 300
augcuucgug uggaauguuc ucggacgggg guucaaaucc ccccggcucc acca 354

<210> SEQ ID NO 171
<211> LENGTH: 366
<212> TYPE: RNA
<213> ORGANISM: Myxococcus xanthus

<400> SEQUENCE: 171
gggggcggaa aggauucgac gggggcauug aaguucgaga cgcgugccga gcuugucagg 60
uagcucguaa auucaacccg gcaaagacac aaaagccaac gacaacguug agcucgcgcu 120
ggcugccuaa aaacagccca uagugcgcgg uccccccgcc cucggccugu gggguuggga 180
cagaccguca uaaugcaggc uggcugccga gggugccugg acccgaggug gcgagaucuu 240
cccaggaccg gcucugagua ucccguccgu gggagccuca gggacguagc aaaucgcgga 300
cuacgcacgu agggucgaag agcggacggc uuucggacgc ggguucgauu cccgccgccu 360
ccacca 366

<210> SEQ ID NO 172
<211> LENGTH: 346
<212> TYPE: RNA
<213> ORGANISM: Bdellovibrio bacteriovirus

<400> SEQUENCE: 172
gggggcggaa aggauucgac gggggugcug aagcauaagg agcauaccgg ggcggaugag 60
gaccucguua aaaacgucca cuuuguaauu ggcaacgauu acgcacuugc agcuuaauua 120
agcagcacga ucaaccuugu gguguuccg cacuuggauu gaucgucauu uagggaccuc 180
ggcguguugg guuuucucca gcagacaugc uuaaauuuac ugggggagag gucuuaggga 240
uuuugucugu ggaagcccga ggaccaaucu aaaacacuga cuaaguaugu agcgccuuau 300
cguggaucau uugcggacgg ggguucgauu cccgccgccu ccacca 346

<210> SEQ ID NO 173
<211> LENGTH: 386
<212> TYPE: RNA
<213> ORGANISM: Helicobacter pylori

<400> SEQUENCE: 173
ggggcugacu uggauuucga cagauuucuu gucgcacaga uagcaugcca agcgcugcuu 60
guaaaacagc aacaaaaaua acuguaaaca acacagauua cgcuccagcu uacgcuaaag 120
cugcgugagu uaaucuccuu uuggagcugg acugauuaga auuucuagcg uuuuaaucgc 180
uccauaaccu uaagcuagac gcuuuuaaaa ggugguucgc cuuuuaaacu aagaaacaag 240
aacucuugaa acuaucucaa gguuuuagaa aguuggacca gagcuaguuu uaaggcuaaa 300

-continued

```
aaaccaacca auuuucuaag cauuguagaa guuuguguuu agggcaagau uuuuggacug    360

ggguucgauu ccccacagcu ccacca                                         386


<210> SEQ ID NO 174
<211> LENGTH: 359
<212> TYPE: RNA
<213> ORGANISM: Campylobacter jejuni

<400> SEQUENCE: 174

gggagcgacu uggcuucgac aggaguaagu cugcuuagau ggcaugucgc uuugggcaaa     60

gcguaaaaag cccaaauaaa auuaaacgca aacaacguua aauucgcucc ugcuuacgcu    120

aaagcugcgu aaguucaguu gagccugaaa uuuaagucau acuaucuagc uuaauuuucg    180

gucauuuuug auaguguagc cuugcguuug acaagcguug aggugaaaua aagucuuagc    240

cuugcuuuug aguuuuggaa gaugagcgaa guagggugaa guagucaucu uugcuaagca    300

uguagagguc uuugugggau uauuuuugga caggggguucg auuccccucg cuuccacca    359


<210> SEQ ID NO 175
<211> LENGTH: 355
<212> TYPE: RNA
<213> ORGANISM: Sulfurospirillum deleyianum

<400> SEQUENCE: 175

caggaguagu uuuagcuuau ggcugcaugu cgggagugag ggucuuccgu uacacaaccu     60

ucaaacaaua acugcuaaca acaguaacua ucguccugcu uacgcgcuag cugcguaagu    120

uuaacaaaua auggacugcu cuccccuuug augcuaucuu aggaggucuu ggagaguauc    180

auagauuuga uagcuauauu acaugaacgc cuuuacaugu aaugaaguua aaggcucguu    240

uucguaguuu ucugauuguu guacgaagca aaauuaaaca cuaucaacaa uaucuaagca    300

uguagacguc auaggugcu auuuuuggac uggggguucaa cucccgccag cucca         355
```